US006716811B1

(12) United States Patent  
Cwirla et al.

(10) Patent No.: US 6,716,811 B1
(45) Date of Patent: Apr. 6, 2004

(54) COMPOUNDS HAVING AFFINITY FOR THE GRANULOCYTE-COLONY STIMULATING FACTOR RECEPTOR (G-CSFR) AND ASSOCIATED USES

(75) Inventors: Steven E. Cwirla, Menlo Park, CA (US); Palani Balu, Cupertino, CA (US); David J. Duffin, Durham, NC (US); Sunila Piplani, Mountain View, CA (US); Barbara McEowen Merrill, Durham, NC (US); Peter J. Schatz, Cupertino, CA (US)

(73) Assignee: Affymax, Inc., Palo Alto, CA (US)

( * ) Notice: Subject to any disclaimer, the term of this patent is extended or adjusted under 35 U.S.C. 154(b) by 43 days.

(21) Appl. No.: 09/620,091

(22) Filed: Jul. 20, 2000

(51) Int. Cl.[7] .................. A01N 43/04; A61K 38/00; C07K 17/00
(52) U.S. Cl. .............. 514/2; 514/12; 514/13; 514/14; 530/350; 530/324
(58) Field of Search .................. 536/23.5; 530/324, 530/325, 326, 327; 514/2, 12, 13, 14

(56) References Cited

U.S. PATENT DOCUMENTS

| | | | |
|---|---|---|---|
| 5,298,603 A | 3/1994 | Habermann et al. |
| 5,358,707 A | 10/1994 | Reichert et al. |
| 5,589,456 A | 12/1996 | Smith et al. |
| 5,651,963 A | 7/1997 | Halenbeck et al. |
| 5,773,581 A | 6/1998 | Camble et al. |
| 5,824,778 A | 10/1998 | Ishikawa et al. |
| 6,100,070 A | 8/2000 | Zurfluh et al. |

FOREIGN PATENT DOCUMENTS

EP   0494260 B1   7/1992

*Primary Examiner*—Bradley L. Sisson
(74) *Attorney, Agent, or Firm*—Biotechnology Law Group; Edward O. Kreusser, Esq.

(57) ABSTRACT

Novel compounds are provided that bind to G-CSFR. The novel compounds have a peptide chain approximately 6 to 40 amino acids in length that binds to G-CSFR. The compounds are useful as probes for affinity screening. In addition, the compounds have demonstrated agonist or antagonist activity for the G-CSFR, and are therefore useful in treatment of diseases including patients who suffer from a low white blood cell titer. Pharmaceutical compositions and methods of use are provided as well.

7 Claims, 18 Drawing Sheets

FIG. 1A

CAGEVMHMCC (SEQ ID NO: 8)
CNREIEAMCC (SEQ ID NO: 9)
CADEVMHFCC (SEQ ID NO: 10)
CNREIMWMCC (SEQ ID NO: 11)
CSHEVWWYCC (SEQ ID NO: 12)
CSREVLYYCC (SEQ ID NO: 13)
CFIEGPWVCC (SEQ ID NO: 14)
CFVEGNWYCC (SEQ ID NO: 15)
CAAEVMVNCC (SEQ ID NO: 16)
CSDEVIFYCC (SEQ ID NO: 17)
CDREIMWFCC (SEQ ID NO: 18)
CAHEVMWMCC (SEQ ID NO: 19)
CGSEVTFMCC (SEQ ID NO: 20)
CLEEIMWLCC (SEQ ID NO: 21)
CAREVLAMCC (SEQ ID NO: 22)
CSVEVMQMCC (SEQ ID NO: 23)
CTNVQLMHYC (SEQ ID NO: 24)
CDVWQLFDRC (SEQ ID NO: 25)
CSFVQLNSIC (SEQ ID NO: 26)
CDYWQWFDKC (SEQ ID NO: 27)
CESFWVELWC (SEQ ID NO: 28)
CVPWMFYDLC (SEQ ID NO: 29)
CDPWMFYDLC (SEQ ID NO: 30)
CDPWVLFDEC (SEQ ID NO: 31)
CDHWTYFDMC (SEQ ID NO: 32)
CVVWTLYDKC (SEQ ID NO: 33)
CPDWYQSYMC (SEQ ID NO: 34)
CPDWYSYYMC (SEQ ID NO: 35)
CPEWYTDVMC (SEQ ID NO: 36)
CPDWYLDYMC (SEQ ID NO: 37)
CPEWYLDYMC (SEQ ID NO: 38)
CPDWYLPYMC (SEQ ID NO: 39)
CPEWYLPYMC (SEQ ID NO: 40)
CQDWWVELWC (SEQ ID NO: 41)
CPDWYLPWMC (SEQ ID NO: 42)
CACMLRVVHC (SEQ ID NO: 43)
CQRAGYMLAC (SEQ ID NO: 44)
CHANPVWGEC (SEQ ID NO: 45)
CFWSDWGQTC (SEQ ID NO: 46)
CPHWTSYYMC (SEQ ID NO: 47)
CETLCGACFC (SEQ ID NO: 48)
CATTINDTLC (SEQ ID NO: 49)
CLNYPHPVFC (SEQ ID NO: 50)

FIG. 1B

CMDGEMAVDC (SEQ ID NO: 51)
CNMGWMSWPC (SEQ ID NO: 52)
CETYADWLGC (SEQ ID NO: 53)
CDPWMFFDMC (SEQ ID NO: 54)
CDPWIWYDLC (SEQ ID NO: 55)
CDPWIMYDRC (SEQ ID NO: 56)
CDPWVFFDIC (SEQ ID NO: 57)
CDPWTYYDLC (SEQ ID NO: 58)
CDPWIFYDRC (SEQ ID NO: 59)
CDPWLFYDLC (SEQ ID NO: 60)
CDPWVWYDLC (SEQ ID NO: 61)
CDPWIFFDRC (SEQ ID NO: 62)
CDPWMFFDQC (SEQ ID NO: 63)
CDPWLWYDRC (SEQ ID NO: 64)
CDVWVWYDQC (SEQ ID NO: 65)
CDPWIYYDLC (SEQ ID NO: 66)
CVPWTLFDLC (SEQ ID NO: 67)
CPAWYLEYMC (SEQ ID NO: 68)
CPDWYLEYMC (SEQ ID NO: 69)
CKYWQWFDKC (SEQ ID NO: 70)
CDHWMWYDKC (SEQ ID NO: 71)
GCNREIEAMCCG (SEQ ID NO: 72)
GCPEWYTDVMCG (SEQ ID NO: 73)
NWYCMDGEMAVDCEAT (SEQ ID NO: 74)
WQSCNMGWMSWPCYFV (SEQ ID NO: 75)
HELCETYADWLGCVEW (SEQ ID NO: 76)
PCDPWMFFDMCERW (SEQ ID NO: 77)
LRGCDPWIWYDLCPAV (SEQ ID NO: 78)
GYLCDPWIFYDRCLGF (SEQ ID NO: 79)
RFACDPWVFFDICGYW (SEQ ID NO: 80)
GYWCDPWTYYDLCLTA (SEQ ID NO: 81)
MWTCDPWIFYDRCFLN (SEQ ID NO: 82)
GSSCDPWLFYDLCLLD (SEQ ID NO: 83)
GGGCDPWVWYDLCWCD (SEQ ID NO: 84)
YTSCDPWIFFDRCMSV (SEQ ID NO: 85)
DPYCDPWMFFDQCAYL (SEQ ID NO: 86)
REFCDPWLWYDRCL (SEQ ID NO: 87)
NTGCDVWVWYDQCFAM (SEQ ID NO: 88)
LVFCDPWIYYDLCMDT (SEQ ID NO: 89)
GCSFVQLNSICG (SEQ ID NO: 90)
GCPAWYLEYMCG (SEQ ID NO: 91)
GCPDWYLEYMCG (SEQ ID NO: 92)
GCKYWQWFDKCG (SEQ ID NO: 93)
GCDHWMWYDKCG (SEQ ID NO: 94)
SNESGWVWL (SEQ ID NO: 95)

FIG. 1C

QSNSGWVWV (SEQ ID NO: 96)
RTESGWVWT (SEQ ID NO: 97)
RANSGWVWV (SEQ ID NO: 98)
YDNSGWVWH (SEQ ID NO: 99)
LSDSGWVWVP (SEQ ID NO: 100)
EQSNSGWVWVGGGGC (SEQ ID NO: 101)
CEQSNSGWVWV (SEQ ID NO: 102)
EQSNSGWVWVGGGGCKKK (SEQ ID NO: 103)
EQSNSGWVWVGKKKC (SEQ ID NO: 104)
EQSNSGWVWVGKKK (SEQ ID NO: 105)
KKKEQSNSGWVWV (SEQ ID NO: 106)
EQSNSGWVWVGKKKSKKK (SEQ ID NO: 107)
EQSNSGWVWVGGCKKK (SEQ ID NO: 108)
EQSNSGWVWVGGGGGCKKK (SEQ ID NO: 109)
SNESGWVWLP (SEQ ID NO: 110)
EQSNSGWVWV (SEQ ID NO: 111)
SRTESGWVWT (SEQ ID NO: 112)
QRANSGWVWV (SEQ ID NO: 113)
DYDNSGWVWH (SEQ ID NO: 114)
EQSNSGWVWVGKKKK (SEQ ID NO: 115)
EQSNSGWVWVGGGGSKKK (SEQ ID NO: 116)
EQSNSGWVWVGGGGS (SEQ ID NO: 117)
EQSNSGWVWVGGGGSEQSNSGWVWVGGGGS (SEQ ID NO: 118)
RYQSFELSDSGWVWVPVARH (SEQ ID NO: 119)
ERDWFC (SEQ ID NO: 120)
ERDWGC (SEQ ID NO: 121)
ERLWFC (SEQ ID NO: 122)
ERSYFC (SEQ ID NO: 123)
ERGWFC (SEQ ID NO: 124)
EREWFC (SEQ ID NO: 125)
ERAWFC (SEQ ID NO: 126)
ERLYFC (SEQ ID NO: 127)
ERYFMC (SEQ ID NO: 128)
ERLFLC (SEQ ID NO: 129
ERALMC (SEQ ID NO: 130)
ERDVMC (SEQ ID NO: 131)
ERKWFC (SEQ ID NO: 132)
ETWGERDWFC (SEQ ID NO: 133)
ETWGERDWGC (SEQ ID NO: 134)
STAERLWFCG (SEQ ID NO: 135)
YETAERSYFC (SEQ ID NO: 136)
ADNAERGWFC (SEQ ID NO: 137)
QSNSEREWFC (SEQ ID NO: 138)
STSERAWFCG (SEQ ID NO: 139)
ASWSERGWFC (SEQ ID NO: 140)

FIG. 1D

ELSSEREWFC (SEQ ID NO: 141)
DMQGERGWFC (SEQ ID NO: 142)
SSSERAWFCG (SEQ ID NO: 143)
GNMRERLYFC (SEQ ID NO: 144)
QPNRERYFMC (SEQ ID NO: 145)
SVTRERLFLC (SEQ ID NO: 146)
IPLSERALMCSSWNC (SEQ ID NO: 147)
WARSERDVMCLSYVC (SEQ ID NO: 148)
QSNSEREWFCG (SEQ ID NO: 149)
QSNSEREWFCGGGS (SEQ ID NO: 150)
NLEEALAQERLWFCRSGNC (SEQ ID NO: 151)
NLESYEMEERKWFCKMFSC (SEQ ID NO: 152)
DMVYAYPPW (SEQ ID NO: 153)
EMVYTVPYW (SEQ ID NO: 154)
DMVYAYPPWS (SEQ ID NO: 155)
DEMVYTVPYW (SEQ ID NO: 156)
CESRLVECSRMC (SEQ ID NO: 157)
CETYMTYVYWLC (SEQ ID NO: 158)
CGERLAECARLC (SEQ ID NO: 159)
CESRLRECSMLC (SEQ ID NO: 160)
CEARLSECSRIC (SEQ ID NO: 161)
CPARLLECSRMC (SEQ ID NO: 162)
CESVGVGDWWSC (SEQ ID NO: 163)
CEDRLVEGPWVC (SEQ ID NO: 164)
CNDQFRTCVDVC (SEQ ID NO: 165)
CRGEWWELYHPC (SEQ ID NO: 166)
CEDTRTGWAWSC (SEQ ID NO: 167)
CTWLSSGELVWC (SEQ ID NO: 168)
CWPPVCEVSGIC (SEQ ID NO: 169)
CSLSPIQLQHLC (SEQ ID NO: 170)
CLARLEECSRFC (SEQ ID NO: 171)
CHNSSPMVGVTC (SEQ ID NO: 172)
CHVSPVQIKALC (SEQ ID NO: 173)
CAAPATSWFQYC (SEQ ID NO: 174)
CASKLHECSLRC (SEQ ID NO: 175)
CEPMDSNGIVQC (SEQ ID NO: 176)
CQYASAADEQRC (SEQ ID NO: 177)
CEYWDEPSLSWC (SEQ ID NO: 178)
CERECFQMLERC (SEQ ID NO: 179)
CGMSTDELDEIC (SEQ ID NO: 180)
CYVSPSTGLYSC (SEQ ID NO: 181)
CEARLVECSRLC (SEQ ID NO: 182)
CESRLSECSRMC (SEQ ID NO: 183)
CELKLQECARRC (SEQ ID NO: 184)
CELKLQEAARRC (SEQ ID NO: 185)

FIG. 1E

CLERLEECSRFC (SEQ ID NO: 186)
GGCESRLVECSRMC (SEQ ID NO: 187)
GGCETYMTYVYWLC (SEQ ID NO: 188)
EWLCESVGVGDWWSC (SEQ ID NO: 189)
YHPCEDRLVEGPWVCCRS (SEQ ID NO: 190)
WLLCNDQFRTCVDVCDNV (SEQ ID NO: 191)
IAECRGEWWELYHPCLAA (SEQ ID NO: 192)
TWYCEDTRTGWAWSCLEL (SEQ ID NO: 193)
QLDCTWLSSGELVWCSDW (SEQ ID NO: 194)
QFDCTWLSSGELVWCSDW (SEQ ID NO: 195)
CWPPVCEVSGICS (SEQ ID NO: 196)
CGCSLSPIQLQHLC (SEQ ID NO: 197)
CGCHVSPVQIKALC (SEQ ID NO: 198)
GCHVSPVQIKALC (SEQ ID NO: 199)
GTSCAAPATSWFQYCVLP (SEQ ID NO: 200)
RMDCASKLHECSLRCAYA (SEQ ID NO: 201)
GVVCEPMDSNGIVQCSMR (SEQ ID NO: 202)
IDVCQYASAADEQRCLRI (SEQ ID NO: 203)
NVLCEYWDEPSLSWCLSS (SEQ ID NO: 204)
CQCERECFQMLERC (SEQ ID NO: 205)
FCSCGMSTDELDEICAIW (SEQ ID NO: 206)
EEVCYVSPSTGLYSCYDQ (SEQ ID NO: 207)
LLDICELKLQECARRCN (SEQ ID NO: 208)
GGGLLDICELKLQECARRCN (SEQ ID NO: 209)
GRTGGGLLDICELKLQECARRCN (SEQ ID NO: 210)
LGIEGRTGGGLLDICELKLQECARRCN (SEQ ID NO: 211)
LLDICELKLQEAARRCN (SEQ ID NO: 212)
KLLDICELKLQEAARRCN (SEQ ID NO: 213)
EEKLRECAR (SEQ ID NO: 214)
EARLAECAR (SEQ ID NO: 215)
CMKLMECAR (SEQ ID NO: 216)
ELRLRECAH (SEQ ID NO: 217)
EAKLHECAR (SEQ ID NO: 218)
ELKLAECAR (SEQ ID NO: 219)
EARLEECAR (SEQ ID NO: 220)
EAKLRECAR (SEQ ID NO: 221)
ELRLAECAR (SEQ ID NO: 222)
ESRLAECAR (SEQ ID NO: 223)
EAKLVECAR (SEQ ID NO: 224)
ESRLRECAR (SEQ ID NO: 225)
EAKLAECAR (SEQ ID NO: 226)
QWRLEECAR (SEQ ID NO: 227)
QLRLEECAR (SEQ ID NO: 228)
ELRLEECAR (SEQ ID NO: 229)
EAKLLECAR (SEQ ID NO: 230)

FIG. 1F

EARAGVCAG (SEQ ID NO: 231)
EAKAGVCAG (SEQ ID NO: 232)
VARLEECAR (SEQ ID NO: 233)
ELKLDECAR (SEQ ID NO: 234)
EWRLQECAR (SEQ ID NO: 235)
EAKLSECAR (SEQ ID NO: 236)
EARLSECAR (SEQ ID NO: 237)
ELKLLECAR (SEQ ID NO: 238)
ELRLQECGR (SEQ ID NO: 239)
EQKLAECAR (SEQ ID NO: 240)
ELRLQECAR (SEQ ID NO: 241)
ELKLEECAR (SEQ ID NO: 242)
ESRLEECAR (SEQ ID NO: 243)
EATVQECAR (SEQ ID NO: 244)
ELKLQECAR (SEQ ID NO: 245)
YSRLEECGR (SEQ ID NO: 246)
ELRLRECAL (SEQ ID NO: 247)
EARLLECAR (SEQ ID NO: 248)
ESRLLECAR (SEQ ID NO: 249)
VLKLEECAR (SEQ ID NO: 250)
ESKLAECAR (SEQ ID NO: 251)
ESKLRECAR (SEQ ID NO: 252)
EYKLGECAR (SEQ ID NO: 253)
ESRLQECAR (SEQ ID NO: 254)
QARLAECAR (SEQ ID NO: 255)
ELKKQECAR (SEQ ID NO: 256)
ESRLSECAR (SEQ ID NO: 257)
EARLEECGR (SEQ ID NO: 258)
ESRLAECGR (SEQ ID NO: 259)
EWRLEECAR (SEQ ID NO: 260)
EARLSECGR (SEQ ID NO: 261)
AARLAECAR (SEQ ID NO: 262)
EWKLAECAR (SEQ ID NO: 263)
ESKLEECAR (SEQ ID NO: 264)
DVKLAECAR (SEQ ID NO: 265)
ELQLEECAR (SEQ ID NO: 266)
EYKLASCAR (SEQ ID NO: 267)
RLSICEEKLRECARGC (SEQ ID NO: 268)
PLTTCEARLAECARQL (SEQ ID NO: 269)
LALCMKLMECARRY (SEQ ID NO: 270)
ELVMCELRLRECAHRA (SEQ ID NO: 271)
PLARCEAKLHECARQL (SEQ ID NO: 272)
LLSVCELKLAECARSK (SEQ ID NO: 273)
RLEWCEARLEECARRC (SEQ ID NO: 274)
RLRVVEAKLRECARGR (SEQ ID NO: 275)

FIG. 1G

CVAHLELRLAECARQI (SEQ ID NO: 276)
HLARCESRLAECARQL (SEQ ID NO: 277)
RLALLEAKLVECARRL (SEQ ID NO: 278)
DLFSLESRLRECARRV (SEQ ID NO: 279)
AVPVLEAKLAECARRF (SEQ ID NO: 280)
YLQQLQWRLEECARGM (SEQ ID NO: 281)
YLELCQLRLEECARQFN (SEQ ID NO: 282)
ELHICELRLEECARGR (SEQ ID NO: 283)
RVARCELRLAECARKS (SEQ ID NO: 284)
YLEVLESRLAECARWK (SEQ ID NO: 285)
EAKLLECARAR (SEQ ID NO: 286)
ELSLCEARAGVCAGSVTK (SEQ ID NO: 287)
ELSLCEAKAGVCAGSVTK (SEQ ID NO: 288)
ALWQCVARLEECARSR (SEQ ID NO: 289)
CLKSCELKLDECARRM (SEQ ID NO: 290)
ALQTCEWRLQECARSR (SEQ ID NO: 291)
YISQCEAKLAECARLY (SEQ ID NO: 292)
ELSSCEAKLSECARRW (SEQ ID NO: 293)
ELSSCEARLSECARRW (SEQ ID NO: 294)
QLLQCELKLLECARQG (SEQ ID NO: 295)
ELLRCEARLAECARGC (SEQ ID NO: 296)
QLRQCELRLQECGRHGN (SEQ ID NO: 297)
PLTSCEQKLAECARRF (SEQ ID NO: 298)
LLGMCELRLQECARAK (SEQ ID NO: 299)
ELSRCELKLEECARGM (SEQ ID NO: 300)
DCRPCESRLEECARRL (SEQ ID NO: 301)
RLSVCEARLEECARQL (SEQ ID NO: 302)
PLKMCEATVQECARLI (SEQ ID NO: 303)
LLLFCEARLSECARHV (SEQ ID NO: 304)
SLSMCEARLAECARLL (SEQ ID NO: 305)
PLFSCELKLQECARRCN (SEQ ID NO: 306)
SLERCYSRLEECGRRI (SEQ ID NO: 307)
PLTSCELRLRECALRSN (SEQ ID NO: 308)
KLAACELKLAECARRW (SEQ ID NO: 309)
KLAACELRLAECARRW (SEQ ID NO: 310)
ALTRCELRLAECARKI (SEQ ID NO: 311)
LLQQCELKLAECARSI (SEQ ID NO: 312)
QLWQCEARLLECARRS (SEQ ID NO: 313)
RLRLCESRLLECARSL (SEQ ID NO: 314)
QLETCVLKLEECARRCN (SEQ ID NO: 315)
ALSQCELRLAECARSVTK (SEQ ID NO: 316)
ELKLAECARRS (SEQ ID NO: 317)
ALSRCESKLAECARRQ (SEQ ID NO: 318)
LMSTCESKLRECARSL (SEQ ID NO: 319)
SLQRCEYKLGECARSL (SEQ ID NO: 320)

FIG. 1H

RLELLESRLQECARQLN (SEQ ID NO: 321)
QMEWCQARLAECARCCN (SEQ ID NO: 322)
PLFSCELKKQECARRCN (SEQ ID NO: 323)
LLDKCESRLSECARRL (SEQ ID NO: 324)
LLARCEARLEECGRQC (SEQ ID NO: 325)
DLLYCESRLAECGRM (SEQ ID NO: 326)
ALQMCEWRLEECARRL (SEQ ID NO: 327)
LLTMCEARLSECGRRL (SEQ ID NO: 328)
ALWRCESRLAECARRS (SEQ ID NO: 329)
LLATCAARLAECARQL (SEQ ID NO: 330)
LQTCEWKLAECARSN (SEQ ID NO: 331)
PLRSCESKLEECARQL (SEQ ID NO: 332)
CLRALDVKLAECARHL (SEQ ID NO: 333)
RLKTLELQLEECARRS (SEQ ID NO: 334)
KLRDVELKLAECARRS (SEQ ID NO: 335)
SLQRCEYKLASCARSL (SEQ ID NO: 336)
RLARCELRLAECARKS (SEQ ID NO: 337)
DLWYLESKLEECARRCN (SEQ ID NO: 338)
DLWYLESKLEECARRANG (SEQ ID NO: 339)
DLWYLESKLEECARRCNG (SEQ ID NO: 340)
KQRELELKLAECARRS (SEQ ID NO: 341)
QMQEWCARLAECARCCN (SEQ ID NO: 342)
LLDICELKLQECARRAN (SEQ ID NO: 343)
AERKAEERRW (SEQ ID NO: 344)
AERYAEEREG (SEQ ID NO: 345)
AERMAEERRW (SEQ ID NO: 346)
AERKAEERRR (SEQ ID NO: 347)
AHRNAEERRW (SEQ ID NO: 348)
AERKSEDWRW (SEQ ID NO: 349)
AERKAEEKRR (SEQ ID NO: 350)
AERQAETRRW (SEQ ID NO: 351)
AERNAEERRW (SEQ ID NO: 352)
AERQAEERRW (SEQ ID NO: 353)
AERRAEERRW (SEQ ID NO: 354)
AERDAEQRRW (SEQ ID NO: 355)
AERIAEERRW (SEQ ID NO: 356)
AERSAEERRW (SEQ ID NO: 357)
AERKAEELRW (SEQ ID NO: 358)
AERKAEESRW (SEQ ID NO: 359)
EERKAEERRW (SEQ ID NO: 360)
ADGKAEERRW (SEQ ID NO: 361)
ADGKAEELRW (SEQ ID NO: 362)
ADGMPEERRW (SEQ ID NO: 363)
ADGEAEKRRW (SEQ ID NO: 364)
ADGNAEERRW (SEQ ID NO: 365)

FIG. 1I

ADGEAEKARW (SEQ ID NO: 366)
AEGEAEKARW (SEQ ID NO: 367)
GERKAEERRW (SEQ ID NO: 368)
AEREAEERRW (SEQ ID NO: 369)
ADGEAEARRW (SEQ ID NO: 370)
ADGRAEEARW (SEQ ID NO: 371)
AEGRAEEARW (SEQ ID NO: 372)
AEREAEKARW (SEQ ID NO: 373)
AERKAEEQRW (SEQ ID NO: 374)
AERDAEKRRW (SEQ ID NO: 375)
AEREAEKLRW (SEQ ID NO: 376)
MLAERKAEERRWFNTHGRE (SEQ ID NO: 377)
MLAERKAEERRWFNTHGREK (SEQ ID NO: 378)
GGGMLAERKAEERRWFNTHGRE (SEQ ID NO: 379)
CMLAERKAEERRWFNTHGRE (SEQ ID NO: 380)
CMLAERKAEERRWFNTHGREK (SEQ ID NO: 381)
MLAERYAEEREGFNMQWRE (SEQ ID NO: 382)
MLAERMAEERRWFRRMG (SEQ ID NO: 383)
IVAERKAEERRRLNTEGHE (SEQ ID NO: 384)
ILAHRNAEERRWFQKHGR (SEQ ID NO: 385)
MLAERKSEDWRWLKTHGRD (SEQ ID NO: 386)
MLAERKAEEKRRLKTQGRE (SEQ ID NO: 387)
ILAERQAETRRWMRNAGSVTK (SEQ ID NO: 388)
MLAERNAEERRWLKRQCG (SEQ ID NO: 389)
MLAERQAEERRWLKMHGGE (SEQ ID NO: 390)
MLAERRAEERRWLKTQGGD (SEQ ID NO: 391)
MLAERQAEERRWLKTQGRD (SEQ ID NO: 392)
MLAERKAEERRWFKTHGRE (SEQ ID NO: 393)
MLAERKAEERRWFNNQGRE (SEQ ID NO: 394)
MPAERDAEQRRWLKTHGRE (SEQ ID NO: 395)
ILAERIAEERRWLKTQGR (SEQ ID NO: 396)
MLAERKAEERRWLQTHGRE (SEQ ID NO: 397)
ILAERSAEERRWLKTQGRE (SEQ ID NO: 398)
LLAERKAEELRWLKTHGRE (SEQ ID NO: 399)
MLAERKAEERRWLQTHGRE (SEQ ID NO: 400)
MLAERNAEERRW (SEQ ID NO: 401)
MFAERKAEESRWLQSQGRE (SEQ ID NO: 402)
MLEERKAEERRWLKTHGR (SEQ ID NO: 403)
MLAERKAEERRWLKMQGRE (SEQ ID NO: 404)
MLAERNAEERRWFYTHGRE (SEQ ID NO: 405)
MLADGKAEERRWLKTHGLD (SEQ ID NO: 406)
MIADGKAEERRWLKTHGRD (SEQ ID NO: 407)
MLADGKAEELRWLKTQGSD (SEQ ID NO: 408)
MLAERNAEERRWLKTHGRD (SEQ ID NO: 409)
MLADGKAEELRWLKTQGRE (SEQ ID NO: 410)

FIG. 1J

ILADGKAEERRWLKTHGRD (SEQ ID NO: 411)
MLADGMPEERRWLQTHGRD (SEQ ID NO: 412)
MLADGEAEKRRWLNTHGRD (SEQ ID NO: 413)
MLADGNAEERRWLMTHGRD (SEQ ID NO: 414)
MLADGEAEKARWLKTQGRE (SEQ ID NO: 415)
MLAEGEAEKARWLKTQGRE (SEQ ID NO: 416)
MLADGKAEERRWLKTQGRE (SEQ ID NO: 417)
MLAERKAEERRWLSAHVRE (SEQ ID NO: 418)
LLGERKAEERRWYKTHARE (SEQ ID NO: 419)
MLAERKAEERRWLMTHGHD (SEQ ID NO: 420)
MLAERKAEERRWLKSQCLE (SEQ ID NO: 421)
LLAEREAEERRWFKTHGRE (SEQ ID NO: 422)
MLADGEAEARRWFNMHGRE (SEQ ID NO: 423)
MLADGRAEEARWLKTQGSE (SEQ ID NO: 424)
MLAEGRAEEARWLKTQGSE (SEQ ID NO: 425)
MLAEREAEKARWLKTQGRE (SEQ ID NO: 426)
MMAERKAEEQRWFDIHGRD (SEQ ID NO: 427)
LTAERDAEKRRWLLTHGGE (SEQ ID NO: 428)
MLAERQAEERRWLKSQRGE (SEQ ID NO: 429)
LLAERKAEERRWFATHGRD (SEQ ID NO: 430)
MLAEREAEKLRWLKSQERA (SEQ ID NO: 431)
MLAERKAEERRWLKTHGGE (SEQ ID NO: 432)
CTWTDLESVY (SEQ ID NO: 433)
HTTNEQFFMC (SEQ ID NO: 434)
DTWLELESRY (SEQ ID NO: 435)
HNSSPMVGVT (SEQ ID NO: 436)
DWQKTIPAYW (SEQ ID NO: 437)
RWGREGLVAALL (SEQ ID NO: 438)
WSGTRVWRCVVT (SEQ ID NO: 439)
MSLLSYLRS (SEQ ID NO: 440)
LDLLAI (SEQ ID NO: 441)
RIYGVK (SEQ ID NO: 442)
MIWHMFMSLLF (SEQ ID NO: 443)
FFWASWMHLLW (SEQ ID NO: 444)
FDDCWREREQFLFQAL (SEQ ID NO: 445)
CGRASECFRLLEM (SEQ ID NO: 446)
RECFQMLER (SEQ ID NO: 447)
CSIRWDFVPGYGLC (SEQ ID NO: 448)
WMQCWDSLSLCYDM (SEQ ID NO: 449)
ALLMCESKLAECARAR (SEQ ID NO: 450)
LAHCKKRKEECAAG (SEQ ID NO: 451)
SIDGVYLRTSRT (SEQ ID NO: 452)
SIDGVYLRTRSRTRY (SEQ ID NO: 453)
VRWLRGSTLRGLRDR (SEQ ID NO: 454)
DRGGGTVGVYWWESY (SEQ ID NO: 455)

FIG. 1K

VWGTVGTWLEY (SEQ ID NO: 456)
LMWVSAY (SEQ ID NO: 457)
RASDEYGALVRFCTNL (SEQ ID NO: 458)
NYWCDSNWVCEIA (SEQ ID NO: 459)
LAHCLLRLEECAAG (SEQ ID NO: 460)
LALCLARLRECAGG (SEQ ID NO: 461)
CESRLVECSRM (SEQ ID NO: 462)
LLDIAELKLQECARRCN (SEQ ID NO: 463)
KLLDIAELKLQECARRCN (SEQ ID NO: 464)
CSTGGGLTAERDAEKRRWLLTHGGE (SEQ ID NO: 465)
LTAERDAEKRRWLLTHGGEGG (SEQ ID NO: 466)
LTAERDAEKRRWLLTHGGEGGK (SEQ ID NO: 467)
LTAERDAEKRRWLLTHGGEGGGGG (SEQ ID NO: 468)
LTAERDAEKRRWLLTHGGEGGGGGK (SEQ ID NO: 469)
ESGWVW (SEQ ID NO: 470)
NSGWVW (SEQ ID NO: 471)
SGWVW (SEQ ID NO: 472)
PLGKCEATCREMARYFN (SEQ ID NO: 473)
SLQRCEYKLASVRGLCN (SEQ ID NO: 474)
DLWYLESKLEEAARRCNG (SEQ ID NO: 475)
PYMGTRSRAKLLRQQ (SEQ ID NO: 476)
RNAGERRWFKTQGWY (SEQ ID NO: 477)
MLAERNADDRRWFNTHGRD (SEQ ID NO: 478)
MMADGRLRNSVGLILWCD (SEQ ID NO: 479)
MLADGRLRNVVG (SEQ ID NO: 480)
LLADVRRRNGVGLLRMGRD (SEQ ID NO: 481)
MLADGRLRNFGG (SEQ ID NO: 482)
TYMTYVYWLC (SEQ ID NO: 483)
RFGERWGL (SEQ ID NO: 484)
HWLWWGWNF (SEQ ID NO: 485)
RECFQMLERC (SEQ ID NO: 486)
ILAHRNAKERRWFQKHGR (SEQ ID NO: 487)
CSTGGGLTAERDAEKRRWLLTHGGEK (SEQ ID NO: 489)
KGGGMLAERKAEERRWFNTHGRE (SEQ ID NO: 490)
KSTGGLTAERDAEKRRWLLTHGGE (SEQ ID NO: 491)
EQSNSGWVWVGGGGCKKKC (SEQ ID NO: 492)

AF16090 = GRTGGGLLDICELKLQECARRCN (SEQ ID NO.: 210)

COMPOUNDS HAVING AFFINITY FOR THE GRANULOCYTE-COLONY STIMULATING FACTOR RECEPTOR (G-CSFR) AND ASSOCIATED USES

TECHNICAL FIELD

The present invention relates generally to novel compounds that have affinity for the granulocyte-colony stimulating factor receptor (G-CSFR). More particularly, the invention relates to such compounds which act as G-CSF mimetics by activating or inactivating the G-CSFR, or by affecting ligand binding to G-CSFR. The invention additionally relates to methods of using the novel compounds and pharmaceutical compositions containing a compound of the invention as the active agent. The invention has application in the fields of biochemistry and medicinal chemistry and particularly provides G-CSF mimetics for use in the treatment of human disease.

BACKGROUND

Granulocyte-colony stimulating factor (G-CSF) is a hematopoietic growth factor that specifically stimulates proliferation and differentiation of cells of the neutrophilic lineage.

G-CSF is a cytokine that binds to and activates the granulocyte-colony stimulating factor receptor (G-CSFR). G-CSFR is expressed on the surface of mature neutrophils and cells committed to the neutrophilic lineage, with receptor density varying from 190 to more than 1400 sites per cell. The receptor is a member of the cytokine receptor superfamily; it contains a cytokine receptor-homologous domain responsible for G-CSF binding, an immunoglobulin-like domain, three fibronectin type III domains, a transmembrane region, and an intracellular domain. The observed affinity of G-CSF for its receptor is about 100 pM.

The complete G-CSF protein has become an important therapeutic agent in clinical indications involving depressed neutrophil counts. Such indications include chemotherapy-induced neutropenia, AIDS and community acquired pneumonia. Furthermore, G-CSF antagonists may be useful in the treatment of some diseases caused by an inappropriate or undesirable activation of G-CSFR.

There remains a need, however, for compounds that bind specifically to G-CSFR, both for studies of the important biological activities mediated by the receptor and for treatment of diseases, disorders and conditions that would benefit from activating or inactivating G-CSFR. The present invention provides such compounds, and also provides pharmaceutical compositions and methods for using the compounds as therapeutic agents.

SUMMARY OF THE INVENTION

In one embodiment, the invention provides compounds comprising a peptide chain that binds to G-CSFR. In one aspect, the peptide chain is approximately 10 to 40 amino acids in length and contains a sequence of amino acids of formula (I)

$$CX_1X_2X_3X_4X_5X_6X_7X_8C \text{ (SEQ ID NO: 1)} \quad (I)$$

wherein each amino acid is indicated by standard one-letter abbreviation, and wherein $X_1$ is A, N, S, F, D, G, L, T, E, V, P, Q, H, M or K; $X_2$ is M, G, R, H, D, I, V, A, S, E, N, F, Y, P, C, W or T; $X_3$ is E, V, W, F, M, A, N, S, L, T, Y, G or P; $X_4$ is V, I, G, Q, W, M, T, Y, L, P, D, C, E or A; $X_5$ is M, E, W, L, P, N, I, T, V, F, Y, Q, S, R, W, G, H or D; $X_6$ is H, A, W, Y, V, F, Q, M, N, E, S, D, P or G; $X_7$ is M, F, Y, V, N, L, H, D, S, W, G, Q, C or T; and $X_8$ is C, Y, R, I, K, W, L, E, M, H, A, T, F, D, P, G or Q.

In another aspect, the peptide chain is approximately 9 to 40 amino acids in length and contains a sequence of amino acids of formula (II)

$$X^I_1X^I_2X^I_3SGWVWX^I_4 \text{ (SEQ ID NO: 2)} \quad (II)$$

wherein each amino acid is indicated by the standard one-letter abbreviation, and wherein $X^I_1$ is S, Q, R, L or Y; $X^I_2$ is N, S, T, A or D; $X^I_3$ is E, D or N; and $X^I_4$ is L V, T, P or H.

In another aspect, the peptide chain is 6 to 40 amino acids in length and contains a sequence of amino acids of formula (III)

$$ERX^{II}_1X^{II}_2X^{II}_3C \text{ (SEQ ID NO: 3)} \quad (III)$$

wherein each amino acid is indicated by standard one-letter abbreviation, and wherein $X^{II}_1$ is D, L, S, G, E, A, K or Y; $X^{II}_2$ is W, Y, F, L or V; and $X^{II}_3$ is F, G, M or L.

In still another aspect, the peptide chain is approximately 9 to 40 amino acids in length and contains a sequence of amino acids of formula (IV)

$$X^{III}_1MVYX^{III}_2X^{III}_3PX^{III}_4W \text{ (SEQ ID NO: 4)} \quad (IV)$$

wherein each amino acid in indicated by standard one-letter abbreviation, and wherein $X^{III}_1$ is D or E; $X^{III}_2$ is A or T; $X^{III}_3$ is Y or V; and $X^{III}_4$ is P or Y.

In an additional aspect, the invention provides compounds comprising a peptide chain approximately 12 to 40 amino acids in length and contains a sequence of amino acids of formula (V)

$$CX^{IV}_1X^{IV}_2X^{IV}_3X^{IV}_4X^{IV}_5X^{IV}_6X^{IV}_7X^{IV}_8X^{IV}_9X^{IV}_{10}C \text{ (SEQ ID NO: 5)} \quad (V)$$

wherein each amino acid is indicated by standard one-letter abbreviation, and wherein $X^{IV}_1$ is E, G, P, N, R, T, W, S, L, H, A, Q or Y; $X^{IV}_2$ is S, T, E, A, D, G, W, P, L, N, V, Y, R or M; $X^{IV}_3$ is R, Y, V, Q, E, T, L, P, S, K, M, A or W; $X^{IV}_4$ is L, M, G, F, W, R, S, V, P, A, D, C or T; $X^{IV}_5$ is V, T, A, R, S, L, W, C, I, E, P, H, F, D or Q; $X^{IV}_6$ is E, Y, G, T, Q, M, S, N, A or P; $X^{IV}_7$ is C, V, D, G, L, W, E, V, I, S, M or A; $X^{IV}_8$ is S, Y, A, W, P, V, L, Q, G, K, F, I, E or D; $X^{IV}_9$ is R, W, M, D, H, V, G, A, Q, L, S, E or Y; $X^{IV}_{10}$ is M, L, I, S, V, P, W, F, T, Y, R, or Q.

In another aspect the peptide chain is approximately 9 to 40 amino acids in length and contains a sequence of amino acids of formula (VI)

$$X^V_1X^V_2X^V_3X^V_4X^V_5X^V_6CX^V_7X^V_8 \text{ (SEQ ID NO: 6)} \quad (VI)$$

wherein each amino acid is indicated by standard one-letter abbreviation, and wherein $X^V_1$ is E, C, Q, V, or Y; $X^V_2$ is E, A, L, M, S, W, or Q; $X^V_3$ is K, R or T; $X^V_4$ is L, A, or V; $X^V_5$ is R, A, M, H, E, V, L, G, D, Q, or S; $X^V_6$ is E or V; $X^V_7$ is A or G; $X^V_8$ is R H, G or L.

In a further aspect, the peptide chain is approximately 10 to 40 amino acids in length that binds to G-CSFR and contains a sequence of amino acids of formula (VII)

$$X^{VI}_1X^{VI}_2X^{VI}_3X^{VI}_4X^{VI}_5EX^{VI}_6X^{VI}_7X^{VI}_8X^{VI}_9 \text{ (SEQ ID NO: 7)} \quad (VII)$$

wherein each amino acid is indicated by standard one-letter abbreviation, and wherein $X^{VI}_5$ is A, E or G; $X^{VI}_2$ is E, H or D; $X^{VI}_3$ is R or G; $X^{VI}_4$ is K, Y, M, N, Q, R, D, I, S or E;

$X^{VI}_5$ is A, S or P; $X^{VI}_6$ is E, D, T, Q, K or A: $X^{VI}_7$ is R, W, K, L, S, A or Q; $X^{VI}_8$ is R or E; and $X^{VI}_9$ is W, G, or R.

In a final aspect, the invention also provides peptides that, while not necessarily corresponding to one of the above-defined formulas, bind to G-CSFR.

In some contexts, the compounds of the invention are preferably in the form of a dimer. It is also preferred, in some contexts, that the compounds of the invention include a peptide wherein the N-terminus of the peptide is coupled to a polyethylene glycol molecule. In some contexts, it is preferred that the compounds of the invention include a peptide wherein the N-terminus of the peptide is acetylated. In addition, it is preferred, in some contexts, that the compounds of the invention include a peptide wherein the C-terminus of the peptide is amidated.

The invention also provides a pharmaceutical composition that comprises a therapeutically effective amount of a compound of the invention in combination with a pharmaceutically acceptable carrier, as well as a method for treating a patient who would benefit from a G-CSFR modulator, the method comprising administering to the patient a therapeutically effective amount of a compound of the present invention.

BRIEF DESCRIPTION OF THE DRAWINGS

FIGS. 1A, 1B, 1C, 1D, 1E, 1F, 1G, 1H, 1I, 1J and 1K provide the sequences of representative peptide chains contained within the compounds of the invention.

DETAILED DESCRIPTION OF THE INVENTION

I. Definitions and Overview

Figure 2:
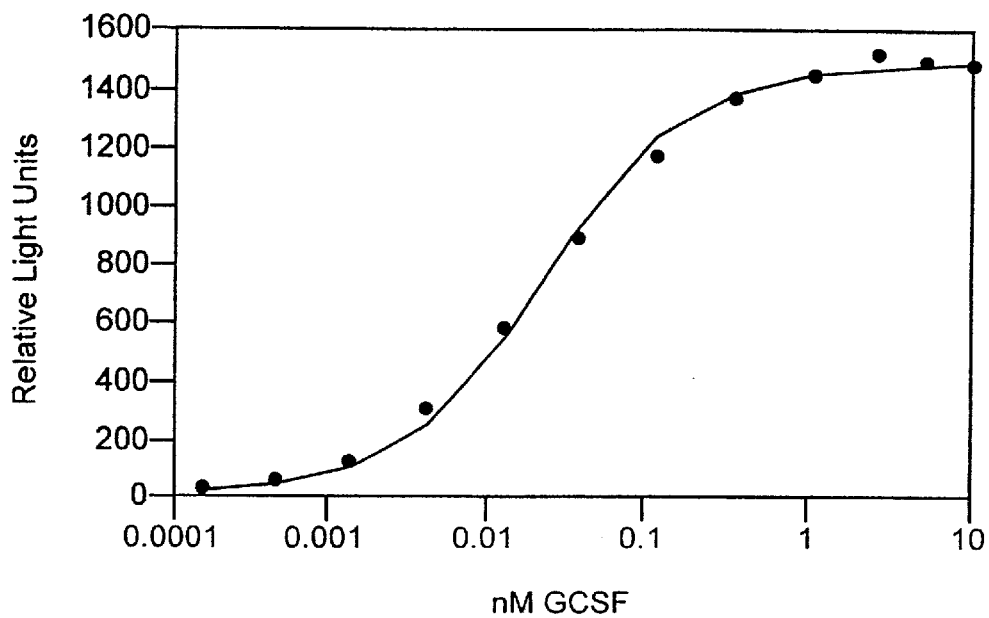
FIGS. 2, 3, 4, 5, 6, 7, 8, 9A, 9B 10A, 10B and 11 are graphs showing the results of various assays described in Examples.

It is to be understood that unless otherwise indicated, this invention is not limited to specific peptide sequences, molecular structures, pharmaceutical compositions, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a novel compound" in a pharmaceutical composition means that more than one of the novel compounds can be present in the composition, reference to "a pharmaceutically acceptable carrier" includes combinations of such carriers, and the like.

In this specification and in the claims that follow, reference will be made to a number of terms which shall be defined to have the following meanings:

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. In addition, "1-Nal" is used to refer to 1-naphthylalanine, the "2-Nal" is used to refer to 2-naphthylalanine.

Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for compounds of the present invention. Examples of unconventional amino acids include: β-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

"Peptide" or "polypeptide" refers to a polymer in which the monomers are alpha amino acids joined together through amide bonds. Peptides are two or often more amino acid monomers long. One or more of the peptide chains disclosed herein may appear in the compounds of the present. It is also contemplated that the peptide chains disclosed herein represent only a portion of the overall peptide included in the compound.

The term "dimer" as in a peptide "dimer" refers to a compound in which two peptide chains are linked; generally, although not necessarily, the two peptide chains will be identical and are linked through a linking moiety covalently bound to the carboxyl terminus of each chain.

The term "agonist" is used herein to refer to a ligand that binds to a receptor and activates the receptor.

The term "antagonist" is used herein to refer to a ligand that binds to a receptor without activating the receptor. Antagonists are either competitive antagonists or noncompetitive antagonists. A "competitive antagonist" blocks the receptor site that is specific for the agonist. A "noncompetitive antagonist" inactivates or otherwise affects the functioning of the receptor by interacting with a site other than the agonist binding site.

The term "modulator" as in a "G-CSFR-modulator" refers to a compound that is either an agonist or antagonist of the G-CSFR.

"Pharmaceutically or therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to either at least partially activate or at least partially inactivate G-CSFR and, thus, alleviate the symptoms associated with an undesired neutrophil count in vivo.

An "optimal neutrophil count" refers to a quantity of neutrophils in a patient that is determined by a clinician to be optimal for that patient in light of the patient's disease state, condition, etc.

An "undesired neutrophil count" refers to a quantity of neutrophils in a patient that is determined by a clinician to be not optimal for that patient in light of the patient's disease state, condition, etc. Thus, an undesired neutrophil count may be depressed, elevated or even equal to the expected neutrophil count so long as the clinician determines that the actual count is not optimal for the patient. The compounds of the present invention are intended to, inter alia, provide the clinician with compounds that, when administered to a patient, bring that patient's neutrophil count closer to an optimal neutrophil count.

The term "treat" as in "treat a disease" is intended to include any means of treating a disease in a mammal, including (1) preventing the disease, i.e., avoiding any clinical symptoms of the disease, (2) inhibiting the disease, that is, arresting the development or progression of clinical symptoms, and/or (3) relieving the disease, i.e., causing regression of clinical symptoms.

"Optional" or "optionally" means that the subsequently described circumstance may or may not occur, so that the description includes instances where the circumstance occurs and instances where it does not.

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained.

II. The Compounds

A. Compounds of Formula (I):

In a first embodiment, the invention provides compounds comprising a peptide chain that binds to G-CSFR, wherein the compounds comprise a peptide chain approximately 10 to 40 amino acids in length that binds to G-CSFR and contains a sequence of amino acids of formula (I)

$$CX_1X_2X_3X_4X_5X_6X_7X_8C \text{ (SEQ ID NO: 1)} \quad (I)$$

wherein each amino acid is indicated by standard one-letter abbreviation, and wherein $X_1$ is A, N, S, F, D, G, L, T, E, V, P, Q, H, M or K; $X_2$ is M, G, R, H, D, I, V, A, S, E, N, F, Y, P, C, W or T; $X_3$ is E, V, W, F, M, A, N, S, L, T, Y, G or P; $X_4$ is V, I, G, Q, W, M, T, Y, L, P, D, C, E or A; $X_5$ is M, E, W, L, P, N, I, T, V, F, Y, Q, S, R, W, G, H or D; $X_6$ is H, A, W, Y, V, F, Q, M, N, E, S, D, P or G; $X_7$ is M, F, Y, V, N, L, H, D, S, W, G, Q, C or T; and $X_8$ is C, Y, R, I, K, W, L, E, M, H, A, T, F, D, P, G or Q.

Preferably $X_1$ is D or P; $X_2$ is D or P; $X_3$ is E or W; $X_4$ is V, I or Y; $X_5$ is M or L; $X_6$ is W, Y or F; $X_7$ is M, Y or D; and $X_8$ is C or M. Examples of particularly preferred sequences satisfying formula (I) include, but are not limited to, the following:

CAGEVMHMCC (SEQ ID NO: 8);
CNREIEAMCC (SEQ ID NO: 9);
CADEVMHFCC (SEQ ID NO: 10);
CNREIMWMCC (SEQ ID NO: 11);
CSHEVWWYCC (SEQ ID NO: 12);
CSREVLYYCC (SEQ ID NO: 13);
CFIEGPWVCC (SEQ ID NO: 14);
CFVEGNWYCC (SEQ ID NO: 15);
CAAEVMVNCC (SEQ ID NO: 16);
CSDEVIFYCC (SEQ ID NO: 17);
CDREIMWFCC (SEQ ID NO: 18);
CAHEVMWMCC (SEQ ID NO: 19);
CGSEVTFMCC (SEQ ID NO: 20);
CLEEIMWLCC (SEQ ID NO: 21);
CAREVLAMCC (SEQ ID NO: 22);
CSVEVMQMCC (SEQ ID NO: 23);
CTNVQLMHYC (SEQ ID NO: 24);
CDVWQLFDRC (SEQ ID NO: 25);
CSFVQLNSIC (SEQ ID NO: 26);
CDYWQWFDKC (SEQ ID NO: 27);
CESFWVELWC (SEQ ID NO: 28);
CVPWMFYDLC (SEQ ID NO: 29);
CDPWMFYDLC (SEQ ID NO: 30);
CDPWVLFDEC (SEQ ID NO: 31);
CDHWTYFDMC (SEQ ID NO: 32);
CVVWTLYDKC (SEQ ID NO: 33);
CPDWYQSYMC (SEQ ID NO: 34);
CPDWYSYYMC (SEQ ID NO: 35);
CPEWYTDVMC (SEQ ID NO: 36);
CPDWYLDYMC (SEQ ID NO: 37);
CPEWYLDYMC (SEQ ID NO: 38);
CPDWYLPYMC (SEQ ID NO: 39);
CPEWYLPYMC (SEQ ID NO: 40);
CQDWWVELWC (SEQ ID NO: 41);
CPDWYLPWMC (SEQ ID NO: 42);
CACMLRVVHC (SEQ ID NO: 43);
CQRAGYMLAC (SEQ ID NO: 44);
CHANPVWGEC (SEQ ID NO: 45);
CFWSDWGQTC (SEQ ID NO: 46);
CPHWTSYYMC (SEQ ID NO: 47);
CETLCGACFC (SEQ ID NO: 48);
CATTINDTLC (SEQ ID NO: 49);
CLNYPHPVFC (SEQ ID NO: 50);
CMDGEMAVDC (SEQ ID NO: 51);
CNMGWMSWPC (SEQ ID NO: 52)
CETYADWLGC (SEQ ID NO: 53);
CDPWMFFDMC (SEQ ID NO: 54);
CDPWIWYDLC (SEQ ID NO: 55);
CDPWIMYDRC (SEQ ID NO: 56);
CDPWVFFDIC (SEQ ID NO: 57);
CDPWTYYDLC (SEQ ID NO: 58);
CDPWIFYDRC (SEQ ID NO: 59);
CDPWLFYDLC (SEQ ID NO: 60);
CDPWVWYDLC (SEQ ID NO: 61);
CDPWIFFDRC (SEQ ID NO: 62);
CDPWMFFDQC (SEQ ID NO: 63);
CDPWLWYDRC (SEQ ID NO: 64);
CDVWVWYDQC (SEQ ID NO: 65);
CDPWIYYDLC (SEQ ID NO: 66);
CVPWTLFDLC (SEQ ID NO: 67);
CPAWYLEYMC (SEQ ID NO: 68);
CPDWYLEYMC (SEQ ID NO: 69);
CKYWQWFDKC (SEQ ID NO: 70); and
CDHWMWYDKC (SEQ ID NO: 71).

Other preferred formula (I) sequences include, but are not limited to the following:

GCNREIEAMCCG (SEQ ID NO: 72);
GCPEWYTDVMCG (SEQ ID NO: 73);
NWYCMDGEMAVDCEAT (SEQ ID NO: 74);
WQSCNMGWMSWPCYFV (SEQ ID NO: 75);
HELCETYADWLGCVEW (SEQ ID NO: 76);
PCDPWMFFDMCERW (SEQ ID NO: 77);
LRGCDPWIWYDLCPAV (SEQ ID NO: 78);
GYLCDPWIFYDRCLGF (SEQ ID NO: 79);
RFACDPWVFFDICGYW (SEQ ID NO: 80);
GYWCDPWTYYDLCLTA (SEQ ID NO: 81);
MWTCDPWIFYDRCFLN (SEQ ID NO: 82);
GSSCDPWLFYDLCLLD (SEQ ID NO: 83);
GGGCDPWVWYDLCWCD (SEQ ID NO: 84);
YTSCDPWIFFDRCMSV (SEQ ID NO: 85);
DPYCDPWMFFDQCAYL (SEQ ID NO: 86);
REFCDPWLWYDRCL (SEQ ID NO: 87);
NTGCDVWVWYDQCFAM (SEQ ID NO: 88);
LVFCDPWIYYDLCMDT (SEQ ID NO: 89);

GCSFVQLNSICG (SEQ ID NO: 90);
GCPAWYLEYMCG (SEQ ID NO: 91);
GCPDWYLEYMCG (SEQ ID NO: 92);
GCKYWQWFDKCG (SEQ ID NO: 93); and
GCDHWMWYDKCG (SEQ ID NO: 94).

B. Compounds of Formula (II):

In another aspect, compounds are provided comprising a peptide chain approximately 9 to 40 amino acids in length that binds to G-CSFR and contains a sequence of amino acids of formula (II)

$$X'_1X'_2X'_3SGWVWX'_4 \text{ (SEQ ID NO: 2)} \tag{II}$$

wherein each amino acid is indicated by the standard one-letter abbreviation, and wherein $X'_1$ is S, Q, R, L or Y; $X'_2$ is N, S, T, A or D; $X'_3$ is E, D or N; and $X'_4$ is L V, T, P or H.

Preferably $X'_1$ is S or Q; $X'_2$ is S; $X'_3$ is N; and $X'_4$ is V.

Examples of particularly preferred sequences satisfying formula (II) include, but are not limited to, the following:

SNESGWVWL (SEQ ID NO: 95);
QSNSGWVWV (SEQ ID NO: 96);
RTESGWVWT (SEQ ID NO: 97);
RANSGWVWV (SEQ ID NO: 98);
YDNSGWVWH (SEQ ID NO: 99); and
LSDSGWVWVP (SEQ ID NO: 100).

Other preferred formula (II) sequences include, but are not limited to, the following:

EQSNSGWVWVGGGGC (SEQ ID NO: 101);
CEQSNSGWVWV (SEQ ID NO: 102);
EQSNSGWVWVGGGGCKKK (SEQ ID NO: 103);
EQSNSGWVWVGKKKC (SEQ ID NO: 104);
EQSNSGWVWVGKKK (SEQ ID NO: 105);
KKKEQSNSGWVWV (SEQ ID NO: 106);
EQSNSGWVWVGKKKSKKK (SEQ ID NO: 107);
EQSNSGWVWVGGCKKK (SEQ ID NO: 108);
EQSNSGWVWVGGGGGGCKKK (SEQ ID NO: 109);
SNESGWVWLP (SEQ ID NO: 110);
EQSNSGWVWV (SEQ ID NO: 111);
SRTESGWVWT (SEQ ID NO: 112);
QRANSGWVWV (SEQ ID NO: 113);
DYDNSGWVWH (SEQ ID NO: 114);
EQSNSGWVWVGKKKK (SEQ ID NO: 115);
EQSNSGWVWVGGGGSKKK (SEQ ID NO: 116);
EQSNSGWVWVGGGGS (SEQ ID NO: 117);
EQSNSGWVWVGGGGSEQSNSGWVWVGGGGS (SEQ ID NO: 118);
RYQSFELSDSGWVWVPVARH (SEQ ID NO: 119); and
EQSNSGWVWVGGGGCKKKC (SEQ ID NO: 492).

C. Compounds of Formula (III):

In another aspect, the invention provides compounds comprising a peptide chain approximately 6 to 40 amino acids in length that binds to G-CSFR and contains a sequence of amino acids of formula (III)

$$ERX''_1X''_2X''_3C \text{ (SEQ ID NO: 3)} \tag{III}$$

wherein each amino acid is indicated by standard one-letter abbreviation, and wherein $X''_1$ is D, L, S,G, E, A, K or Y; $X''_2$ is W, Y, F, L or V; and $X''_3$ is F, G, M or L.

Preferably, $X''_1$ is D or L; $X''_2$ is W; and $X''_3$ is F.

Examples of particularly preferred sequences satisfying formula (III) include, but are not limited to, the following:

ERDWFC (SEQ ID NO: 120);
ERDWGC (SEQ ID NO: 121);
ERLWFC (SEQ ID NO: 122);
ERSYFC (SEQ ID NO: 123);
ERGWFC (SEQ ID NO: 124);
EREWFC (SEQ ID NO: 125);
ERAWFC (SEQ ID NO: 126);
ERLYFC (SEQ ID NO: 127);
ERYFMC (SEQ ID NO: 128);
ERLFLC (SEQ ID NO: 129);
ERALMC (SEQ ID NO: 130);
ERDVMC (SEQ ID NO: 131); and
ERKWFC (SEQ ID NO: 132).

Particulary preferred compounds are of the formula:

ETWGERDWFC (SEQ ID NO: 133);
ETWGERDWGC (SEQ ID NO: 134);
STAERLWFCG (SEQ ID NO: 135);
YETAERSYFC (SEQ ID NO: 136);
ADNAERGWFC (SEQ ID NO: 137);
QSNSEREWFC (SEQ ID NO: 138);
STSERAWFCG (SEQ ID NO: 139);
ASWSERGWFC (SEQ ID NO: 140);
ELSSEREWFC (SEQ ID NO: 141);
DMQGERGWFC (SEQ ID NO: 142);
SSSERAWFCG (SEQ ID NO: 143);
GNMRERLYFC (SEQ ID NO: 144);
QPNRERYFMC (SEQ ID NO: 145);
SVTRERLFLC (SEQ ID NO: 146);
IPLSERALMCSSWNC (SEQ ID NO: 147);
WARSERDVMCLSYVC (SEQ ID NO: 148);
QSNSEREWFCG (SEQ ID NO: 149);
QSNSEREWFCGGGGS (SEQ ID NO: 150);
NLEEALAQERLWFCRSGNC (SEQ ID NO: 151); and
NLESYEMEERKWFCKMFSC (SEQ ID NO: 152).

D. Compounds of Formula (IV):

In another aspect, compounds are provided comprising a peptide chain approximately 9 to 40 amino acids in length that binds to G-CSFR and contains a sequence of amino acids of formula (IV):

$$X'''_1MVYX'''_2X'''_3PX'''_4W \text{ (SEQ ID NO: 4)} \tag{IV}$$

wherein each amino acid in indicated by standard one-letter abbreviation, and wherein $X'''_1$ is D or E; $X'''_2$ is A or T; $X'''_3$ is Y or V; and $X'''_4$ is P or Y.

Examples of particularly preferred sequences satisfying formula (IV) include, but are not limited to, the following:

DMVYAYPPW (SEQ ID NO: 153); and
EMVYTVPYW (SEQ ID NO: 154).

Other preferred formula (IV) sequences include, but are not limited to, the following:

DMVYAYPPWS (SEQ ID NO: 155); and
DEMVYTVPYW (SEQ ID NO: 156).

E. Compounds of Formula (V):

In another aspect, compounds are provided comprising a peptide chain approximately 12 to 40 amino acids in length that binds to G-CSFR and contains a sequence of amino acids of formula (V):

$$CX^{IV}_1X^{IV}_2X^{IV}_3X^{IV}_4X^{IV}_5X^{IV}_6X^{IV}_7X^{IV}_8X^{IV}_9X^{IV}_{10}C \text{ (SEQ ID NO: 5)} \quad \text{(V)}$$

wherein each amino acid is indicated by standard one-letter abbreviation, and wherein $X^{IV}_1$ is E, G, P, N, R, T, W, S, L, H, A, Q or Y; $X^{IV}_2$ is S, T, E, A, D, G, W, P, L, N, V, Y, R or M; $X^{IV}_3$ is R, Y, V, Q, E, T, L, P, S, K, M, A or W; $X^{IV}_4$ is L, M, G, F, W, R, S, V, P, A, D, C or T; $X^{IV}_5$ is V, T, A, R, S, L, W, C, I, E, P, H, F, D or Q; $X^{IV}_6$ is E, Y, G, T, Q, M, S, N, A or P; $X^{IV}_7$ is C, V, D, G, L, W, E, V, I, S, M or A; $X^{IV}_8$ is S, Y, A, W, P, V, L, Q, G, K, F, I, E or D; $X^{IV}_9$ is R, W, M, D, H, V, G, A, Q, L, S, E or Y; $X^{IV}_{10}$ is M, L, I, S, V, P, W, F, T, Y, R, or Q.

Preferably $X^{IV}_1$ is E; $X^{IV}_2$ is S or A; $X^{IV}_3$ is R; $X^{IV}_4$ is L; $X^{IV}_5$ is V or S; $X^{IV}_6$ is E; $X^{IV}_7$ is C; $X^{IV}_8$ is S; $X^{IV}_9$ is R; and $X^{IV}_{10}$ is L.

Examples of particularly preferred sequences satisfying formula (V) include, but are not limited to, the following:

CESRLVECSRMC (SEQ ID NO: 157);
CETYMTYVYWLC (SEQ ID NO: 158);
CGERLAECARLC (SEQ ID NO: 159);
CESRLRECSMLC (SEQ ID NO: 160);
CEARLSECSRIC (SEQ ID NO: 161);
CPARLLECSRMC (SEQ ID NO: 162);
CESVGVGDWWSC (SEQ ID NO: 163);
CEDRLVEGPWVC (SEQ ID NO: 164);
CNDQFRTCVDVC (SEQ ID NO: 165);
CRGEWWELYHPC (SEQ ID NO: 166);
CEDTRTGWAWSC (SEQ ID NO: 167);
CTWLSSGELVWC (SEQ ID NO: 168);
CWPPVCEVSGIC (SEQ ID NO: 169);
CSLSPIQLQHLC (SEQ ID NO: 170);
CLARLEECSRFC (SEQ ID NO: 171);
CHNSSPMVGVTC (SEQ ID NO: 172);
CHVSPVQIKALC (SEQ ID NO: 173);
CAAPATSWFQYC (SEQ ID NO: 174);
CASKLHECSLRC (SEQ ID NO: 175);
CEPMDSNGIVQC (SEQ ID NO: 176);
CQYASAADEQRC (SEQ ID NO: 177);
CEYWDEPSLSWC (SEQ ID NO: 178);
CERECFQMLERC (SEQ ID NO: 179);
CGMSTDELDEIC (SEQ ID NO: 180);
CYVSPSTGLYSC (SEQ ID NO: 181);
CEARLVECSRLC (SEQ ID NO: 182);
CESRLSECSRMC (SEQ ID NO: 183);
CELKLQECARRC (SEQ ID NO: 184);
CELKLQEAARRC (SEQ ID NO: 185); and
CLERLEECSRFC (SEQ ID NO: 186).

Other preferred formula (V) sequences include but are not limited to, the following:

GGCESRLVECSRMC (SEQ ID NO: 187);
GGCETYMTYVYWLC (SEQ ID NO: 188);
EWLCESVGVGDWWSC (SEQ ID NO: 189);
YHPCEDRLVEGPWVCCRS (SEQ ID NO: 190);
WLLCNDQFRTCVDVCDNV (SEQ ID NO: 191);
IAECRGEWWELYHPCLAA (SEQ ID NO: 192);
TWYCEDTRTGWAWSCLEL (SEQ ID NO: 193);
QLDCTWLSSGELVWCSDW (SEQ ID NO: 194);
QFDCTWLSSGELVWCSDW (SEQ ID NO: 195);
CWPPVCEVSGICS (SEQ ID NO: 196);
CGCSLSPIQLQHLC (SEQ ID NO: 197);
CGCHVSPVQIKALC (SEQ ID NO: 198);
GCHVSPVQIKALC (SEQ ID NO: 199);
GTSCAAPATSWFQYCVLP (SEQ ID NO: 200);
RMDCASKLHECSLRCAYA (SEQ ID NO: 201);
GVVCEPMDSNGIVQCSMR (SEQ ID NO: 202);
IDVCQYASAADEQRCLRI (SEQ ID NO: 203);
NVLCEYWDEPSLSWCLSS (SEQ ID NO: 204);
CQCERECFQMLERC (SEQ ID NO: 205);
FCSCGMSTDELDEICAIW (SEQ ID NO: 206);
EEVCYVSPSTGLYSCYDQ (SEQ ID NO: 207);
LLDICELKLQECARRCN (SEQ ID NO: 208);
GGGLLDICELKLQECARRCN (SEQ ID NO: 209);
GRTGGGLLDICELKLQECARRCN (SEQ ID NO: 210);
LGIEGRTGGGLLDICELKLQECARRCN (SEQ ID NO: 211);
LLDICELKLQEAARRCN (SEQ ID NO: 212); and
KLLDICELKLQEAARRCN (SEQ ID NO: 213).

Particularly preferred formula (V) sequences are selected from the group consisting of:

LLDICELKLQECARRCN (SEQ ID NO: 208);
GGGLLDICELKLQECARRCN (SEQ ID NO: 209);
GRTGGGLLDICELKLQECARRCN (SEQ ID NO: 210);
LGIEGRTGGGLLDICELKLQECARRCN (SEQ ID NO: 211);
LLDICELKLQEAARRCN (SEQ ID NO: 212); and
KLLDICELKLQEAARRCN (SEQ ID NO: 213).

F. Compounds of Formula (VI):

In another aspect, compounds are provided comprising a peptide chain approximately 9 to 40 amino acids in length that binds to G-CSFR and contains a sequence of amino acids of formula (VI):

$$X^V_1X^V_2X^V_3X^V_4X^V_5X^V_6CX^V_7X^V_8 \text{ (SEQ ID NO: 6)} \quad \text{(VI)}$$

wherein each amino acid is indicated by standard one-letter abbreviation, and wherein $X^V_1$ is E, C, Q, V, or Y; $X^V_2$ is E, A, L, M, S, W, or Q; $X^V_3$ is K, R or T; $X^V_4$ is L, A, or V; $X^V_5$ is R, A, M, H, E, V, L, G, D, Q, or S; $X^V_6$ is E or V; $X^V_7$ is A or G; $X^V_8$ is R, H, G or L.

Preferably $X^V_1$ is E; $X^V_2$ is A or L; $X^V_3$ is K or R; $X^V_4$ is L; $X^V_6$ is E; $X^V_7$ is A; and $X^V_8$ is R.

Examples of particularly preferred sequences satisfying formula (VI) include, but are not limited to, the following:

EEKLRECAR (SEQ ID NO: 214);
EARLAECAR (SEQ ID NO: 215);
CMKLMECAR (SEQ ID NO: 216);
ELRLRECAH (SEQ ID NO: 217);
EAKLHECAR (SEQ ID NO: 218);
ELKLAECAR (SEQ ID NO: 219);
EARLEECAR (SEQ ID NO: 220);
EAKLRECAR (SEQ ID NO: 221);
ELRLAECAR (SEQ ID NO: 222);
ESRLAECAR (SEQ ID NO: 223);
EAKLVECAR (SEQ ID NO: 224);
ESRLRECAR (SEQ ID NO: 225);
EAKLAECAR (SEQ ID NO: 226);
QWRLEECAR (SEQ ID NO: 227);
QLRLEECAR (SEQ ID NO: 228);
ELRLEECAR (SEQ ID NO: 229);

EAKLLECAR (SEQ ID NO: 230);
EARAGVCAG (SEQ ID NO: 231);
EAKAGVCAG (SEQ ID NO: 232);
VARLEECAR (SEQ ID NO: 233);
ELKLDECAR (SEQ ID NO: 234);
EWRLQECAR (SEQ ID NO: 235);
EAKLSECAR (SEQ ID NO: 236);
EARLSECAR (SEQ ID NO: 237);
ELKLLECAR (SEQ ID NO: 238);
ELRLQECGR (SEQ ID NO: 239);
EQKLAECAR (SEQ ID NO: 240);
ELRLQECAR (SEQ ID NO: 241);
ELKLEECAR (SEQ ID NO: 242);
ESRLEECAR (SEQ ID NO: 243);
EATVQECAR (SEQ ID NO: 244);
ELKLQECAR (SEQ ID NO: 245);
YSRLEECGR (SEQ ID NO: 246);
ELRLRECAL (SEQ ID NO: 247);
EARLLECAR (SEQ ID NO: 248);
ESRLLECAR (SEQ ID NO: 249);
VLKLEECAR (SEQ ID NO: 250);
ESKLAECAR (SEQ ID NO: 251);
ESKLRECAR (SEQ ID NO: 252);
EYKLGECAR (SEQ ID NO: 253);
ESRLQECAR (SEQ ID NO: 254);
QARLAECAR (SEQ ID NO: 255);
ELKKQECAR (SEQ ID NO: 256);
ESRLSECAR (SEQ ID NO: 257);
EARLEECGR (SEQ ID NO: 258);
ESRLAECGR (SEQ ID NO: 259);
EWRLEECAR (SEQ ID NO: 260);
EARLSECGR (SEQ ID NO: 261);
AARLAECAR (SEQ ID NO: 262);
EWKLAECAR (SEQ ID NO: 263);
ESKLEECAR (SEQ ID NO: 264);
DVKLAECAR (SEQ ID NO: 265);
ELQLEECAR (SEQ ID NO: 266); and
EYKLASCAR (SEQ ID NO: 267).

Other preferred formula (VI) sequences include but are not limited to, the following:
RLSICEEKLRECARGC (SEQ ID NO: 268);
PLTTCEARLAECARQL (SEQ ID NO: 269);
LALCMKLMECARRY (SEQ ID NO: 270);
ELVMCELRLRECAHRA (SEQ ID NO: 271);
PLARCEAKLHECARQL (SEQ ID NO: 272);
LLSVCELKLAECARSK (SEQ ID NO: 273);
RLEWCEARLEECARRC (SEQ ID NO: 274);
RLRVVEAKLRECARGR (SEQ ID NO: 275);
CVAHLELRLAECARQI (SEQ ID NO: 276);
HLARCESRLAECARQL (SEQ ID NO: 277);
RLALLEAKLVECARRL (SEQ ID NO: 278);
DLFSLESRLRECARRV (SEQ ID NO: 279);
AVPVLEAKLAECARRF (SEQ ID NO: 280);
YLQQLQWRLEECARGM (SEQ ID NO: 281);
YLELCQLRLEECARQFN (SEQ ID NO: 282);
ELHICELRLEECARGR (SEQ ID NO: 283);
RVARCELRLAECARKS (SEQ ID NO: 284);
YLEVLESRLAECARWK (SEQ ID NO: 285);
EAKLLECARAR (SEQ ID NO: 286);
ELSLCEARAGVCAGSVTK (SEQ ID NO: 287);
ELSLCEAKAGVCAGSVTK (SEQ ID NO: 288);
ALWQCVARLEECARSR (SEQ ID NO: 289);
CLKSCELKLDECARRM (SEQ ID NO: 290);
ALQTCEWRLQECARSR (SEQ ID NO: 291);
YISQCEAKLAECARLY (SEQ ID NO: 292);
ELSSCEAKLSECARRW (SEQ ID NO: 293);
ELSSCEARLSECARRW (SEQ ID NO: 294);
QLLQCELKLLECARQG (SEQ ID NO: 295);
ELLRCEARLAECARGC (SEQ ID NO: 296);
QLRQCELRLQECGRHGN (SEQ ID NO: 297);
PLTSCEQKLAECARRF (SEQ ID NO: 298);
LLGMCELRLQECARAK (SEQ ID NO: 299);
ELSRCELKLEECARGM (SEQ ID NO: 300);
DCRPCESRLEECARRL (SEQ ID NO: 301);
RLSVCEARLEECARQL (SEQ ID NO: 302);
PLKMCEATVQECARLI (SEQ ID NO: 303);
LLLFCEARLSECARHV (SEQ ID NO: 304);
SLSMCEARLAECARLL (SEQ ID NO: 305);
PLFSCELKLQECARRCN (SEQ ID NO: 306);
SLERCYSRLEECGRRI (SEQ ID NO: 307);
PLTSCELRLRECALRSN (SEQ ID NO: 308);
KLAACELKLAECARRW (SEQ ID NO: 309);
KLAACELRLAECARRW (SEQ ID NO: 310);
ALTRCELRLAECARKI (SEQ ID NO: 311);
LLQQCELKLAECARSI (SEQ ID NO: 312);
QLWQCEARLLECARRS (SEQ ID NO: 313);
RLRLCESRLLECARSL (SEQ ID NO: 314);
QLETCVLKLEECARRCN (SEQ ID NO: 315);
ALSQCELRLAECARSVTK (SEQ ID NO: 316);
ELKLAECARRS (SEQ ID NO: 317);
ALSRCESKLAECARRQ (SEQ ID NO: 318);
LMSTCESKLRECARSL (SEQ ID NO: 319);
SLQRCEYKLGECARSL (SEQ ID NO: 320);
RLELLESRLQECARQLN (SEQ ID NO: 321);
QMEWCQARLAECARCCN (SEQ ID NO: 322);
PLFSCELKKQECARRCN (SEQ ID NO: 323);
LLDKCESRLSECARRL (SEQ ID NO: 324);
LLARCEARLEECGRQC (SEQ ID NO: 325);
DLLYCESRLAECGRM (SEQ ID NO: 326);
ALQMCEWRLEECARRL (SEQ ID NO: 327);
LLTMCEARLSECGRRL (SEQ ID NO: 328);
ALWRCESRLAECARRS (SEQ ID NO: 329);
LLATCAARLAECARQL (SEQID NO: 330);
LQTCEWKLAECARSN (SEQ ID NO: 331);
PLRSCESKLEECARQL (SEQ ID NO: 332);
CLRALDVKLAECARHL (SEQ ID NO: 333);
RLKTLELQLEECARRS (SEQ ID NO: 334);
KLRDVELKLAECARRS (SEQ ID NO: 335);
SLQRCEYKLASCARSL (SEQ ID NO: 336);
RLARCELRLAECARKS (SEQ ID NO: 337);
DLWYLESKLEECARRCN (SEQ ID NO: 338);
DLWYLESKLEECARRANG (SEQ ID NO: 339);
DLWYLESKLEECARRCNG (SEQ ID NO: 340);

KQRELELKLAECARRS (SEQ ID NO: 341);
QMQEWCARLAECARCCN (SEQ ID NO: 342); and
LLDICELKLQECARRAN (SEQ ID NO: 343).

A particularly preferred sequence of formula (VI) is:
LLDICELKLQECARRAN (SEQ ID NO: 343).

G. Compounds of Formula (VII):

In another aspect, the invention provides compounds comprising a peptide chain approximately 10 to 40 amino acids in length that binds to G-CSFR and contains a sequence of amino acids of formula (VII):

$$X^{VI}_1 X^{VI}_2 X^{VI}_3 X^{VI}_4 X^{VI}_5 E X^{VI}_6 X^{VI}_7 X^{VI}_8 X^{VI}_9 \text{ (SEQ ID NO: 7)} \quad \text{(VII)}$$

wherein each amino acid is indicated by standard one-letter abbreviation, and wherein $X^{VI}_1$ is A, E or G; $X^{VI}_2$ is E, H or D; $X^{VI}_3$ is R or G; $X^{VI}_4$ is K, Y, M, N, Q, R, D, I, S or E; $X^{VI}_5$ is A, S or P; $X^{VI}_6$ is E, D, T, Q, K or A: $X^{VI}_7$ is R, W, K, L, S, A or Q; $X^{VI}_8$ is R or E; and $X^{VI}_9$ is W, G, or R.

Preferably $X^{VI}_1$ is A; $X^{VI}_2$ is E; $X^{VI}_3$ is R; $X^{VI}_5$ is A; $X^{VI}_6$ is E; $X^{VI}_7$ is R; $X^{VI}_8$ is R; and $X^{VI}_9$ is W.

Examples of particularly preferred sequences satisfying formula (VII) include, but are not limited to, the following:

AERKAEERRW (SEQ ID NO: 344);
AERYAEEREG (SEQ ID NO: 345);
AERMAEERRW (SEQ ID NO: 346);
AERKAEERRR (SEQ ID NO: 347);
AHRNAEERRW (SEQ ID NO: 348);
AERKSEDWRW (SEQ ID NO: 349);
AERKAEEKRR (SEQ ID NO: 350);
AERQAETRRW (SEQ ID NO: 351);
AERNAEERRW (SEQ ID NO: 352);
AERQAEERRW (SEQ ID NO: 353);
AERRAEERRW (SEQ ID NO: 354);
AERDAEQRRW (SEQ ID NO: 355);
AERIAEERRW (SEQ ID NO: 356);
AERSAEERRW (SEQ ID NO: 357);
AERKAEELRW (SEQ ID NO: 358);
AERKAEESRW (SEQ ID NO: 359);
EERKAEERRW (SEQ ID NO: 360);
ADGKAEERRW (SEQ ID NO: 361);
ADGKAEELRW (SEQ ID NO: 362);
ADGMPEERRW (SEQ ID NO: 363);
ADGEAEKRRW (SEQ ID NO: 364);
ADGNAEERRW (SEQ ID NO: 365);
ADGEAEKARW (SEQ ID NO: 366);
AEGEAEKARW (SEQ ID NO: 367);
GERKAEERRW (SEQ ID NO: 368);
AEREAEERRW (SEQ ID NO: 369);
ADGEAEARRW (SEQ ID NO: 370);
ADGRAEEARW (SEQ ID NO: 371);
AEGRAEEARW (SEQ ID NO: 372);
AEREAEKARW (SEQ ID NO: 373);
AERKAEEQRW (SEQ ID NO: 374);
AERDAEKRRW (SEQ ID NO: 375); and
AEREAEKLRW (SEQ ID NO: 376).

Other preferred formula (VI) sequences include but are not limited to, the following:

MLAERKAEERRWFNTHGRE (SEQ ID NO: 377);
MLAERKAEERRWFNTHGREK (SEQ ID NO: 378);
GGGMLAERKAEERRWFNTHGRE (SEQ ID NO: 379);
CMLAERKAEERRWFNTHGRE (SEQ ID NO: 380);
CMLAERKAEERRWFNTHGREK (SEQ ID NO: 381);
MLAERYAEEREGFNMQWRE (SEQ ID NO: 382);
MLAERMAEERRWFRRMG (SEQ ID NO: 383);
IVAERKAEERRRLNTEGHE (SEQ ID NO: 384);
ILAHRNAEERRWFQKHGR (SEQ ID NO: 385);
MLAERKSEDWRWLKTHGRD (SEQ ID NO: 386);
MLAERKAEEKRRLKTQGRE (SEQ ID NO: 387);
ILAERQAETRRWMRNAGSVTK (SEQ ID NO: 388);
MLAERNAEERRWLKRQCG (SEQ ID NO: 389);
MLAERQAEERRWLKMHGGE (SEQ ID NO: 390);
MLAERRAEERRWLKTQGGD (SEQ ID NO: 391);
MLAERQAEERRWLKTQGRD (SEQ ID NO: 392);
MLAERKAEERRWFKTHGRE (SEQ ID NO: 393);
MLAERKAEERRWFNNQGRE (SEQ ID NO: 394);
MPAERDAEQRRWLKTHGRE (SEQ ID NO: 395);
ILAERIAEERRWLKTQGR (SEQ ID NO: 396);
MLAERKAEERRWLQTHGRE (SEQ ID NO: 397);
ILAERSAEERRWLKTQGRE (SEQ ID NO: 398);
LLAERKAEELRWLKTHGRE (SEQ ID NO: 399);
MLAERKAEERRWLQTHGRE (SEQ ID NO: 400);
MLAERNAEERRW (SEQ ID NO: 401);
MFAERKAEESRWLQSQGRE (SEQ ID NO: 402);
MLEERKAEERRWLKTHGR (SEQ ID NO: 403);
MLAERKAEERRWLKMQGRE (SEQ ID NO: 404);
MLAERNAEERRWFYTHGRE (SEQ ID NO: 405);
MLADGKAEERRWLKTHGLD (SEQ ID NO: 406);
MIADGKAEERRWLKTHGRD (SEQ ID NO: 407);
MLADGKAEELRWLKTQGSD (SEQ ID NO: 408);
MLAERNAEERRWLKTHGRD (SEQ ID NO: 409);
MLADGKAEELRWLKTQGRE (SEQ ID NO: 410);
ILADGKAEERRWLKTHGRD (SEQ ID NO: 411);
MLADGMPEERRWLQTHGRD (SEQ ID NO: 412);
MLADGEAEKRRWLNTHGRD (SEQ ID NO: 413);
MLADGNAEERRWLMTHGRD (SEQ ID NO: 414);
MLADGEAEKARWLKTQGRE (SEQ ID NO: 415);
MLAEGEAEKARWLKTQGRE (SEQ ID NO: 416);
MLADGKAEERRWLKTQGRE (SEQ ID NO: 417);
MLAERKAEERRWLSAHVRE (SEQ ID NO: 418);
LLGERKAEERRWYKTHARE (SEQ ID NO: 419);
MLAERKAEERRWLMTHGHD (SEQ ID NO: 420);
MLAERKAEERRWLKSQCLE (SEQ ID NO: 421);
LLAEREAEERRWFKTHGRE (SEQ ID NO: 422);
MLADGEAEARRWFNMHGRE (SEQ ID NO: 423);
MLADGRAEEARWLKTQGSE (SEQ ID NO: 424);
MLAEGRAEEARWLKTQGSE (SEQ ID NO: 425);
MLAEREAEKARWLKTQGRE (SEQ ID NO: 426);
MMAERKAEEQRWFDIHGRD (SEQ ID NO: 427);
LTAERDAEKRRWLLTHGGE (SEQ ID NO: 428);
MLAERQAEERRWLKSQRGE (SEQ ID NO: 429);
LLAERKAEERRWFATHGRD (SEQ ID NO: 430);
MLAEREAEKLRWLKSQERA (SEQ ID NO: 431);
MLAERKAEERRWLKTHGGE (SEQ ID NO: 432);
KGGGMLAERKAEERRWFNTHGRE (SEQ ID NO: 490); and
KSTGGLTAERDAEKRRWLLTHGGE (SEQ ID NO: 491).

H. Other Active Compounds

In another aspect of the invention, there are provided additional compounds comprising a peptide chain approximately 5 to 40 amino acids in length that binds to G-CSFR and contains a sequence of amino acids selected from the following compounds:

CTWTDLESVY (SEQ ID NO: 433);
HTTNEQFFMC (SEQ ID NO: 434);
DTWLELESRY (SEQ ID NO: 435);
HNSSPMVGVT (SEQ ID NO: 436);
DWQKTIPAYW (SEQ ID NO: 437);
RWGREGLVAALL (SEQ ID NO: 438);
WSGTRVWRCVVT (SEQ ID NO: 439);
MSLLSYLRS (SEQ ID NO: 440);
LDLLAI (SEQ ID NO: 441);
RIYGVK (SEQ ID NO: 442);
MIWHMFMSLLF (SEQ ID NO: 443);
FFWASWMHLLW (SEQ ID NO: 444);
FDDCWREREQFLFQAL (SEQ ID NO: 445);
CGRASECFRLLEM (SEQ ID NO: 446);
RECFQMLER (SEQ ID NO: 447);
CSIRWDFVPGYGLC (SEQ ID NO: 448);
WMQCWDSLSLCYDM (SEQ ID NO: 449);
ALLMCESKLAECARAR (SEQ ID NO: 450);
LAHCKKRKEECAAG (SEQ ID NO: 451);
SIDGVYLRTSRT (SEQ ID NO: 452);
SIDGVYLRTRSRTRY (SEQ ID NO: 453);
VRWLRGSTLRGLRDR (SEQ ID NO: 454);
DRGGGTVGVYWWESY (SEQ ID NO: 455);
VWGTVGTWLEY (SEQ ID NO: 456);
LMWVSAY (SEQ ID NO: 457);
RASDEYGALVRFCTNL (SEQ ID NO: 458);
NYWCDSNWVCEIA (SEQ ID NO: 459);
LAHCLLRLEECAAG (SEQ ID NO: 460);
LALCLARLRECAGG (SEQ ID NO: 461);
CESRLVECSRM (SEQ ID NO: 462);
LLDIAELKLQECARRCN (SEQ ID NO: 463);
KLLDIAELKLQECCARRCN (SEQ ID NO: 464);
CSTGGGLTAERDAEKRRWLLTHGGE (SEQ ID NO: 465)
LTAERDAEKRRWLLTHGGEGG (SEQ ID NO: 466);
LTAERDAEKRRWLLTHGGEGGK (SEQ ID NO: 467);
LTAERDAEKRRWLLTHGGEGGGGG (SEQ ID NO: 468);
LTAERDAEKRRWLLTHGGEGGGGGK (SEQ ID NO: 469);
ESGWVW (SEQ ID NO: 470);
NSGWVW (SEQ ID NO: 471);
SGWVW (SEQ ID NO: 472);
PLGKCEATCREMARYFN (SEQ ID NO: 473);
SLQRCEYKLASVRGLCN (SEQ ID NO: 474)
DLWYLESKLEEAARRCNG (SEQ ID NO: 475);
PYMGTRSRAKLLRQQ (SEQ ID NO: 476);
RNAGERRWFKTQGWY (SEQ ID NO: 477);
MLAERNADDRRWFNTHGRD (SEQ ID NO: 478);
MMADGRLRNSVGLILWCD (SEQ ID NO: 479);
MLADGRLRNVVG (SEQ ID NO: 480);
LLADVRRRNGVGLLRMGRD (SEQ ID NO: 481);
MLADGRLRNFGG (SEQ ID NO: 482);
TYMTYVYWLC (SEQ ID NO: 483);
RFGERWGL (SEQ ID NO: 484);
HWLWWGWNF (SEQ ID NO: 485);
RECFQMLERC (SEQ ID NO: 486);
ILAHRNAKERRWFQKHGR (SEQ ID NO: 487); and
CSTGGGLTAERDAEKRRWLLTHGGEK (SEQ ID NO: 489).

Particularly preferred sequences are selected from the group consisting of:

LLDIAELKLQECARRCN (SEQ ID NO: 463); and
KLLDIAELKLQECCARRCN (SEQ ID NO: 464).

I. Synthesis of the Peptides:

Standard solid phase peptide synthesis techniques are preferred for synthesis of the peptides of the present invention. Such techniques are described, for example, by Merrifield (1963) *J. Am. Chem. Soc.* 85:2149. As is well known in the art, solid phase synthesis using the Merrifield method involves successive coupling of α-amino protected amino acids to a growing support-bound peptide chain. After the initial coupling of a protected amino acid to a resin support (e.g., a polystyrene resin, a chloromethylated resin, a hydroxymethyl resin, a benzhydrylamine resin, or the like, depending on the chemistry used), the α-amino protecting group is removed by a choice of reagents, depending on the specific protecting group. Suitable α-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, cyclohexyloxycarbonyl), alkyl type protecting groups (e.g., benzyl, triphenylmethyl), fluorenylmethyl oxycarbonyl (Fmoc), alloxycarbonyl (Alloc) and Dde. The side chain protecting groups (typically ethers, esters, trityl, and the like) remain intact during coupling; however, the side chain protecting group must be removable upon completion of the synthesis of the final peptide. Preferred side chain protecting groups, as will appreciated by those skilled in the art, will depend on the particular amino acid that is being protected as well as the overall chemistry used. After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodiimide (DCC) in solution, for example, in methylene chloride ($CH_2Cl_2$), N-methyl pyrrolidone, dimethyl formamide (DMF), or mixtures thereof.

Once the synthesis is complete, the compound is cleaved from the solid support by treatment with a reagent such as trifluoroacetic acid, preferably in combination with a scavenger such as ethanedithiol, P-mercaptoethanol or thioanisole. The cleavage reagent not only cleaves the peptide from the resin, but also cleaves all remaining side chain protecting groups.

These procedures can also be used to synthesize peptides containing amino acids other than the 20 naturally occurring, genetically encoded amino acids. For instance, naphthylalanine can be substituted for tryptophan, with 1-Nal or 2-Nal. Other synthetic amino acids that can be substituted into the peptides of the present invention include, but are not limited to, nor-leucine and 3-pyridylalanine.

III. Variation and Modification of the Compounds
A. Dimer Forms (With a Terminal Linking Moiety):

The compounds of the present invention may be in the form of a dimer, i.e., a compound comprised of two similar (but not necessarily identical) peptide sequences. Preferably, the dimer compounds of the invention have the structure of formula (VIII)

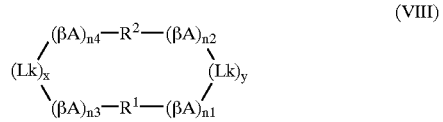
(VIII)

wherein $R^1$, $R^2$, n1, n2, n3, n4, x, y and Lk are defined as follows.

$R^1$ is a peptide chain that binds to G-CSFR and contains a sequence of amino acids of the present invention. $R^2$ is also a peptide chain that binds to G-CSFR and contains a sequence of amino acids of the present invention. As previously indicated, $R^1$ and $R^2$ can be the same or different. It is preferred, however, that $R^1$ and $R^2$ are the same.

βA is a β-alanine residue and may or may not be present, meaning that n1, n2, n3 and n4 are independently zero or 1.

Lk is a terminal linking moiety. If the dimer contains only one linking moiety, one of x and y is zero and the other is one. Alternatively, if the dimer contains two linking moieties, both x and y are one. Thus, x and y are independently zero or one with the proviso that the sum of x and y is either one or two.

The terminal linking moiety Lk can be any moiety recognized by those skilled in the art as suitable for joining the peptides of $R^1$ and $R^2$. Lk is preferably although not necessarily selected from the group consisting of a disulfide bond, a carbonyl moiety and a $C_{1-12}$ linking moiety optionally terminated with one or two —NH— linkages and optionally substituted at one or more available carbon atoms with a lower alkyl substituent. Preferably, the terminal linking moiety comprises —NH—$R^3$—NH— wherein $R^3$ is lower ($C_{1-6}$) alkylene substituted with a functional group such as a carboxyl group or an amino group that enables coupling to another molecular moiety (e.g., as may be present on the surface of a solid support), and is optionally substituted with a lower alkyl group. Optimally, the linking moiety is a lysine residue or lysine amide, i.e., a lysine residue wherein the carboxyl group has been converted to an amide moiety —$CONH_2$.

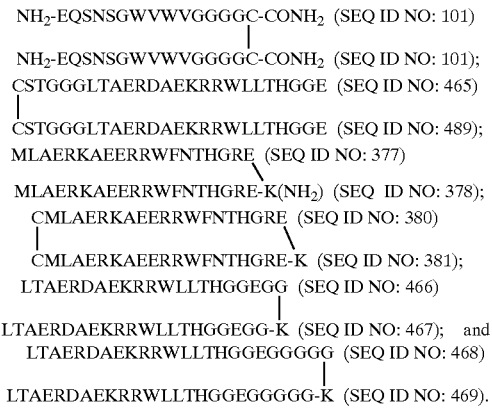

B. Disulfide Bonds:

When a pair of cysteine residues is present in a peptide of the invention, it is preferred that the pair form a disulfide bond linking these residues. The disulfide bond may be present within a single peptide chain forming an intramolecular disulfide bond. Alternatively, if the compound includes an additional cysteine-containing peptide chain, the disulfide bond may connect the two chains. In addition, where an additional pair of cysteine residues exists in the compound, more than one disulfide bond may be present.

Disulfide bond formation may be effected by techniques well known to those skilled in the art. One such technique involves employing a suitable oxidizing reagent such that a disulfide bond forms from the free thiols from a pair of cysteine residues. Undesired disulfide bond formation can be minimized, for example, by protecting the thiol groups of those cysteine residues not intended to form disulfide bonds and oxidizing the peptide before removal of any protecting groups. Preferred compounds having disulfide bonds include, by way of example, the following:

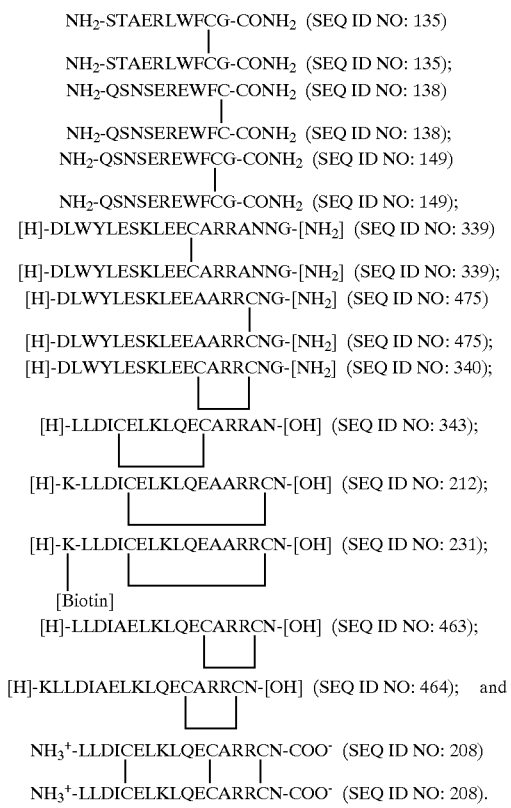

A particularly preferred compound having disulfide bonds includes

C. N-Terminal Modifications:
(i) Pegylated Compounds

The peptides and compounds of the invention can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in binding activity. Nonproteinaceous polymers suitable for use in accordance with the present invention include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 60,000 daltons and, even more preferably, from about 5,000 to about 50,000 daltons. In preferred embodiments, such hydrophilic polymers have average molecular weights of about 5,000 daltons, 10,000 daltons 20,000 daltons and 40,000 daltons.

The peptide compounds of the invention can be derivatized with or coupled to such polymers using any of the methods set forth in Zallipsky (1995) *Bioconjugate Chem.* 6:150–165; Monfardini et al. (1995) *Bioconjugate Chem.* 6:62–69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 or WO 95/34326.

In a preferred embodiment, the N-terminus of a peptide of the invention is coupled to a polyethylene glycol molecule. It is particularly preferred that the polymer is selected from the group consisting of polyethylene glycol, polypropylene glycol, polylactic acid, polyglycolic acid and derivatives and combinations thereof. Most preferably the polymer is polyethylene glycol (PEG), in which case the peptide is referred to as "PEGylated." PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have an average molecular weight of from about 500 to about 80,000 daltons. It is particularly preferred that the polymer has an average molecular weight of between about 5,000 to 40,000 daltons.

The PEG coupled to the peptide compounds of the invention can be either ranched or unbranched. (See, e.g. Monfardini et al. (1995) *Bioconjugate Chem.* 6:62–69.) PEG is commercially available from Shearwater Polymers, Inc. (Huntsville, Ala.), Sigma Chemical Co. and other companies. Suitable PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES) and monomethoxypolyethylene glycol-imidazolyl-carbonyl (MePEG-IM).

Briefly, in one exemplary embodiment, the hydrophilic polymer which is employed, e.g., PEG, is capped at one terminus by an unreactive group such as a methoxy or ethoxy group. Thereafter, the polymer is activated at the other terminus by reaction with a suitable activating agent, such as a cyanuric halide (e.g., cyanuric chloride, bromide or fluoride), diimidazole, an anhydride reagent (e.g., a dihalosuccinic anhydride, such as dibromosuccinic anhydride), acyl azide, p-diazoniumbenzyl ether, 3-(p-diazoniumphenoxy)-2-hydroxypropylether, or the like. The activated polymer is then reacted with a peptide compound of the invention to produce a polymer-derivatized peptide compound. Alternatively, a functional group in the peptide compounds of the invention can be activated for reaction with the polymer, or two groups can be joined in a concerted coupling reaction using known coupling methods. It will be readily appreciated that the peptide compounds of the invention can be derivatized with PEG using a myriad of other reaction schemes known to those of skill in the art.

(ii) Acetylated Compounds

In some instances, the N-terminus of the peptide is acetylated. Preferred acetylated compounds include, by way of example, the following:

Ac-ESGWVW-CONH$_2$ (SEQ ID NO: 470);
Ac-NSGWVW-CONH$_2$ (SEQ ID NO: 471); and
Ac-SGWVW-CONH$_2$ (SEQ ID NO: 472).

The peptides and compounds of the invention can be modified with an acetyl moiety (Ac) using standard techniques known to those skilled in the art. One such technique includes combining the peptide with an acetylating reagent (e.g., acetyl chloride, acetic anhydride) in a suitable solvent to form the acetylated product. To the extent that other acetylated products are formed during the reaction, the N-terminus derivative can be isolated using conventional separation techniques.

D. C-Terminal Modifications:

The peptides and compounds of the invention can advantageously be modified to include an amide functionality at the carboxyl terminus of the peptide. Thus, it is preferred that the C-terminus of the peptide is amidated.

In preparing peptides wherein the C-terminus carboxyl group is replaced by the amide —C(O)NR$^3$R$^4$ where R$^3$ and R$^4$ are independently H or lower (C$_{1-6}$) alkyl, a benzhydrylamine resin is preferably used as the solid support for peptide synthesis. Upon completion of the synthesis, a hydrogen fluoride treatment is employed to release the peptide from the support, directly resulting in the free peptide amide (i.e., the C-terminus is —C(O)NH$_2$). Alternatively, use of a chloromethylated resin during peptide synthesis coupled with reaction with ammonia (to cleave the side chain protected peptide from the support) yields the free peptide amide and reaction with an alkylamine or a dialkylamine yields a side chain protected alkylamide or dialkylamide (i.e., the C-terminus is —C(O)NR$^3$R$^4$ where R$^3$ and R$^4$ are as defined above). Side chain protecting groups are then removed in the usual fashion by treatment with hydrogen fluoride to give the free amides, alkylamides, or dialkylamides.

E. Other Modifications:

One can also replace the naturally occurring side chains of the 20 genetically encoded amino acids (or the stereoisomeric D amino acids) with other side chains, for instance with groups such as alkyl, lower alkyl, cyclic 4-, 5-, 6- or 7-membered alkyl, amide, amide lower alkyl, amide di(lower alkyl), lower alkoxy, hydroxy, carboxy and the lower ester derivatives thereof, and 4-, 5-, 6- or 7-membered heterocyclic. In particular, proline analogues in which the ring size of the proline residue is changed from 5 members to 4, 6, or 7 members can be employed.

One can also readily modify the peptides herein by phosphorylation or other methods as described in Hruby et al. (1990) *Biochem J.* 268:249–262. Thus, the peptides of the invention also serve as structural models for non-peptidic compounds with similar biological activity. For example, the peptide backbones may be replaced with a backbone composed of phosphonates, amidates, carbamates, sulfonamides, secondary amines, and N-methylamino acids.

IV. Utility

The compounds of the invention are useful in vitro as unique tools for understanding the biological role of G-CSF, including the evaluation of the many factors thought to influence, and be influenced by, the production of white blood cells. The present compounds are also useful in the development of other compounds that bind to G-CSFR, because the compounds provide important structure-activity relationship (SAR) information that facilitates that development.

Moreover, based on the ability to bind to G-CSFR and related receptors, a compound of the invention can be used as a reagent for detecting a G-CSF receptor or related receptor on living cells, fixed cells, in biological fluids, in tissue homogenates, in purified, natural biological materials, etc. For example, by labeling a compound of the invention, one can identify a cell expressing G-CSFR on its surface. In addition, based on it ability to bind a G-CSFR, a compound of the invention can be used in in situ staining, FACS (fluorescence-activated cell sorting), Western blotting, ELISA (enzyme-linked immunoadsorptive assay), etc. In addition, because of its ability to bind to a G-CSFR, a compound of the invention can be used in receptor purification or in purifying cells expressing G-CSFR on the cell surface (or inside permeabilized cells).

A compound of the invention can also be utilized as a commercial research reagent for various medical research and diagnostic uses. Such uses include but are not limited to: (1) use as a calibration standard for quantitating the activities of candidate G-CSFR antagonists or agonists in a variety of functional assays; (2) use as a blocking reagent in random peptide screening, i.e., in searching for new families of G-CSFR peptide ligands; (3) use in the co-crystallization with G-CSFR, i.e., a compound of the invention will allow formation of crystals bound to G-CSFR, enabling the determination of receptor/peptide structure x-ray crystallography; (4) use in inhibiting or decreasing the proliferation and growth of G-CSF-dependent cell lines; and (5) other research and diagnostic applications wherein the action of G-CSFR is to be mimicked, and the like.

A compound of the invention can also be administered to a warm blooded animal, including a human, to treat a disease that would benefit from the ability of a compound to mimic the effects of G-CSF in vivo. Thus, the present invention encompasses methods for treating a patient who would benefit from a G-CSFR modulator, comprising administering to the patient a therapeutically effective amount of a compound of the invention to activate G-CSFR. For example, a compound of this invention will find use in the treatment of diseases such as a depressed neutrophil count. Although attributable to a myriad of causes, a depressed neutrophil count is commonly associated with chemotherapy, AIDS and pneumonia (particularly community-acquired pneumonia). Thus, it is preferred that a compound of the present invention be used to treat a depressed neutrophil count selected from the group consisting of chemotherapy-induced neutropenia, AIDS-induced neutropenia and community-acquired pneumonia-induced neutropenia.

In addition, the invention encompasses methods for treating a patient who would benefit from a G-CSFR modulator, comprising administering to the patient a therapeutically effective amount of a compound of the invention that antagonizes the action of G-CSF to the G-CSFR in vivo. For example, these receptor antagonists are administered prior to and during chemotherapy to confer chemoprotection to the neutrophil progenitor cells by preventing their proliferation in the presence of cytotoxic drugs. Once chemotherapy administration is suspended, the administration of the chemoprotective G-CSFR antagonists is also suspended thereby allowing the patient's endogenous G-CSF to stimulate proliferation. Alternatively, the neuirophil progenitor cells may be "rescued" by administration of G-CSF or by a G-CSF agonist, e.g., a compound of the present invention having G-CSF agonist activity.

Accordingly, the invention includes pharmaceutical compositions comprising, as an active ingredient, at least one of the compounds of the invention in association with a pharmaceutical carrier or diluent. The composition can be administered by oral, parenteral (intramuscular, intraperitoneal, intravenous (IV) or subcutaneous) injection, transdermal (either passively or using iontophoresis or electroporation), or transmucosal (nasal, vaginal, rectal, or sublingual) routes of administration, or using bioerodible inserts, and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, an additional substance other than an inert diluent, e.g., a lubricating agent such as magnesium stearate. In the case of capsules, tablets, and pills, the dosage forms may also comprise a buffering agent. Tablets and pills can additionally be prepared with enteric coatings.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as a wetting agent, an emulsifying agent, a suspending agent, a sweetening agent, a flavoring agent or a perfuming agent.

Preparations for parenteral administration include sterile aqueous or non-aqueous solutions, suspensions, and emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain one or more adjuvants such as a preserving agent, a wetting agent, an emulsifying agent and a dispersing agent. The dosage forms may be sterilized by, for example, filtration through a bacteria-retaining filter, by incorporating sterilizing agents into the compositions, by irradiating the compositions, or by heating the compositions. They can also be manufactured using sterile water, or some other sterile injectable medium, prior to use.

Compositions for rectal or vaginal administration are preferably suppositories which may contain, in addition to the active substance, an excipient such as cocoa butter or a suppository wax. Compositions for nasal or sublingual administration are also prepared with one or more standard excipients well known in the art.

The dosage of active ingredient in the compositions of this invention may be varied; however, it is necessary that the amount of the active ingredient is such that a suitable dosage form is obtained. The selected dosage depends upon the desired therapeutic effect, the route of administration, the duration of the treatment desired, and other factors well known to those skilled in the art. Generally, dosage levels of between 0.001 to 10 mg/kg of body weight daily are administered to mammals.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

EXPERIMENTAL

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Standard peptide synthetic methods were used, and solid phase reactions were carried out at room temperature. Unless otherwise indicated, all starting materials and reagents were obtained commercially, e.g., from Aldrich, Sigma and ICN, and used without further purification. Standard cell culture and cell harvesting procedures were used.

Also, in these examples and throughout this specification, the abbreviations employed have their generally accepted meanings, as follows:

Ac=acetyl

BSA=bovine serum albumin

DMSO=dimethyl sulfoxide

DTT=dithiothreitol

HPLC=high pressure liquid chromatography

MBP=maltose binding protein

PBS=phosphate-buffered saline

SDS PAGE=sodium dodecyl sulfate polyacrylamide gel electrophoresis

TCEP=tris(2-carboxyethyl) phsophine

TFA=trifluoroacetic acid

Tris=tris[hydroxymethyl]aminomethane

EXAMPLES 1–34

G-CSF Competition Binding Assays

The peptides of Table 1 were synthesized using standard techniques and were subsequently evaluated to identify whether the peptides exhibited specific and/or competitive binding.

Specific binding is binding of a ligand to a specific receptor, as opposed to non-specific binding that is mediated by non-specific interactions. Specific binding may be measured by subtraction of the non-specific binding (measured in the presence of saturating concentrations of unlabeled ligand) from the total binding (measured in the absence of saturating amounts of ligand). Typically, the unlabeled ligand used was a variant of G-CSF in which the cysteine normally found at position 17 was converted to serine (CS17).

Determination of competitive binding was also carried out for a number of peptides. Briefly stated, G-CSFR was purified using standard techniques. The receptor was then immobilized in microtiter plate wells that were coated with acid-treated antibody (Ab179) specific for a site on G-CSFR not involved with G-CSF binding. Separately, $^{125}$I was coupled to the natural ligand G-CSF using techniques well known in the art. Test peptides were added to receptor-coated wells and allowed to bind to immobilized receptor for approximately 30 minutes. $^{125}$ labeled G-CSF was then introduced to the wells and incubated overnight at 4°C. Unbound $^{125}$I labeled G-CSF was removed by washing the plate several times followed by measuring the amount of radioactivity that remained in each well using conventional techniques. If no reduction in the amount of bound $^{125}$I labeled G-CSF was detected, the peptide did not compete for binding to the receptor. Alternatively, if reduced amounts or no $^{125}$I labeled G-CSF was detected, the peptide did compete. Non-positive results for a particular peptide are not dispositive of that peptide's activity: the peptide may exhibit binding under conditions different from those tested.

The results of these assays reveal important information about the structure activity relationship for peptide and peptide mimetics of the invention to the G-CSF receptor.

TABLE 1

| Ex. No. | Sequence | | | | Specific Binding? | Competitive Binding? |
|---|---|---|---|---|---|---|
| 1 | CAGEVMHMCC | (SEQ | ID | NO: 8) | Yes | Yes |
| 2 | CNREIEAMCC | (SEQ | ID | NO: 9) | Yes | Yes |
| 3 | CADEVMHFCC | (SEQ | ID | NO: 10) | Yes | Yes |
| 4 | CDVWQLFDRC | (SEQ | ID | NO: 25) | Yes | Yes |
| 5 | CSFVQLNSIC | (SEQ | ID | NO: 26) | Yes | Yes |
| 6 | CVPWMFYDLC | (SEQ | ID | NO: 29) | Yes | No |
| 7 | CDPWMFYDLC | (SEQ | ID | NO: 30) | Yes | No |
| 8 | CQRAGYMLAC | (SEQ | ID | NO: 44) | No | No |
| 9 | CHANPVWGEC | (SEQ | ID | NO: 45) | No | No |
| 10 | CTWTDLESVY | (SEQ | ID | NO: 433) | No | No |
| 11 | CFWSDWGQTC | (SEQ | ID | NO: 46) | No | No |
| 12 | CPDWYQSYMC | (SEQ | ID | NO: 34) | Yes | Yes |
| 13 | CPHWTSYYMC | (SEQ | ID | NO: 47) | Yes | Yes |
| 14 | CACMLRVVHC | (SEQ | ID | NO: 43) | Yes | Yes |
| 15 | CETLCGACFC | (SEQ | ID | NO: 44) | No | No |
| 16 | SNESGWVWLP | (SEQ | ID | NO: 110) | Yes | No |
| 17 | EQSNSGWVWV | (SEQ | ID | NO: 111) | Yes | No |
| 18 | SRTESGWVWT | (SEQ | ID | NO: 112) | Yes | No |
| 19 | QRANSGWVWV | (SEQ | ID | NO: 113) | Yes | No |
| 20 | DYDNSGWVWH | (SEQ | ID | NO: 114) | Yes | No |
| 21 | ETWGERDWFC | (SEQ | ID | NO: 133) | Yes | Yes |
| 22 | STAERLWFCG | (SEQ | ID | NO: 135) | Yes | Yes |
| 23 | YETAERSYFC | (SEQ | ID | NO: 119) | Yes | Yes |
| 24 | ADNAERGWFC | (SEQ | ID | NO: 137) | Yes | Yes |
| 25 | QSNSEREWFC | (SEQ | ID | NO: 138) | Yes | Yes |
| 26 | STSERAWFCG | (SEQ | ID | NO: 139) | Yes | Yes |
| 27 | ASWSERGWFC | (SEQ | ID | NO: 140) | Yes | Yes |
| 28 | ELSSEREWFC | (SEQ | ID | NO: 141) | Yes | Yes |
| 29 | DMQGERGWFC | (SEQ | ID | NO: 142) | Yes | Yes |
| 30 | DMVYAYPPWS | (SEQ | ID | NO: 155) | Yes | No |
| 31 | DEMVYTVPYW | (SEQ | ID | NO: 156) | Yes | Yes |
| 32 | HTTNEQFFMC | (SEQ | ID | NO: 434) | Yes | Yes |
| 33 | DTWLELESRY | (SEQ | ID | NO: 435) | Yes | No |
| 34 | DWQKTIPAYW | (SEQ | ID | NO: 437) | Yes | Yes |

EXAMPLES 35–73

G-CSF Radioligand Binding Assays

The peptides of Table 2 were synthesized using standard techniques and were subsequently evaluated to determine their binding affinities to G-CSFR.

Streptavidin-coated scintillation proximity assay (SPA) beads (Amersham) were mixed with biotinylated anti-receptor immobilizing antibody (Ab179) followed by incubation with soluble G-CSFR harvest. Receptor-coated SPA beads were washed twice in PBS/0.1% BSA and distributed to wells of a white polystyrene 96-well microtiter plate (Packard). Serial dilutions of peptide or peptide mimetic were mixed with a constant amount of $^{125}$I labeled G-CSF ($10^5$ cpm; 1290 Ci/mmol) in PBS/0.1% BSA, added to wells containing receptor-coated SPA beads, and incubated overnight at 4° C. The binding of radiolabeled G-CSF to the receptor-coated SPA bead brings the isotope in close proximity to the scintillant, which allows the emitted radiation to stimulate the scintillant to emit light. Any unbound radiolabeled ligand is not in close enough proximity to the scintillant to allow such energy transfer and hence no signal is generated. The amount of $^{125}$I labeled G-CSF that was bound at equilibrium was measured by counting the plate in a TopCount (Wallac) microtiter plate luminometer. The assay is conducted over a range of peptide concentrations and the results are graphed such that the y-axis represents the amount of bound $^{125}$I labeled G-CSF and the x-axis represents the concentration of peptide or peptide mimetic. One can determine the concentration at which the peptide or peptide mimetic will reduce by 50% ($IC_{50}$) the amount of $^{125}$I labeled G-CSF bound to immobilized G-CSFR. The dissociation constant ($K_d$) for the peptide should be similar to the measured $IC_{50}$ using the assay conditions described above.

The peptides along with their corresponding $IC_{50}$ values are shown in Table 2. $IC_{50}$ values are indicated symbolically by the symbols "−", "+", and "++". For examples, those peptides which showed $IC_{50}$ values in excess of 200 uM are indicated with a "−". Those peptides which gave $IC_{50}$ values of less than or equal to 200 uM are given a "+", while those which gave $IC_{50}$ values of 500 nM or less are indicated with a "++". Those peptides, which gave $IC_{50}$ values at or near the cutoff point for a particular symbol, are indicated with a hybrid designator, e.g., "+/−". The peptides for which $IC_{50}$ values were not determined are listed as "N.D.".

The results of these assays reveal important information about the structure-activity relationship for peptide and peptide mimetics of the invention to the G-CSF receptor.

TABLE 2

| Ex. No. | Sequence | $IC_{50}$ |
|---|---|---|
| 35 | NH$_2$-EQSNSGWVWV-CONH$_2$ (SEQ ID NO:111) | + |
| 36 | NH$_2$-STAERLWFCG-CONH$_2$ (SEQ ID NO:135) | − |
| 37 | NH$_2$-STAERLWFCG-CONH$_2$ (SEQ ID NO:135)<br>             \|<br>NH$_2$-STAERLWFCG-CONH$_2$ (SEQ ID NO:135) | + |
| 38 | NH$_2$-QSNSEREWFC-CONH$_2$ (SEQ ID NO:138) | − |
| 39 | NH$_2$-QSNSEREWFC-CONH$_2$ (SEQ ID NO:138)<br>             \|<br>NH$_2$-QSNSEREWFC-CONH$_2$ (SEQ ID NO:138) | − |
| 40 | NH$_2$-QSNSEREWFCG-CONH$_2$ (SEQ ID NO:149) | − |
| 41 | NH$_2$-QSNSEREWFCG-CONH$_2$ (SEQ ID NO:149)<br>             \|<br>NH$_2$-QSNSEREWFCG-CONH$_2$ (SEQ ID NO:149) | − |
| 42 | Ac-ESGWVW-CONH$_2$ (SEQ ID NO:470) | − |
| 43 | Ac-NSGWVW-CONH$_2$ (SEQ ID NO:471) | − |
| 44 | Ac-SGWVW-CONH$_2$ (SEQ ID NO:472) | − |
| 45 | NH$_2$-EQSNSGWVWVGGGGC-CONH$_2$ (SEQ ID NO:101) | + |
| 46 | NH$_2$-EQSNSGWVWVGGGGC-CONH$_2$ (SEQ ID NO: 101)<br>             \|<br>NH$_2$-EQSNSGWVWVGGGGC-CONH$_2$ (SEQ ID NO: 101) | + |
| 47 | CESRLVECSRM (SEQ ID NO:462) | +/− |
| 48 | LAHCLLRLEECAAG (SEQ ID NO:460) | +/− |
| 49 | ALLMCESKLAECARAR (SEQ ID NO:450) | +/− |
| 50 | DLWYLESKLEECARRANG (SEQ ID NO:339)<br>             \|<br>DLWYLESKLEECARRANG (SEQ ID NO:339) | + |
| 51 | DLWYLESKLEECARRCNG (SEQ ID NO:340) | + |
| 52 | DLWYLESKLEEAARRCNG (SEQ ID NO:475)<br>             \|<br>DLWYLESKLEEAARRCNG (SEQ ID NO:475) | + |
| 53 | LLDICELKLQECARRCN (SEQ ID NO:208) | ++ |
| 54 | GGGLLDICELKLQECARRCN (SEQ ID NO:209) | ++ |
| 55 | GRTGGGLLDICELKLQECARRCN (SEQ ID NO:210) | ++ |
| 56 | LGIEGRTGGGLLDICELKLQECARRCN (SEQ ID NO:211) | ++ |
| 57 | LLDICELKLQECARRAN (SEQ ID NO:343) | + |
| 58 | LLDICELKLQEAARRCN (SEQ ID NO:212) | + |
| 59 | Biotin-LLDICELKLQECARRAN (SEQ ID NO:343) | + |
| 60 | Biotin-KLLDICELKLQEAARRCN (SEQ ID NO:213) | + |
| 61 | LLDIAELKLQECARRCN (SEQ ID NO:463) | + |
| 62 | Biotin-KLLDIAELKLQECARRCN (SEQ ID NO:464) | + |
| 63 | Biotin-KGGGMLAERKAEERRWFNTHGRE (SEQ ID NO:490) | + |
| 64 | MLAERKAEERRWFNTHGRE (SEQ ID NO:377)<br>             \|<br>MLAERKAEERRWFNTHGREK (SEQ ID NO:378) | +/− |
| 65 | CMLAERKAEERRWFNTHGRE (SEQ ID NO:380)<br>\|            \\<br>CMLAERKAEERRWFNTHGREK (SEQ ID NO:381) | N.D. |
| 66 | H$_2$N-KSTGGLTAERDAEKRRWLLTHGGE-COOH (SEQ ID NO:491) | − |
| 67 | CSTGGGLTAERDAEKRRWLLTHGGE (SEQ ID NO: 465)<br>\|<br>CSTGGGLTAERDAEKRRWLLTHGGE (SEQ ID NO: 465) | + |
| 68 | LTAERDAEKRRWLLTHGGEGG (SEQ ID NO:466)<br>             \|<br>LTAERDAEKRRWLLTHGGEGGK (SEQ ID NO:467) | − |

TABLE 2-continued

| Ex. No. | Sequence | IC$_{50}$ |
|---|---|---|
| 69 | LTAERDAEKRRWLLTHGGEGGGGG (SEQ ID NO:468)<br>\|<br>LTAERDAEKRRWLLTHGGEGGGGGK (SEQ ID NO:469) | – |
| 70 | YLELCQLRLEECARQFN (SEQ ID NO:282) | + |
| 71 | CGCHVSPVQIKALC (SEQ ID NO:198) | + |
| 72 | GCHVSPVQIKALC (SEQ ID NO:199) | – |
| 73 | HELCETYADWLGCVEW (SEQ ID NO:76) | N.D. |

EXAMPLES 74–81

Cell Proliferation and Luminescence Assays

The bioactivity of selected peptides of the invention was measured in cell-based assays. Murine NFS-60 cells proliferate in the presence of G-CSF in a dose dependent manner and were used in standard cell proliferation assays that are well known in the art. Murine IL-3 dependent Ba/F3 cells were co-transfected with expression vectors encoding the full length human G-CSFR and a luciferase reporter gene controlled by the fos promoter. The Ba/F3 G-CSFR reporter cell line is not only dependent on the presence of G-CSF for proliferation, but also produces luciferase in response to the addition of G-CSF in a dose dependent manner. The parental, untransfected cell line does not respond to G-CSF or produce luciferase, but remains IL-3 dependent.

Reporter cell assays were performed on the above cell line using peptides of the invention. The cells were maintained in complete RPMI-164Q media containing 10% fetal calf serum, 2 mM L-glutamine, 1X antibiotic-antimycotic solution (Life Technologies), and 10% WEHI-3 conditioned media (source of murine IL-3). For reporter assays, cells were starved overnight in medium which lacks WEHI-3 to reduce luciferase expression to background levels. The cells were then washed twice in PBS, resuspended in media which lacks WEHI-3 conditioned media, and added to wells of a 96-well microtiter plate containing dilutions of peptide or G-CSF at $5 \times 10^4$ cells/well. Plates were incubated for 2 hours at 37° C. in a humidified 5% CO$_2$ incubator and luciferase activity was measured by the addition of luciferin (LucLite—Packard Biosciences) to each well. The plates were read in a TopCount (Wallac) microtiter plate luminometer.

To measure the ability of selected peptides of the invention to block G-CSF mediated receptor activation, dilutions of peptide were combined with Ba/F3 G-CSFR reporter cells as described above. After a 30-minute incubation at 37° C., G-CSF was added to each well. The cells were incubated for 2 hours at 37° C. and the amount of luciferase produced was measured as described above.

The following seven peptides were tested for bioactivity:

| | | |
|---|---|---|
| Ex.74 | NH$_2$-EQSNSGWVWV-CONH$_2$ | (SEQ ID NO:111); |
| Ex.75 | NH$_2$-STAERLWFCG-CONH$_2$ | (SEQ ID NO:135); |
| Ex.76 | NH$_2$-STAERLWFCG-CONH$_2$<br>\|<br>NH$_2$-STAERLWFCG-CONH$_2$ | (SEQ ID NO:135);<br><br>(SEQ ID NO:135); |
| Ex.77 | QLETCVLKLEECARRCN | (SEQ ID NO:315); |
| Ex.78 | LLDICELKLQECARRCN | (SEQ ID NO:208); |
| Ex.79 | PLFSCELKKQECARRCN | (SEQ ID NO:323); and |
| Ex.80 | DLWYLESKLEECARRCN | (SEQ ID NO:338). |

Examples 74, 75, and 76 showed antagonist activity at high concentrations in cell-based assays using NFS-60 cells. The stability of Example 74 in cell culture medium was tested by overnight incubation in NFS-60-conditioned medium; no loss of activity was observed, indicating that the peptide is stable to degradation under these conditions.

Examples 77, 78, 79, and 80 showed cell proliferation activity when fused to the carboxy-terminus of the maltose binding protein (MBP). The MBP fusion protein of Example 78 in particular showed high affinity in a binding competition assay with $^{125}$I-GCSF (IC$_{50}$~10 nM) and activity in a Ba/F3 G-CSFR cell proliferation assay (maximal activity at 100 nM). Parental Ba/F3 cells and Ba/F3 cells expressing the human thrombopoietin receptor did not proliferate in response to this fusion protein. Western blot analysis of the fusion protein revealed both monomeric and dimeric species, however the G-CSFR preferentially binds the dimeric molecule. This is true for most of the MBP fusions tested. Presumably the fusion protein is dimerized through intermolecular disulfide bonds between cysteine residues present in the peptide sequence. Cleavage of the peptide from the carboxy terminus of MBP using Factor Xa caused the peptide to lose its bioactivity while retaining its binding activity.

The Ba/F3 G-CSFR reporter cell line was used to measure the potency of:

LLDICELKLQECARRCN (SEQ ID NO: 208)  Ex. 81 and other possible G-CSF receptor antagonists.

Figure 3:
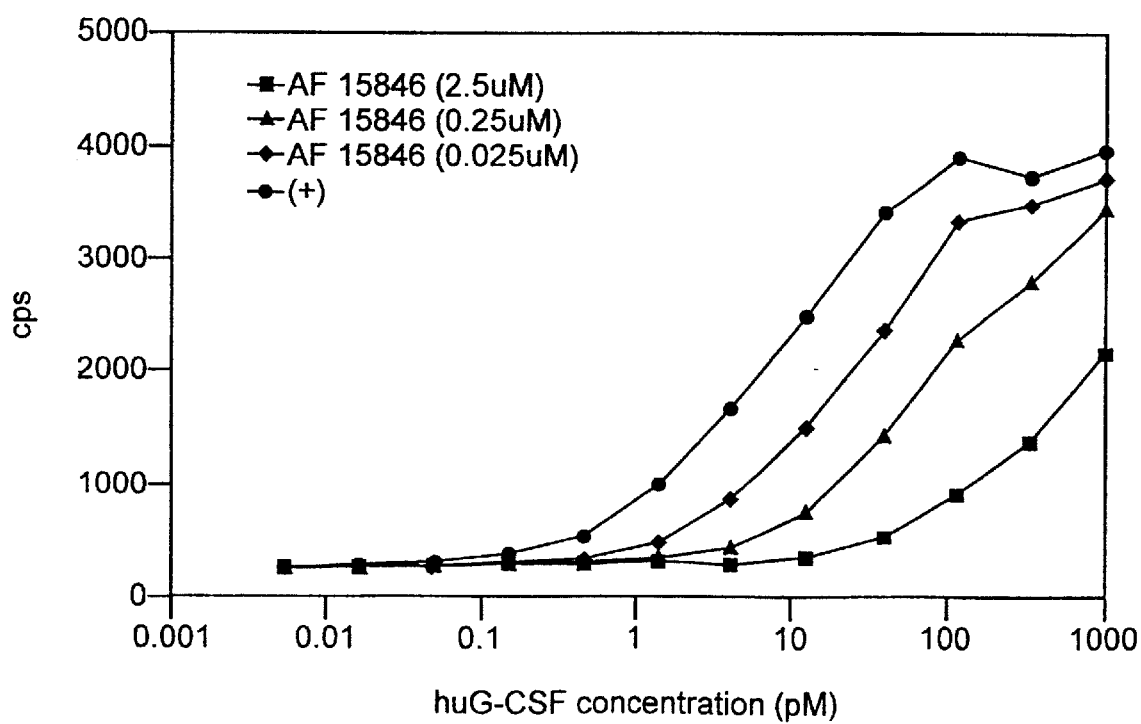

Ligand mediated G-CSF receptor activation in these cells results in the expression of luciferase, providing a detectable biological signal. Ba/F3 G-CSFR reporter cells responded to the addition of G-CSF in a dose dependent manner (FIG. 2). The addition of increasing concentrations of peptide from Example 81 inhibit this G-CSF response, indicating that the peptide is a G-CSFR antagonist (FIG. 3).

EXAMPLE 82

Characterization of the Dimer Form of AF15846

The peptide AF15846, i.e., LLDICELKLQECARRCN (SEQ ID NO: 208), was under study as a G-CSF antagonist for chemoprotection against chemotherapy-induced neutropenia. The peptide monomer contains three Cys residues with a mass of 2020.4 (average). This peptide is not active as a monomer but must be oxidized, putatively to a dimer form, for activity.

Monomer vs. Dimer Forms of AF15846:

AF15846 that had been oxidized in 50 mM Tris, pH 8.0 for 48 hours was diluted with PBS, then injected onto a Superdex peptide gel filtration column equilibrated in PBS at 0.75 mL/min. The results of this chromatography indicated that most of the peptide was in dimer form, with small amounts of monomer remaining (not shown). In contrast, AF15846 that had been stored in acid and then diluted with PBS directly prior to injection onto the peptide column eluted predominantly as a monomer. Some dimerization apparently occurred either during storage or during the short period the peptide was at neutral pH prior to and during size exclusion chromatography. Oxidized peptide also eluted much later from a cation exchange column run in salt gradients at low pH, consistent with dimer formation (not shown).

Reverse Phase HPLC Assay for Oxidation of AF15846:

AF15846 was oxidized by incubation in 50 mM Tris, pH 8.0, for 16 to 48 hours. Reverse phase HPLC methods using a Vydac 25 cm C-18 column and 0.1% TFA/acetonitrile buffers were developed to separate the oxidized dimer from unoxidized monomer, and to separate several different dimerized peptide structures. While both high pH reverse phase and cation exchange chromatography were also investigated, low pH reverse phase separation on a 25 cm column provided the best separation of the many oxidized forms of the peptide (not shown). The dimer species elute from the column with earlier retention times than do the monomer species. Samples of oxidized AF15846 were re-reduced with DTT to confirm the elution order. One additional piece of evidence for the formation of intermolecular dimers comes from the fact that when oxidation was carried out at low (0.25 mg/mL) concentrations of peptide, the reaction apparently did not go to completion.

Oxidation of AF15846 Under Various Conditions:

AF15846 was incubated for 48 hours in 50 mM Tris, pH 8, 20% DMSO in water, 20 mM potassium phosphate, pH 3, or 0.1% TFA at room temperature. Aliquots of each sample were taken at various time points. Oxidation of the monomer peptide in Tris resulted in the presence of one major plus one minor oxidized species after several hours. In contrast, oxidation of the peptide in 20% DMSO in water resulted in a complex mixture of oxidized species, even after the 48 hour incubation. Some oxidation of the peptide was observed even at acidic pH, although to a much lesser extent than that observed with either Tris or DMSO as the oxidant.

Figure 4:
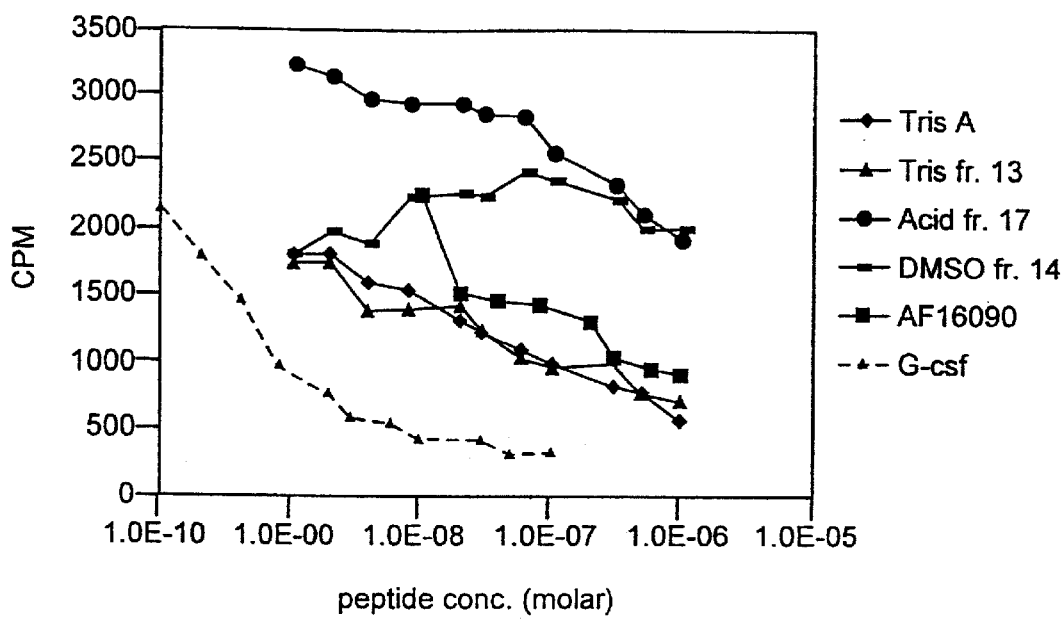

Activity of Oxidized AF15846 Fractions:

Several fractions containing oxidized AF15846 resulting from treatment under the conditions described above were collected subjected to testing in two assays: an $^{125}$I-G-CSF competition binding assay and an ELISA format competitive G-CSF receptor-binding assay. In both cases fractions corresponding to the predominant Tris-oxidized species exhibited the highest activity. The activity of selected fractions in the $^{125}$I-G-CSF competition binding assay is shown in FIG. 4. While species corresponding to the monomer peptide were inactive, matrix-assisted laser desorption/ionization mass spectrometry (MALDI-MS) confirmed that the active, Tris-oxidized species was a peptide dimer.

Determination of the Disulfide Structure of the Active Oxidized Form of AF15846:

It was hypothesized that the active form of AF15846 would contain one intrachain disulfide per peptide monomer and one interchain peptide dimer. The three possibilities for this type of structure are shown below

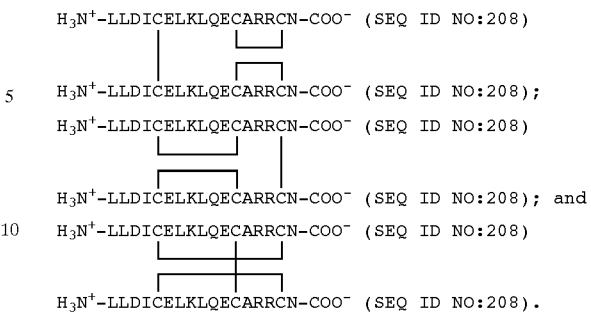

To determine if one of these structures was present in the active form of AF15846, aliquots of Tris-oxidized AF15846 (not HPLC purified) were digested with trypsin and subjected to reverse phase HPLC. Trypsin digestion was carried out using an immobilized enzyme column from Perseptive Biosystems. Digestion was carried out in 25 mM Tris, pH 8, 5 mM $CaCl_2$. Fractions were eluted from the column directly into 0.1% TFA to lower the pH and minimize disulfide scrambling. The resulting tryptic fragments were separated by reverse phase HPLC and analyzed by MALDI mass spectrometry and Edman sequencing. In addition, an aliquot of the digest was analyzed by electrospray liquid chromatography/mass spectrometry (LC/MS). MALDI MS and sequencing of the tryptic peptides indicated the presence of peptides corresponding to disulfide bonds between Cys-5 and Cys-5, as well as between Cys12 and Cys-12. This finding indicated that there were two interchain disulfide bonds between peptide monomers. This result was confirmed by the LC/MS data (FIG. 5), which identified peptides identical to those found by MALDI MS. The typtic peptides are labeled, beginning with the first residue, i.e., Lys, as follows: T1=residues 1–8; T2=residues 9–14; T1,2= residues 1–14; T2,3=residues 9–15; and "+" indicates adisulfide linkage between peptides. However, an additional minor species was evidently present, as a peptide corresponding to a disulfide bond between Cys-5 and Cys-12, which could be either an intrachain or an interchain disulfide, was also seen, albeit at a lower level.

Figure 5:
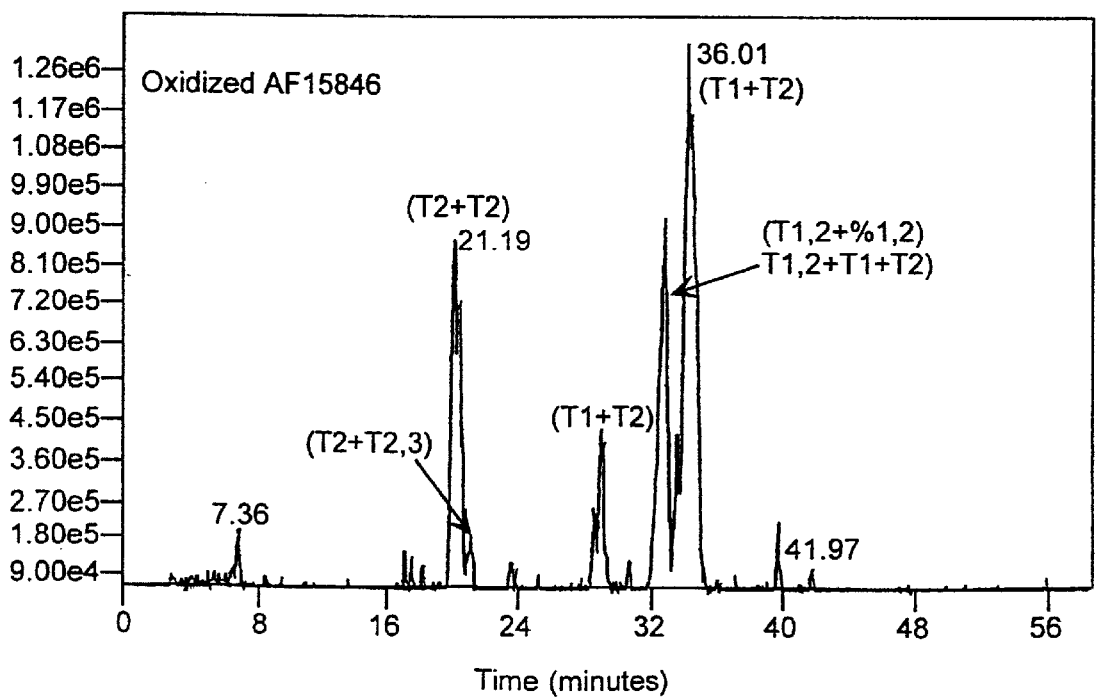
Figure 6:
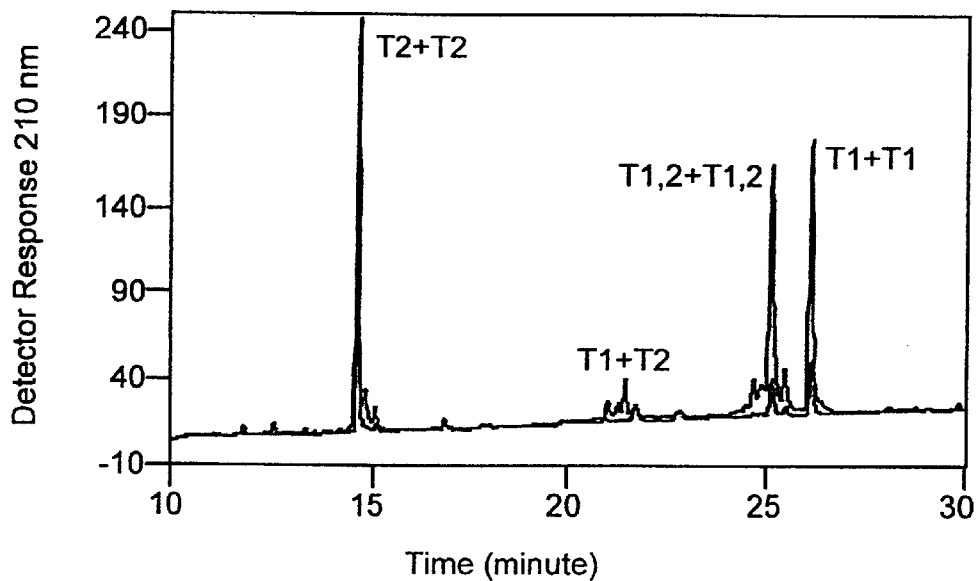

To confirm that the active species contained at least two interchain disulfides, an aliquot of the HPLC-purified, Tris-oxidized AF15846 shown to be active in competition assays was also digested with trypsin. The profile of the purified material was compared to that of the unfractionated Tris oxidation product (FIG. 6, same labeling as in FIG. 5). The HPLC profile indicates that the purified material is lacking a peptide corresponding to a Cys-5 to Cys-12 disulfide-linked fragment. This indicated that the active species contains two interchain disulfide bonds. However, the oxidation state of the remaining Cys-16 in each monomer was not determined.

Figure 7:
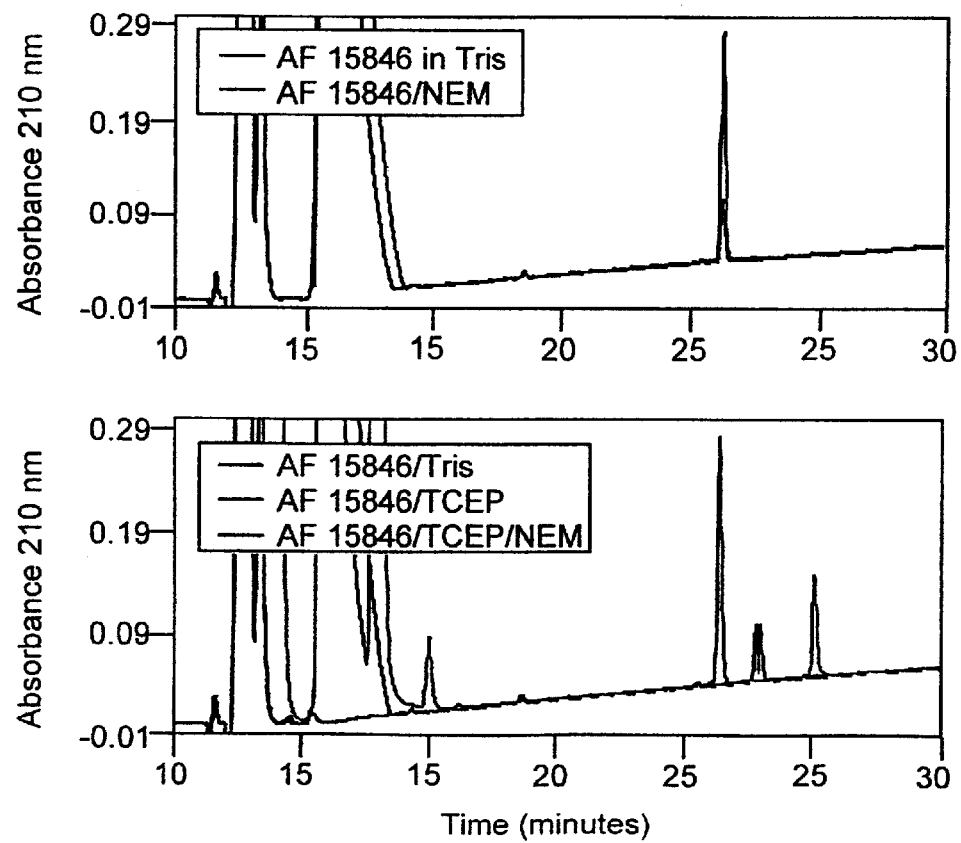

The oxidized peptide was also reacted with N-ethylmaleimide (NEM) at 37° C. for 1 hour in 100 mM ammonium acetate, pH 4.1 to see if any free Cys residues remained in the molecule. If this were the case, treatment with the alkylating reagent would result in a shift of the HPLC retention time. Upon incubation with NEM, no such shift was seen (FIG. 7). In contrast, when the oxidized peptide was incubated with the disulfide specific reducing agent TCEP, also in ammonium acetate, a shift to a later retention time, consistent with reduced peptide, was found. The reduced peptide was modified with NEM to produce a peptide that eluted even later than the reduced form. These data indicate that all six Cys residues in the AF15846 active dimer are involved in disulfide bonds. Since previous results showed that Cys-5 is linked to Cys-5 and Cys-12 is linked to Cys-12, it seems apparent that the remaining two Cys residues at position 16 of the monomer are also involved in an interchain disulfide bond.

Figure 8:
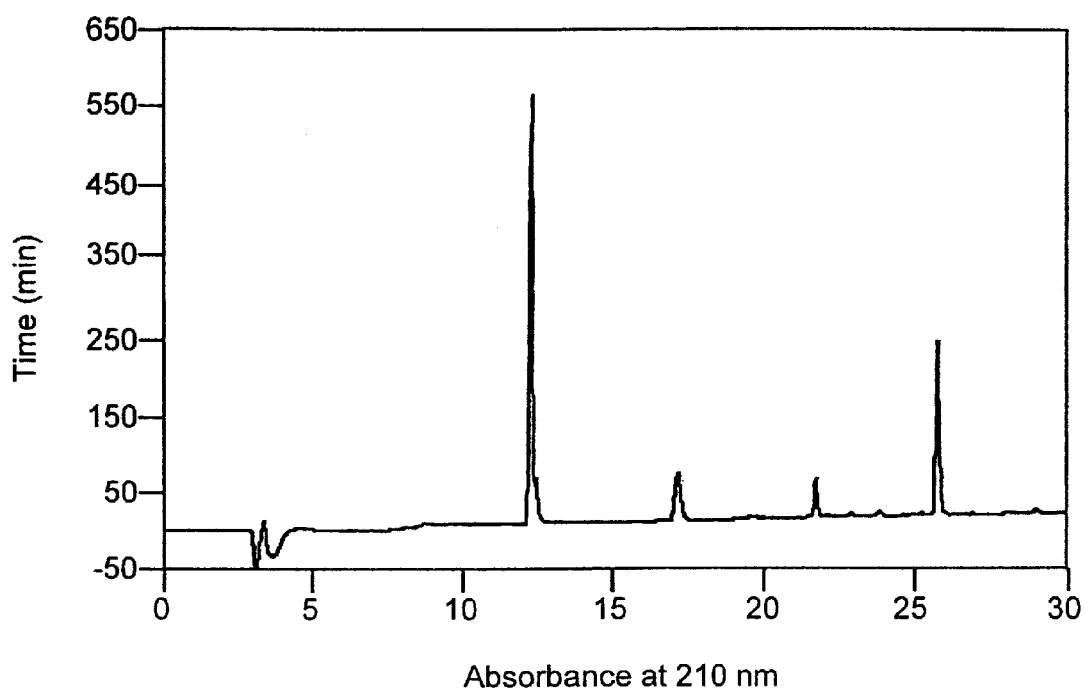
Figure 9A:
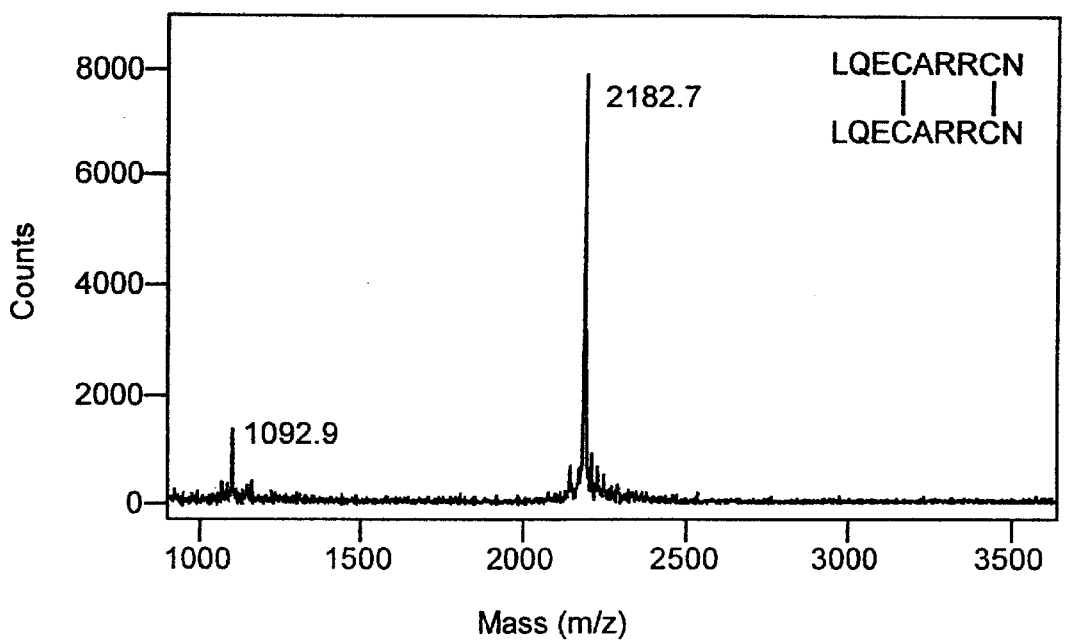
Figure 9B:
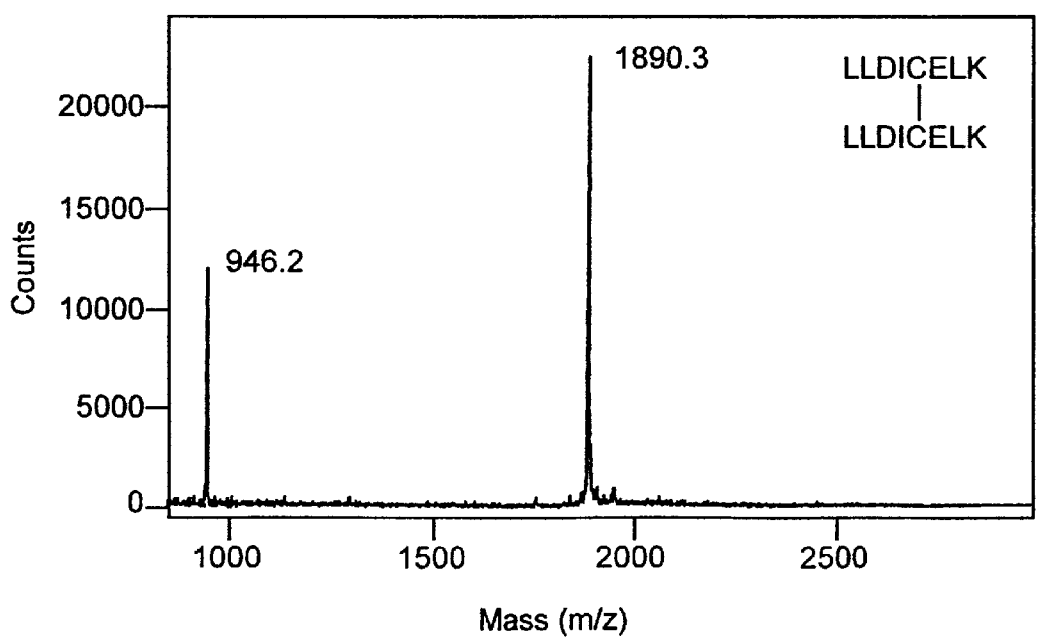

To obtain further information about the disulfide bond structure in active AF15846, the peptide was digested with Lys-C in 50 mM Tris pH 7.0/30% acetontrile. The profile of this digest is shown in FIG. 8. Four major peaks are seen. The first peak corresponds to a dimer of residues 9–17, as indicated by the MALDI MS spectrum of this fraction. See FIGS. 9A and 9B. However, it is not possible to tell with this technique if all four Cys residues are involved in disulfide formation. The last peak contains a dimer of residues 1–8. The remaining two peaks represent intact peptide (22 min) and an artifact peak. This second digest clearly indicates that the peptide dimerizes into a parallel structure.

This three parallel interchain disulfide structure, indicated below, is different than that originally predicted. Note that the arrows represent sites of cleavage by trypsin.

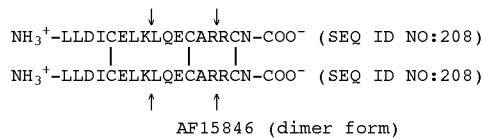

AF15846 (dimer form)

Incubation of the oxidized peptide at 37° C. at higher pH apparently resulted disulfide scrambling and/or degradation of the peptide as control peptide fractions incubated at pH 6.0 or pH 7.5 in parallel with NEM-treated fractions exhibited complex HPLC patterns after incubation. It was necessary to drop to pH 4.1 to obtain clean profiles upon NEM treatment.

Figure 10A:
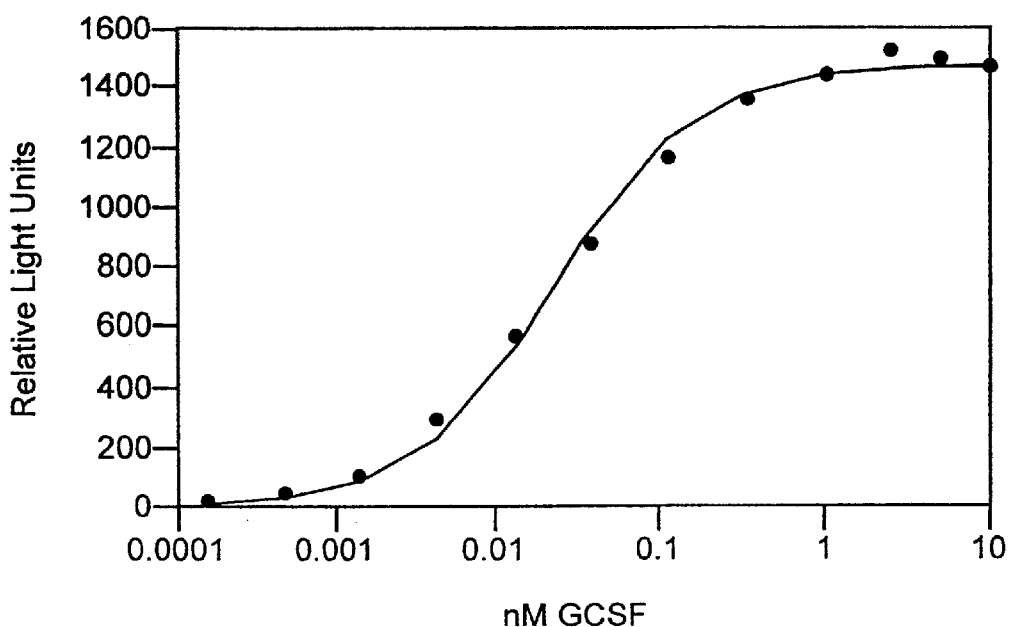
Figure 10B:
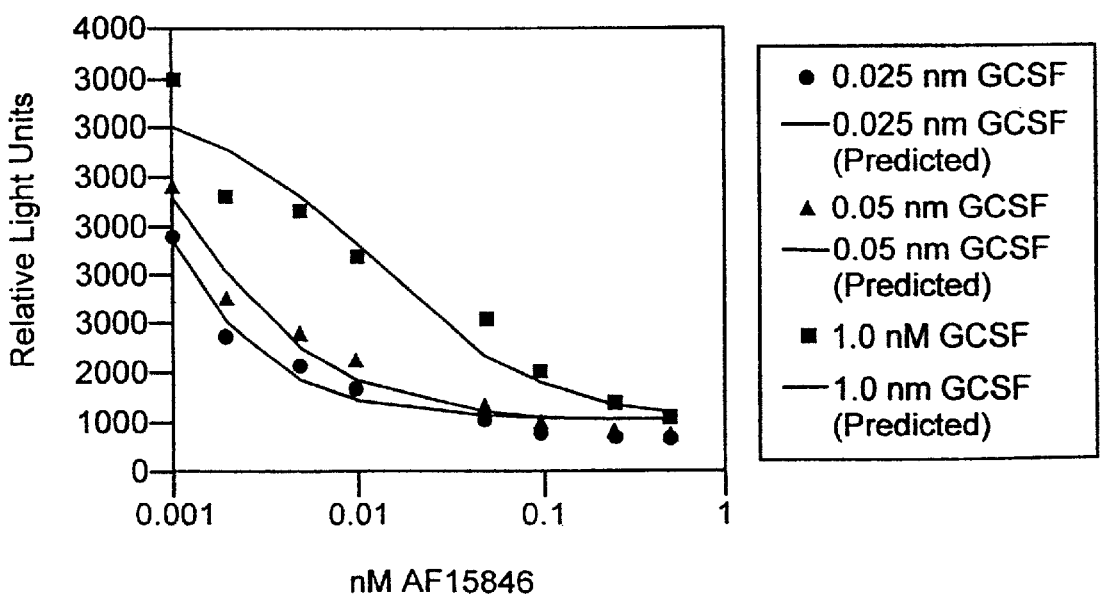
Figure 11:
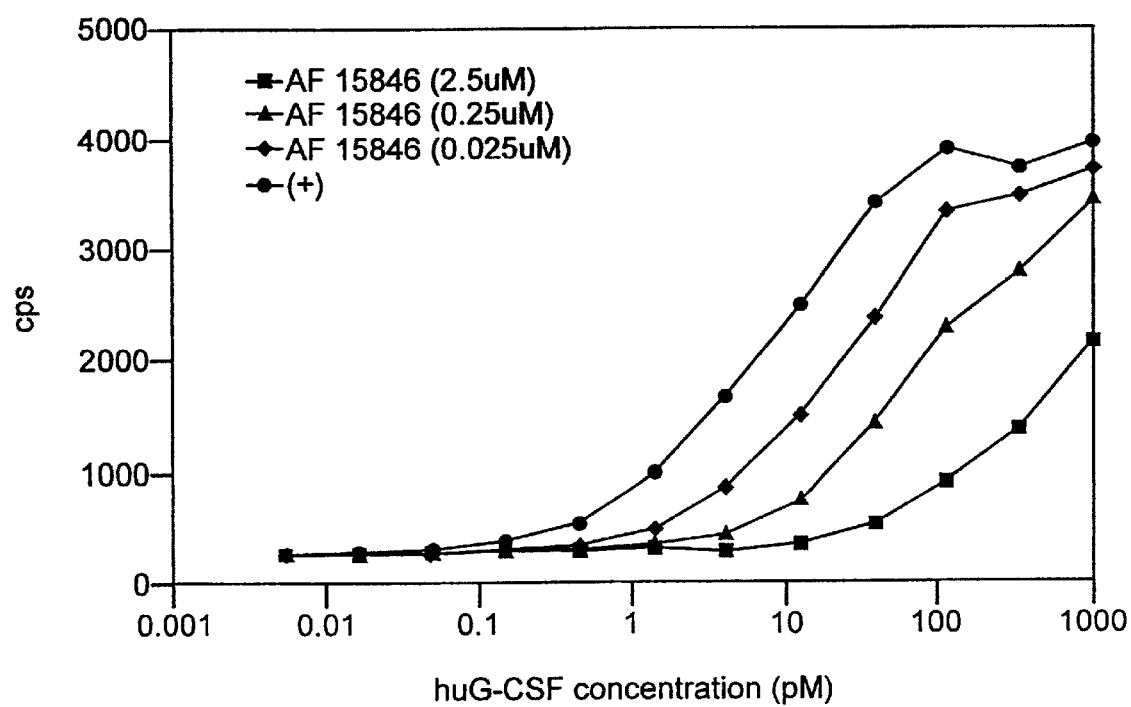

A Bioassay for Determining Activity of G-CSF Antagonists:

A biosassay was used to measure the potency of AF15846 and other possible G-CSF receptor antagonists. This bioassay utilizes a Ba/F3 cell line containing the rhGCSF receptor and a c-fos promoter/luciferase gene construct (Ba/F3/rhGCSF-R/pFos-1cf). Competent binding of a ligand to the receptor results in expression of luciferase as the biological readout. Addition of AF15846 to the assay results in the dose-response curve shifting to higher concentrations, indicating that the peptide is inhibiting the binding of G-CSF to the expressed receptor (FIGS. 10A and 10B). Conversely, the inclusion of various levels of peptide in the assay causes an increase in the amount of G-CSF required to produce a signal, also indicating that the peptide inhibits G-CSF binding (FIG. 11).

What is claimed is:

1. A compound comprising a peptide chain approximately 17 to 40 amino acids in length that binds to G-CSFR and displaces or prevents the binding of G-CSF at the G-CSFR, and contains a sequence of amino acids having the formula LLDICELKLQECARRCN (SEQ ID NO: 208).

2. The compound of claim 1, comprising a dimer having the structure of formula (VIII)

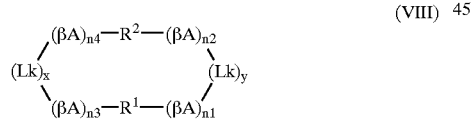

wherein $R^1$ and $R^2$ are independently selected from the sequences of amino acids of formula (V); βA is a β-alanine residue; n1, n2, n3, n4, x and y are independently zero or one with the proviso that the sum of x and y is either one or two; and Lk is a terminal linking moiety selected from the group consisting of a disulfide bond, a carbonyl moiety, a $C_{1-12}$ linking moiety optionally terminated with one or two —NH— linkages and optionally substituted at one or more available carbon atoms with a lower alkyl substituent, a lysine residue or a lysine amide.

3. The compound of claim 1, containing a disulfide bond.

4. The compound of claim 3, having the structure:

5. The compound of claim 1, wherein the N-terminus of the peptide is coupled to a polyethylene glycol molecule.

6. The compound of claim 1, wherein the N-terminus of the peptide is acetylated.

7. The compound of claim 1, wherein the C-terminus of the peptide is amidated.

* * * * *

SEQUENCE LISTING

```
<160> NUMBER OF SEQ ID NOS: 491

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (2)
<223> OTHER INFORMATION: A, N, S, F, D, G, L, T, E, V, P, Q, H, M or K
<221> NAME/KEY: MOD_RES
<222> LOCATION: (3)
<223> OTHER INFORMATION: M, G, R, H, D, I, V, A, S, E, N, F, Y, P, C, W
      or T
<221> NAME/KEY: MOD_RES
<222> LOCATION: (4)
<223> OTHER INFORMATION: E, V, W, F, M, A, N, S, L, T, Y, G or P
<221> NAME/KEY: MOD_RES
<222> LOCATION: (5)
<223> OTHER INFORMATION: V, I, G, Q, W, M, T, Y, L, P, D, C, E or A
<221> NAME/KEY: MOD_RES
<222> LOCATION: (6)
<223> OTHER INFORMATION: M, E, W, L, P, N, I, T, V, F, Y, Q, S, R, W, G,
      H or D
<221> NAME/KEY: MOD_RES
<222> LOCATION: (7)
<223> OTHER INFORMATION: H, A, W, Y, V, F, Q, M, N, E, S, D, P or G
<221> NAME/KEY: MOD_RES
<222> LOCATION: (8)
<223> OTHER INFORMATION: M, F, Y, V, N, L, H, D, S, W, G, Q, C or T
<221> NAME/KEY: MOD_RES
<222> LOCATION: (9)
<223> OTHER INFORMATION: C, Y, R, I, K, W, L, E, M, H, A, T, F, D, P, G
      or Q

<400> SEQUENCE: 1
```

```
Cys Xaa Xaa Xaa Xaa Xaa Xaa Xaa Xaa Cys
 1               5                  10
```

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (1)
<223> OTHER INFORMATION: S, Q, R, L or Y
<221> NAME/KEY: MOD_RES
<222> LOCATION: (2)
<223> OTHER INFORMATION: N, S, T, A or D
<221> NAME/KEY: MOD_RES
<222> LOCATION: (3)
<223> OTHER INFORMATION: E, D or N
<221> NAME/KEY: MOD_RES
<222> LOCATION: (9)
<223> OTHER INFORMATION: L, V, T, P or H

<400> SEQUENCE: 2

```
Xaa Xaa Xaa Ser Gly Trp Val Trp Xaa
 1               5
```

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (3)
<223> OTHER INFORMATION: D, L, S, G, E, A, K or Y
<221> NAME/KEY: MOD_RES
<222> LOCATION: (4)
<223> OTHER INFORMATION: W, Y, F, L or V
<221> NAME/KEY: MOD_RES
<222> LOCATION: (5)
<223> OTHER INFORMATION: F, G, M or L

<400> SEQUENCE: 3

```
Glu Arg Xaa Xaa Xaa Cys
 1               5
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (1)
<223> OTHER INFORMATION: D or E
<221> NAME/KEY: MOD_RES
<222> LOCATION: (5)
<223> OTHER INFORMATION: A or T
<221> NAME/KEY: MOD_RES
<222> LOCATION: (6)
<223> OTHER INFORMATION: Y or V
<221> NAME/KEY: MOD_RES
<222> LOCATION: (8)
<223> OTHER INFORMATION: P or Y

<400> SEQUENCE: 4

```
Xaa Met Val Tyr Xaa Xaa Pro Xaa Trp
 1               5
```

```
<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (2)
<223> OTHER INFORMATION: E, G, P, N, R, T, W, S, L, H, A, Q or Y
<221> NAME/KEY: MOD_RES
<222> LOCATION: (3)
<223> OTHER INFORMATION: S, T, E, A, D, G, W, P, L, N, V, Y, R or M
<221> NAME/KEY: MOD_RES
<222> LOCATION: (4)
<223> OTHER INFORMATION: R, Y, V, Q, E, T, L, P, S, K, M, A or W
<221> NAME/KEY: MOD_RES
<222> LOCATION: (5)
<223> OTHER INFORMATION: L, M, G, F, W, R, S, V, P, A, D, C or T
<221> NAME/KEY: MOD_RES
<222> LOCATION: (6)
<223> OTHER INFORMATION: V, T, A, R, S, L, W, C, I, E, P, H, F, D or Q
<221> NAME/KEY: MOD_RES
<222> LOCATION: (7)
<223> OTHER INFORMATION: E, Y, G, T, Q, M, S, N, A or P
<221> NAME/KEY: MOD_RES
<222> LOCATION: (8)
<223> OTHER INFORMATION: C, V, D, G, L, W, E, V, I, S, M or A
<221> NAME/KEY: MOD_RES
<222> LOCATION: (9)
<223> OTHER INFORMATION: S, Y, A, W, P, V, L, Q, G, K, F, I, E or D
<221> NAME/KEY: MOD_RES
<222> LOCATION: (10)
<223> OTHER INFORMATION: R, W, M, D, H, V, G, A, Q, L, S, E or Y
<221> NAME/KEY: MOD_RES
<222> LOCATION: (11)
<223> OTHER INFORMATION: M, L, I, S, V, P, W, F, T, Y, R or Q

<400> SEQUENCE: 5

Cys Xaa Xaa Xaa Xaa Xaa Xaa Xaa Xaa Xaa Xaa Cys
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (1)
<223> OTHER INFORMATION: E, C, Q, V or Y
<221> NAME/KEY: MOD_RES
<222> LOCATION: (2)
<223> OTHER INFORMATION: E, A, L, M, S, W or Q
<221> NAME/KEY: MOD_RES
<222> LOCATION: (3)
<223> OTHER INFORMATION: K, R, or T
<221> NAME/KEY: MOD_RES
<222> LOCATION: (4)
<223> OTHER INFORMATION: L, A or V
<221> NAME/KEY: MOD_RES
<222> LOCATION: (5)
<223> OTHER INFORMATION: R, A, M, H, E, V, L, G, D, Q or S
<221> NAME/KEY: MOD_RES
<222> LOCATION: (6)
<223> OTHER INFORMATION: E or V
<221> NAME/KEY: MOD_RES
<222> LOCATION: (8)
<223> OTHER INFORMATION: A or G
<221> NAME/KEY: MOD_RES
<222> LOCATION: (9)
<223> OTHER INFORMATION: R, H, G or L

<400> SEQUENCE: 6

Xaa Xaa Xaa Xaa Xaa Xaa Cys Xaa Xaa
```

```
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Formula
      peptide sequence
<221> NAME/KEY: MOD_RES
<222> LOCATION: (1)
<223> OTHER INFORMATION: A, E or G
<221> NAME/KEY: MOD_RES
<222> LOCATION: (2)
<223> OTHER INFORMATION: E, H or D
<221> NAME/KEY: MOD_RES
<222> LOCATION: (3)
<223> OTHER INFORMATION: R or G
<221> NAME/KEY: MOD_RES
<222> LOCATION: (4)
<223> OTHER INFORMATION: K, Y, M, N, Q, R, D, I, S or E
<221> NAME/KEY: MOD_RES
<222> LOCATION: (5)
<223> OTHER INFORMATION: A, S or P
<221> NAME/KEY: MOD_RES
<222> LOCATION: (7)
<223> OTHER INFORMATION: E, D, T, Q, K or A
<221> NAME/KEY: MOD_RES
<222> LOCATION: (8)
<223> OTHER INFORMATION: R, W, K, L, S, A or Q
<221> NAME/KEY: MOD_RES
<222> LOCATION: (9)
<223> OTHER INFORMATION: R or E
<221> NAME/KEY: MOD_RES
<222> LOCATION: (10)
<223> OTHER INFORMATION: W, G or R

<400> SEQUENCE: 7

Xaa Xaa Xaa Xaa Xaa Glu Xaa Xaa Xaa Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Ala Gly Glu Val Met His Met Cys Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asn Arg Glu Ile Glu Ala Met Cys Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Cys Ala Asp Glu Val Met His Phe Cys Cys
  1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Asn Arg Glu Ile Met Trp Met Cys Cys
  1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ser His Glu Val Trp Trp Tyr Cys Cys
  1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Ser Arg Glu Val Leu Tyr Tyr Cys Cys
  1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Phe Ile Glu Gly Pro Trp Val Cys Cys
  1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Phe Val Glu Gly Asn Trp Tyr Cys Cys
  1               5                  10

<210> SEQ ID NO 16
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ala Ala Glu Val Met Val Asn Cys Cys
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ser Asp Glu Val Ile Phe Tyr Cys Cys
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Asp Arg Glu Ile Met Trp Phe Cys Cys
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Ala His Glu Val Met Trp Met Cys Cys
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Gly Ser Glu Val Thr Phe Met Cys Cys
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Leu Glu Glu Ile Met Trp Leu Cys Cys
```

```
                   1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Ala Arg Glu Val Leu Ala Met Cys Cys
  1               5                  10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Ser Val Glu Val Met Gln Met Cys Cys
  1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Thr Asn Val Gln Leu Met His Tyr Cys
  1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Asp Val Trp Gln Leu Phe Asp Arg Cys
  1               5                  10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ser Phe Val Gln Leu Asn Ser Ile Cys
  1               5                  10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 27

Cys Asp Tyr Trp Gln Trp Phe Asp Lys Cys
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Glu Ser Phe Trp Val Glu Leu Trp Cys
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Val Pro Trp Met Phe Tyr Asp Leu Cys
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Asp Pro Trp Met Phe Tyr Asp Leu Cys
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Asp Pro Trp Val Leu Phe Asp Glu Cys
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Asp His Trp Thr Tyr Phe Asp Met Cys
 1               5                  10

<210> SEQ ID NO 33

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Val Val Trp Thr Leu Tyr Asp Lys Cys
  1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Pro Asp Trp Tyr Gln Ser Tyr Met Cys
  1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Pro Asp Trp Tyr Ser Tyr Tyr Met Cys
  1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Pro Glu Trp Tyr Thr Asp Val Met Cys
  1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Pro Asp Trp Tyr Leu Asp Tyr Met Cys
  1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Cys Pro Glu Trp Tyr Leu Asp Tyr Met Cys
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Pro Asp Trp Tyr Leu Pro Tyr Met Cys
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Pro Glu Trp Tyr Leu Pro Tyr Met Cys
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Gln Asp Trp Trp Val Glu Leu Trp Cys
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Pro Asp Trp Tyr Leu Pro Trp Met Cys
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Ala Cys Met Leu Arg Val Val His Cys
 1               5                  10

<210> SEQ ID NO 44
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 44

Cys Gln Arg Ala Gly Tyr Met Leu Ala Cys
  1               5                  10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys His Ala Asn Pro Val Trp Gly Glu Cys
  1               5                  10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Phe Trp Ser Asp Trp Gly Gln Thr Cys
  1               5                  10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Pro His Trp Thr Ser Tyr Tyr Met Cys
  1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Glu Thr Leu Cys Gly Ala Cys Phe Cys
  1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Ala Thr Thr Ile Asn Asp Thr Leu Cys
  1               5                  10

```
<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Leu Asn Tyr Pro His Pro Val Phe Cys
  1               5                  10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Met Asp Gly Glu Met Ala Val Asp Cys
  1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Asn Met Gly Trp Met Ser Trp Pro Cys
  1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Glu Thr Tyr Ala Asp Trp Leu Gly Cys
  1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Asp Pro Trp Met Phe Phe Asp Met Cys
  1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

```
Cys Asp Pro Trp Ile Trp Tyr Asp Leu Cys
 1               5                  10
```

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Cys Asp Pro Trp Ile Met Tyr Asp Arg Cys
 1               5                  10
```

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Cys Asp Pro Trp Val Phe Phe Asp Ile Cys
 1               5                  10
```

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Cys Asp Pro Trp Thr Tyr Tyr Asp Leu Cys
 1               5                  10
```

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Cys Asp Pro Trp Ile Phe Tyr Asp Arg Cys
 1               5                  10
```

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Cys Asp Pro Trp Leu Phe Tyr Asp Leu Cys
 1               5                  10
```

<210> SEQ ID NO 61
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 61

Cys Asp Pro Trp Val Trp Tyr Asp Leu Cys
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Asp Pro Trp Ile Phe Phe Asp Arg Cys
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Asp Pro Trp Met Phe Phe Asp Gln Cys
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Asp Pro Trp Leu Trp Tyr Asp Arg Cys
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Asp Val Trp Val Trp Tyr Asp Gln Cys
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Asp Pro Trp Ile Tyr Tyr Asp Leu Cys
 1               5                  10
```

```
<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Val Pro Trp Thr Leu Phe Asp Leu Cys
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Pro Ala Trp Tyr Leu Glu Tyr Met Cys
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Pro Asp Trp Tyr Leu Glu Tyr Met Cys
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Lys Tyr Trp Gln Trp Phe Asp Lys Cys
 1               5                  10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Asp His Trp Met Trp Tyr Asp Lys Cys
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 72

Gly Cys Asn Arg Glu Ile Glu Ala Met Cys Cys Gly
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Cys Pro Glu Trp Tyr Thr Asp Val Met Cys Gly
 1               5                  10

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn Trp Tyr Cys Met Asp Gly Glu Met Ala Val Asp Cys Glu Ala Thr
 1               5                  10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Gln Ser Cys Asn Met Gly Trp Met Ser Trp Pro Cys Tyr Phe Val
 1               5                  10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Glu Leu Cys Glu Thr Tyr Ala Asp Trp Leu Gly Cys Val Glu Trp
 1               5                  10                  15

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Pro Cys Asp Pro Trp Met Phe Phe Asp Met Cys Glu Arg Trp
 1               5                  10

<210> SEQ ID NO 78
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 78

Leu Arg Gly Cys Asp Pro Trp Ile Trp Tyr Asp Leu Cys Pro Ala Val
 1               5                  10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Leu Cys Asp Pro Trp Ile Phe Tyr Asp Arg Cys Leu Gly Phe
 1               5                  10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Phe Ala Cys Asp Pro Trp Val Phe Phe Asp Ile Cys Gly Tyr Trp
 1               5                  10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Tyr Trp Cys Asp Pro Trp Thr Tyr Tyr Asp Leu Cys Leu Thr Ala
 1               5                  10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Met Trp Thr Cys Asp Pro Trp Ile Phe Tyr Asp Arg Cys Phe Leu Asn
 1               5                  10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Ser Cys Asp Pro Trp Leu Phe Tyr Asp Leu Cys Leu Leu Asp
 1               5                  10                  15
```

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gly Gly Gly Cys Asp Pro Trp Val Trp Tyr Asp Leu Cys Trp Cys Asp
 1               5                  10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Tyr Thr Ser Cys Asp Pro Trp Ile Phe Phe Asp Arg Cys Met Ser Val
 1               5                  10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Asp Pro Tyr Cys Asp Pro Trp Met Phe Phe Asp Gln Cys Ala Tyr Leu
 1               5                  10                  15

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Arg Glu Phe Cys Asp Pro Trp Leu Trp Tyr Asp Arg Cys Leu
 1               5                  10

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Asn Thr Gly Cys Asp Val Trp Val Trp Tyr Asp Gln Cys Phe Ala Met
 1               5                  10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 89

Leu Val Phe Cys Asp Pro Trp Ile Tyr Tyr Asp Leu Cys Met Asp Thr
  1               5                  10                  15

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Cys Ser Phe Val Gln Leu Asn Ser Ile Cys Gly
  1               5                  10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Cys Pro Ala Trp Tyr Leu Glu Tyr Met Cys Gly
  1               5                  10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Cys Pro Asp Trp Tyr Leu Glu Tyr Met Cys Gly
  1               5                  10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Cys Lys Tyr Trp Gln Trp Phe Asp Lys Cys Gly
  1               5                  10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Cys Asp His Trp Met Trp Tyr Asp Lys Cys Gly
  1               5                  10

<210> SEQ ID NO 95
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Asn Glu Ser Gly Trp Val Trp Leu
  1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Ser Asn Ser Gly Trp Val Trp Val
  1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Thr Glu Ser Gly Trp Val Trp Thr
  1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Asn Ser Gly Trp Val Trp Val
  1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Asp Asn Ser Gly Trp Val Trp His
  1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Ser Asp Ser Gly Trp Val Trp Val Pro
```

-continued

```
                1               5                  10

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Gln Ser Asn Ser Gly Trp Val Trp Val Gly Gly Gly Gly Cys
  1               5                  10                  15

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Glu Gln Ser Asn Ser Gly Trp Val Trp Val
  1               5                  10

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Gln Ser Asn Ser Gly Trp Val Trp Val Gly Gly Gly Gly Cys Lys
  1               5                  10                  15

Lys Lys

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Gln Ser Asn Ser Gly Trp Val Trp Val Gly Lys Lys Lys Cys
  1               5                  10                  15

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Gln Ser Asn Ser Gly Trp Val Trp Val Gly Lys Lys Lys
  1               5                  10

<210> SEQ ID NO 106
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 106

Lys Lys Lys Glu Gln Ser Asn Ser Gly Trp Val Trp Val
 1               5                  10

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Gln Ser Asn Ser Gly Trp Val Trp Val Gly Lys Lys Lys Ser Lys
 1               5                  10                  15

Lys Lys

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Gln Ser Asn Ser Gly Trp Val Trp Val Gly Gly Cys Lys Lys Lys
 1               5                  10                  15

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Gln Ser Asn Ser Gly Trp Val Trp Val Gly Gly Gly Gly Gly Gly
 1               5                  10                  15

Cys Lys Lys Lys
            20

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Asn Glu Ser Gly Trp Val Trp Leu Pro
 1               5                  10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 111

Glu Gln Ser Asn Ser Gly Trp Val Trp Val
 1               5                  10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Arg Thr Glu Ser Gly Trp Val Trp Thr
 1               5                  10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Arg Ala Asn Ser Gly Trp Val Trp Val
 1               5                  10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Tyr Asp Asn Ser Gly Trp Val Trp His
 1               5                  10

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Gln Ser Asn Ser Gly Trp Val Trp Val Gly Lys Lys Lys Lys
 1               5                  10                  15

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Gln Ser Asn Ser Gly Trp Val Trp Val Gly Gly Gly Gly Ser Lys
 1               5                  10                  15

Lys Lys

<210> SEQ ID NO 117
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Glu Gln Ser Asn Ser Gly Trp Val Trp Val Gly Gly Gly Gly Ser
  1               5                  10                  15

<210> SEQ ID NO 118
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Glu Gln Ser Asn Ser Gly Trp Val Trp Val Gly Gly Gly Ser Glu
  1               5                  10                  15

Gln Ser Asn Ser Gly Trp Val Trp Val Gly Gly Gly Gly Ser
             20                  25                  30

<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Tyr Gln Ser Phe Glu Leu Ser Asp Ser Gly Trp Val Trp Val Pro
  1               5                  10                  15

Val Ala Arg His
             20

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Arg Asp Trp Phe Cys
  1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Glu Arg Asp Trp Gly Cys
  1               5

<210> SEQ ID NO 122
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 122

Glu Arg Leu Trp Phe Cys
  1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Arg Ser Tyr Phe Cys
  1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Arg Gly Trp Phe Cys
  1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Arg Glu Trp Phe Cys
  1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Arg Ala Trp Phe Cys
  1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Arg Leu Tyr Phe Cys
  1               5
```

```
<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Arg Tyr Phe Met Cys
 1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Arg Leu Phe Leu Cys
 1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Arg Ala Leu Met Cys
 1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Arg Asp Val Met Cys
 1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Glu Arg Lys Trp Phe Cys
 1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 133

Glu Thr Trp Gly Glu Arg Asp Trp Phe Cys
 1               5                  10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Thr Trp Gly Glu Arg Asp Trp Gly Cys
 1               5                  10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Thr Ala Glu Arg Leu Trp Phe Cys Gly
 1               5                  10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Glu Thr Ala Glu Arg Ser Tyr Phe Cys
 1               5                  10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Asp Asn Ala Glu Arg Gly Trp Phe Cys
 1               5                  10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Ser Asn Ser Glu Arg Glu Trp Phe Cys
 1               5                  10

<210> SEQ ID NO 139
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 139

Ser Thr Ser Glu Arg Ala Trp Phe Cys Gly
 1               5                  10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ser Trp Ser Glu Arg Gly Trp Phe Cys
 1               5                  10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Leu Ser Ser Glu Arg Glu Trp Phe Cys
 1               5                  10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Met Gln Gly Glu Arg Gly Trp Phe Cys
 1               5                  10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Ser Ser Glu Arg Ala Trp Phe Cys Gly
 1               5                  10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Asn Met Arg Glu Arg Leu Tyr Phe Cys
 1               5                  10
```

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Pro Asn Arg Glu Arg Tyr Phe Met Cys
  1               5                  10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Val Thr Arg Glu Arg Leu Phe Leu Cys
  1               5                  10

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ile Pro Leu Ser Glu Arg Ala Leu Met Cys Ser Ser Trp Asn Cys
  1               5                  10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp Ala Arg Ser Glu Arg Asp Val Met Cys Leu Ser Tyr Val Cys
  1               5                  10                  15

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Ser Asn Ser Glu Arg Glu Trp Phe Cys Gly
  1               5                  10

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Ser Asn Ser Glu Arg Glu Trp Phe Cys Gly Gly Gly Gly Ser
 1               5                  10                  15

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asn Leu Glu Glu Ala Leu Ala Gln Glu Arg Leu Trp Phe Cys Arg Ser
 1               5                  10                  15

Gly Asn Cys

<210> SEQ ID NO 152
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Leu Glu Ser Tyr Glu Met Glu Glu Arg Lys Trp Phe Cys Lys Met
 1               5                  10                  15

Phe Ser Cys

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Met Val Tyr Ala Tyr Pro Pro Trp
 1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Glu Met Val Tyr Thr Val Pro Tyr Trp
 1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Met Val Tyr Ala Tyr Pro Pro Trp Ser
 1               5                  10

```
<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Glu Met Val Tyr Thr Val Pro Tyr Trp
 1               5                  10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Glu Ser Arg Leu Val Glu Cys Ser Arg Met Cys
 1               5                  10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Glu Thr Tyr Met Thr Tyr Val Tyr Trp Leu Cys
 1               5                  10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Gly Glu Arg Leu Ala Glu Cys Ala Arg Leu Cys
 1               5                  10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Glu Ser Arg Leu Arg Glu Cys Ser Met Leu Cys
 1               5                  10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 161

Cys Glu Ala Arg Leu Ser Glu Cys Ser Arg Ile Cys
 1               5                  10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Pro Ala Arg Leu Leu Glu Cys Ser Arg Met Cys
 1               5                  10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Glu Ser Val Gly Val Gly Asp Trp Trp Ser Cys
 1               5                  10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Glu Asp Arg Leu Val Glu Gly Pro Trp Val Cys
 1               5                  10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Asn Asp Gln Phe Arg Thr Cys Val Asp Val Cys
 1               5                  10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Arg Gly Glu Trp Trp Glu Leu Tyr His Pro Cys
 1               5                  10

<210> SEQ ID NO 167
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Glu Asp Thr Arg Thr Gly Trp Ala Trp Ser Cys
 1               5                  10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Thr Trp Leu Ser Ser Gly Glu Leu Val Trp Cys
 1               5                  10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Trp Pro Pro Val Cys Glu Val Ser Gly Ile Cys
 1               5                  10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Ser Leu Ser Pro Ile Gln Leu Gln His Leu Cys
 1               5                  10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Leu Ala Arg Leu Glu Glu Cys Ser Arg Phe Cys
 1               5                  10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys His Asn Ser Ser Pro Met Val Gly Val Thr Cys
```

```
                     1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys His Val Ser Pro Val Gln Ile Lys Ala Leu Cys
  1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Ala Ala Pro Ala Thr Ser Trp Phe Gln Tyr Cys
  1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Ala Ser Lys Leu His Glu Cys Ser Leu Arg Cys
  1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Glu Pro Met Asp Ser Asn Gly Ile Val Gln Cys
  1               5                   10

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Gln Tyr Ala Ser Ala Ala Asp Glu Gln Arg Cys
  1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 178

Cys Glu Tyr Trp Asp Glu Pro Ser Leu Ser Trp Cys
 1               5                  10

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Glu Arg Glu Cys Phe Gln Met Leu Glu Arg Cys
 1               5                  10

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Gly Met Ser Thr Asp Glu Leu Asp Glu Ile Cys
 1               5                  10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Tyr Val Ser Pro Ser Thr Gly Leu Tyr Ser Cys
 1               5                  10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Glu Ala Arg Leu Val Glu Cys Ser Arg Leu Cys
 1               5                  10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Glu Ser Arg Leu Ser Glu Cys Ser Arg Met Cys
 1               5                  10

<210> SEQ ID NO 184

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Glu Leu Lys Leu Gln Glu Cys Ala Arg Arg Cys
  1               5                  10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Glu Leu Lys Leu Gln Glu Ala Ala Arg Arg Cys
  1               5                  10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Leu Glu Arg Leu Glu Glu Cys Ser Arg Phe Cys
  1               5                  10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Gly Cys Glu Ser Arg Leu Val Glu Cys Ser Arg Met Cys
  1               5                  10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Gly Cys Glu Thr Tyr Met Thr Tyr Val Tyr Trp Leu Cys
  1               5                  10

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189
```

```
Glu Trp Leu Cys Glu Ser Val Gly Val Gly Asp Trp Trp Ser Cys
 1               5                  10                  15
```

<210> SEQ ID NO 190
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

```
Tyr His Pro Cys Glu Asp Arg Leu Val Glu Gly Pro Trp Val Cys Cys
 1               5                  10                  15

Arg Ser
```

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

```
Trp Leu Leu Cys Asn Asp Gln Phe Arg Thr Cys Val Asp Val Cys Asp
 1               5                  10                  15

Asn Val
```

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

```
Ile Ala Glu Cys Arg Gly Glu Trp Trp Glu Leu Tyr His Pro Cys Leu
 1               5                  10                  15

Ala Ala
```

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

```
Thr Trp Tyr Cys Glu Asp Thr Arg Thr Gly Trp Ala Trp Ser Cys Leu
 1               5                  10                  15

Glu Leu
```

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

```
Gln Leu Asp Cys Thr Trp Leu Ser Ser Gly Glu Leu Val Trp Cys Ser
```

```
                1               5                  10                 15
Asp Trp

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Phe Asp Cys Thr Trp Leu Ser Ser Gly Glu Leu Val Trp Cys Ser
  1               5                  10                 15
Asp Trp

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Trp Pro Pro Val Cys Glu Val Ser Gly Ile Cys Ser
  1               5                  10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Cys Gly Cys Ser Leu Ser Pro Ile Gln Leu Gln His Leu Cys
  1               5                  10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Cys Gly Cys His Val Ser Pro Val Gln Ile Lys Ala Leu Cys
  1               5                  10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Cys His Val Ser Pro Val Gln Ile Lys Ala Leu Cys
  1               5                  10

<210> SEQ ID NO 200
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Thr Ser Cys Ala Ala Pro Ala Thr Ser Trp Phe Gln Tyr Cys Val
 1               5                  10                  15

Leu Pro

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Met Asp Cys Ala Ser Lys Leu His Glu Cys Ser Leu Arg Cys Ala
 1               5                  10                  15

Tyr Ala

<210> SEQ ID NO 202
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Val Val Cys Glu Pro Met Asp Ser Asn Gly Ile Val Gln Cys Ser
 1               5                  10                  15

Met Arg

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Asp Val Cys Gln Tyr Ala Ser Ala Ala Asp Glu Gln Arg Cys Leu
 1               5                  10                  15

Arg Ile

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Val Leu Cys Glu Tyr Trp Asp Glu Pro Ser Leu Ser Trp Cys Leu
 1               5                  10                  15

Ser Ser

<210> SEQ ID NO 205
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Gln Cys Glu Arg Glu Cys Phe Gln Met Leu Glu Arg Cys
 1               5                  10

<210> SEQ ID NO 206
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Phe Cys Ser Cys Gly Met Ser Thr Asp Glu Leu Asp Glu Ile Cys Ala
 1               5                  10                  15

Ile Trp

<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Glu Glu Val Cys Tyr Val Ser Pro Ser Thr Gly Leu Tyr Ser Cys Tyr
 1               5                  10                  15

Asp Gln

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Leu Leu Asp Ile Cys Glu Leu Lys Leu Gln Glu Cys Ala Arg Arg Cys
 1               5                  10                  15

Asn

<210> SEQ ID NO 209
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Gly Leu Leu Asp Ile Cys Glu Leu Lys Leu Gln Glu Cys Ala
 1               5                  10                  15

Arg Arg Cys Asn
            20

<210> SEQ ID NO 210
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Arg Thr Gly Gly Gly Leu Leu Asp Ile Cys Glu Leu Lys Leu Gln
 1               5                  10                  15

Glu Cys Ala Arg Arg Cys Asn
            20

<210> SEQ ID NO 211
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Gly Ile Glu Gly Arg Thr Gly Gly Gly Leu Leu Asp Ile Cys Glu
 1               5                  10                  15

Leu Lys Leu Gln Glu Cys Ala Arg Arg Cys Asn
            20                  25

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Leu Leu Asp Ile Cys Glu Leu Lys Leu Gln Glu Ala Ala Arg Arg Cys
 1               5                  10                  15

Asn

<210> SEQ ID NO 213
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Lys Leu Leu Asp Ile Cys Glu Leu Lys Leu Gln Glu Ala Ala Arg Arg
 1               5                  10                  15

Cys Asn

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Glu Lys Leu Arg Glu Cys Ala Arg
 1               5
```

```
<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Glu Ala Arg Leu Ala Glu Cys Ala Arg
  1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Cys Met Lys Leu Met Glu Cys Ala Arg
  1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Glu Leu Arg Leu Arg Glu Cys Ala His
  1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Ala Lys Leu His Glu Cys Ala Arg
  1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Leu Lys Leu Ala Glu Cys Ala Arg
  1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220
```

Glu Ala Arg Leu Glu Glu Cys Ala Arg
 1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Glu Ala Lys Leu Arg Glu Cys Ala Arg
 1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Glu Leu Arg Leu Ala Glu Cys Ala Arg
 1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Glu Ser Arg Leu Ala Glu Cys Ala Arg
 1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Glu Ala Lys Leu Val Glu Cys Ala Arg
 1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Glu Ser Arg Leu Arg Glu Cys Ala Arg
 1               5

<210> SEQ ID NO 226
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 226

Glu Ala Lys Leu Ala Glu Cys Ala Arg
 1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gln Trp Arg Leu Glu Glu Cys Ala Arg
 1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Leu Arg Leu Glu Glu Cys Ala Arg
 1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Leu Arg Leu Glu Glu Cys Ala Arg
 1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Ala Lys Leu Leu Glu Cys Ala Arg
 1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Ala Arg Ala Gly Val Cys Ala Gly
 1               5
```

```
<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Glu Ala Lys Ala Gly Val Cys Ala Gly
  1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Val Ala Arg Leu Glu Glu Cys Ala Arg
  1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Glu Leu Lys Leu Asp Glu Cys Ala Arg
  1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Glu Trp Arg Leu Gln Glu Cys Ala Arg
  1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Glu Ala Lys Leu Ser Glu Cys Ala Arg
  1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 237

Glu Ala Arg Leu Ser Glu Cys Ala Arg
  1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Leu Lys Leu Leu Glu Cys Ala Arg
  1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Glu Leu Arg Leu Gln Glu Cys Gly Arg
  1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Glu Gln Lys Leu Ala Glu Cys Ala Arg
  1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Glu Leu Arg Leu Gln Glu Cys Ala Arg
  1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Glu Leu Lys Leu Glu Glu Cys Ala Arg
  1               5

<210> SEQ ID NO 243
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 243

Glu Ser Arg Leu Glu Glu Cys Ala Arg
 1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Glu Ala Thr Val Gln Glu Cys Ala Arg
 1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Glu Leu Lys Leu Gln Glu Cys Ala Arg
 1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Tyr Ser Arg Leu Glu Glu Cys Gly Arg
 1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Glu Leu Arg Leu Arg Glu Cys Ala Leu
 1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Ala Arg Leu Leu Glu Cys Ala Arg
 1               5

```
<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Glu Ser Arg Leu Leu Glu Cys Ala Arg
  1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Val Leu Lys Leu Glu Glu Cys Ala Arg
  1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Ser Lys Leu Ala Glu Cys Ala Arg
  1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Ser Lys Leu Arg Glu Cys Ala Arg
  1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Tyr Lys Leu Gly Glu Cys Ala Arg
  1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 254

Glu Ser Arg Leu Gln Glu Cys Ala Arg
  1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gln Ala Arg Leu Ala Glu Cys Ala Arg
  1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Glu Leu Lys Lys Gln Glu Cys Ala Arg
  1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Ser Arg Leu Ser Glu Cys Ala Arg
  1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Glu Ala Arg Leu Glu Glu Cys Gly Arg
  1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Glu Ser Arg Leu Ala Glu Cys Gly Arg
  1               5

<210> SEQ ID NO 260
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Glu Trp Arg Leu Glu Glu Cys Ala Arg
  1               5

<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Glu Ala Arg Leu Ser Glu Cys Gly Arg
  1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Ala Arg Leu Ala Glu Cys Ala Arg
  1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Glu Trp Lys Leu Ala Glu Cys Ala Arg
  1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Glu Ser Lys Leu Glu Glu Cys Ala Arg
  1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Val Lys Leu Ala Glu Cys Ala Arg
```

```
<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Glu Leu Gln Leu Glu Glu Cys Ala Arg
 1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Glu Tyr Lys Leu Ala Ser Cys Ala Arg
 1               5

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Arg Leu Ser Ile Cys Glu Glu Lys Leu Arg Glu Cys Ala Arg Gly Cys
 1               5                  10                  15

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Pro Leu Thr Thr Cys Glu Ala Arg Leu Ala Glu Cys Ala Arg Gln Leu
 1               5                  10                  15

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Leu Ala Leu Cys Met Lys Leu Met Glu Cys Ala Arg Arg Tyr
 1               5                  10

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 271

Glu Leu Val Met Cys Glu Leu Arg Leu Arg Glu Cys Ala His Arg Ala
 1               5                  10                  15

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Pro Leu Ala Arg Cys Glu Ala Lys Leu His Glu Cys Ala Arg Gln Leu
 1               5                  10                  15

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Leu Ser Val Cys Glu Leu Lys Leu Ala Glu Cys Ala Arg Ser Lys
 1               5                  10                  15

<210> SEQ ID NO 274
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Leu Glu Trp Cys Glu Ala Arg Leu Glu Glu Cys Ala Arg Arg Cys
 1               5                  10                  15

<210> SEQ ID NO 275
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Leu Arg Val Val Glu Ala Lys Leu Arg Glu Cys Ala Arg Gly Arg
 1               5                  10                  15

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Val Ala His Leu Glu Leu Arg Leu Ala Glu Cys Ala Arg Gln Ile
 1               5                  10                  15

<210> SEQ ID NO 277

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

His Leu Ala Arg Cys Glu Ser Arg Leu Ala Glu Cys Ala Arg Gln Leu
 1               5                  10                  15

<210> SEQ ID NO 278
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Leu Ala Leu Leu Glu Ala Lys Leu Val Glu Cys Ala Arg Arg Leu
 1               5                  10                  15

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Leu Phe Ser Leu Glu Ser Arg Leu Arg Glu Cys Ala Arg Arg Val
 1               5                  10                  15

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Val Pro Val Leu Glu Ala Lys Leu Ala Glu Cys Ala Arg Arg Phe
 1               5                  10                  15

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Tyr Leu Gln Gln Leu Gln Trp Arg Leu Glu Glu Cys Ala Arg Gly Met
 1               5                  10                  15

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282
```

```
Tyr Leu Glu Leu Cys Gln Leu Arg Leu Glu Glu Cys Ala Arg Gln Phe
  1               5                   10                  15
Asn

<210> SEQ ID NO 283
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Leu His Ile Cys Glu Leu Arg Leu Glu Glu Cys Ala Arg Gly Arg
  1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Val Ala Arg Cys Glu Leu Arg Leu Ala Glu Cys Ala Arg Lys Ser
  1               5                   10                  15

<210> SEQ ID NO 285
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Tyr Leu Glu Val Leu Glu Ser Arg Leu Ala Glu Cys Ala Arg Trp Lys
  1               5                   10                  15

<210> SEQ ID NO 286
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Glu Ala Lys Leu Leu Glu Cys Ala Arg Ala Arg
  1               5                   10

<210> SEQ ID NO 287
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Glu Leu Ser Leu Cys Glu Ala Arg Ala Gly Val Cys Ala Gly Ser Val
  1               5                   10                  15
Thr Lys

<210> SEQ ID NO 288
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Glu Leu Ser Leu Cys Glu Ala Lys Ala Gly Val Cys Ala Gly Ser Val
  1               5                  10                  15

Thr Lys

<210> SEQ ID NO 289
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Leu Trp Gln Cys Val Ala Arg Leu Glu Glu Cys Ala Arg Ser Arg
  1               5                  10                  15

<210> SEQ ID NO 290
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Cys Leu Lys Ser Cys Glu Leu Lys Leu Asp Glu Cys Ala Arg Arg Met
  1               5                  10                  15

<210> SEQ ID NO 291
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Leu Gln Thr Cys Glu Trp Arg Leu Gln Glu Cys Ala Arg Ser Arg
  1               5                  10                  15

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Tyr Ile Ser Gln Cys Glu Ala Lys Leu Ala Glu Cys Ala Arg Leu Tyr
  1               5                  10                  15

<210> SEQ ID NO 293
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 293

Glu Leu Ser Ser Cys Glu Ala Lys Leu Ser Glu Cys Ala Arg Arg Trp
 1               5                  10                  15

<210> SEQ ID NO 294
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Glu Leu Ser Ser Cys Glu Ala Arg Leu Ser Glu Cys Ala Arg Arg Trp
 1               5                  10                  15

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gln Leu Leu Gln Cys Glu Leu Lys Leu Leu Glu Cys Ala Arg Gln Gly
 1               5                  10                  15

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Glu Leu Leu Arg Cys Glu Ala Arg Leu Ala Glu Cys Ala Arg Gly Cys
 1               5                  10                  15

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gln Leu Arg Gln Cys Glu Leu Arg Leu Gln Glu Cys Gly Arg His Gly
 1               5                  10                  15

Asn

<210> SEQ ID NO 298
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Pro Leu Thr Ser Cys Glu Gln Lys Leu Ala Glu Cys Ala Arg Arg Phe
 1               5                  10                  15

<210> SEQ ID NO 299
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Leu Leu Gly Met Cys Glu Leu Arg Leu Gln Glu Cys Ala Arg Ala Lys
 1               5                  10                  15

<210> SEQ ID NO 300
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Leu Ser Arg Cys Glu Leu Lys Leu Glu Glu Cys Ala Arg Gly Met
 1               5                  10                  15

<210> SEQ ID NO 301
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Cys Arg Pro Cys Glu Ser Arg Leu Glu Glu Cys Ala Arg Arg Leu
 1               5                  10                  15

<210> SEQ ID NO 302
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Arg Leu Ser Val Cys Glu Ala Arg Leu Glu Glu Cys Ala Arg Gln Leu
 1               5                  10                  15

<210> SEQ ID NO 303
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Pro Leu Lys Met Cys Glu Ala Thr Val Gln Glu Cys Ala Arg Leu Ile
 1               5                  10                  15

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304
```

Leu Leu Leu Phe Cys Glu Ala Arg Leu Ser Glu Cys Ala Arg His Val
 1               5                  10                  15

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Leu Ser Met Cys Glu Ala Arg Leu Ala Glu Cys Ala Arg Leu Leu
 1               5                  10                  15

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Pro Leu Phe Ser Cys Glu Leu Lys Leu Gln Glu Cys Ala Arg Arg Cys
 1               5                  10                  15

Asn

<210> SEQ ID NO 307
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Leu Glu Arg Cys Tyr Ser Arg Leu Glu Glu Cys Gly Arg Arg Ile
 1               5                  10                  15

<210> SEQ ID NO 308
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Pro Leu Thr Ser Cys Glu Leu Arg Leu Arg Glu Cys Ala Leu Arg Ser
 1               5                  10                  15

Asn

<210> SEQ ID NO 309
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Lys Leu Ala Ala Cys Glu Leu Lys Leu Ala Glu Cys Ala Arg Arg Trp
 1               5                  10                  15

<210> SEQ ID NO 310

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Lys Leu Ala Ala Cys Glu Leu Arg Leu Ala Glu Cys Ala Arg Arg Trp
 1               5                  10                  15

<210> SEQ ID NO 311
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Leu Thr Arg Cys Glu Leu Arg Leu Ala Glu Cys Ala Arg Lys Ile
 1               5                  10                  15

<210> SEQ ID NO 312
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Leu Leu Gln Gln Cys Glu Leu Lys Leu Ala Glu Cys Ala Arg Ser Ile
 1               5                  10                  15

<210> SEQ ID NO 313
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Leu Trp Gln Cys Glu Ala Arg Leu Leu Glu Cys Ala Arg Arg Ser
 1               5                  10                  15

<210> SEQ ID NO 314
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Arg Leu Arg Leu Cys Glu Ser Arg Leu Leu Glu Cys Ala Arg Ser Leu
 1               5                  10                  15

<210> SEQ ID NO 315
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315
```

```
Gln Leu Glu Thr Cys Val Leu Lys Leu Glu Glu Cys Ala Arg Arg Cys
 1               5                  10                  15
Asn
```

<210> SEQ ID NO 316
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

```
Ala Leu Ser Gln Cys Glu Leu Arg Leu Ala Glu Cys Ala Arg Ser Val
 1               5                  10                  15
Thr Lys
```

<210> SEQ ID NO 317
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

```
Glu Leu Lys Leu Ala Glu Cys Ala Arg Arg Ser
 1               5                  10
```

<210> SEQ ID NO 318
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

```
Ala Leu Ser Arg Cys Glu Ser Lys Leu Ala Glu Cys Ala Arg Arg Gln
 1               5                  10                  15
```

<210> SEQ ID NO 319
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

```
Leu Met Ser Thr Cys Glu Ser Lys Leu Arg Glu Cys Ala Arg Ser Leu
 1               5                  10                  15
```

<210> SEQ ID NO 320
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Ser Leu Gln Arg Cys Glu Tyr Lys Leu Gly Glu Cys Ala Arg Ser Leu
 1               5                  10                  15
```

<210> SEQ ID NO 321

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Arg Leu Glu Leu Leu Glu Ser Arg Leu Gln Glu Cys Ala Arg Gln Leu
 1               5                  10                  15
Asn

<210> SEQ ID NO 322
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Met Glu Trp Cys Gln Ala Arg Leu Ala Glu Cys Ala Arg Cys Cys
 1               5                  10                  15
Asn

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Pro Leu Phe Ser Cys Glu Leu Lys Lys Gln Glu Cys Ala Arg Arg Cys
 1               5                  10                  15
Asn

<210> SEQ ID NO 324
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Leu Leu Asp Lys Cys Glu Ser Arg Leu Ser Glu Cys Ala Arg Arg Leu
 1               5                  10                  15

<210> SEQ ID NO 325
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Leu Leu Ala Arg Cys Glu Ala Arg Leu Glu Glu Cys Gly Arg Gln Cys
 1               5                  10                  15

<210> SEQ ID NO 326
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 326

Asp Leu Leu Tyr Cys Glu Ser Arg Leu Ala Glu Cys Gly Arg Met
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ala Leu Gln Met Cys Glu Trp Arg Leu Glu Glu Cys Ala Arg Arg Leu
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Leu Leu Thr Met Cys Glu Ala Arg Leu Ser Glu Cys Gly Arg Arg Leu
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ala Leu Trp Arg Cys Glu Ser Arg Leu Ala Glu Cys Ala Arg Arg Ser
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Leu Leu Ala Thr Cys Ala Ala Arg Leu Ala Glu Cys Ala Arg Gln Leu
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Leu Gln Thr Cys Glu Trp Lys Leu Ala Glu Cys Ala Arg Ser Asn
1               5                   10                  15
```

```
<210> SEQ ID NO 332
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Pro Leu Arg Ser Cys Glu Ser Lys Leu Glu Glu Cys Ala Arg Gln Leu
 1               5                  10                  15

<210> SEQ ID NO 333
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Cys Leu Arg Ala Leu Asp Val Lys Leu Ala Glu Cys Ala Arg His Leu
 1               5                  10                  15

<210> SEQ ID NO 334
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Leu Lys Thr Leu Glu Leu Gln Leu Glu Glu Cys Ala Arg Arg Ser
 1               5                  10                  15

<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Lys Leu Arg Asp Val Glu Leu Lys Leu Ala Glu Cys Ala Arg Arg Ser
 1               5                  10                  15

<210> SEQ ID NO 336
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ser Leu Gln Arg Cys Glu Tyr Lys Leu Ala Ser Cys Ala Arg Ser Leu
 1               5                  10                  15

<210> SEQ ID NO 337
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 337

Arg Leu Ala Arg Cys Glu Leu Arg Leu Ala Glu Cys Ala Arg Lys Ser
 1               5                  10                  15

<210> SEQ ID NO 338
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Leu Trp Tyr Leu Glu Ser Lys Leu Glu Glu Cys Ala Arg Arg Cys
 1               5                  10                  15

Asn

<210> SEQ ID NO 339
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Leu Trp Tyr Leu Glu Ser Lys Leu Glu Glu Cys Ala Arg Arg Ala
 1               5                  10                  15

Asn Gly

<210> SEQ ID NO 340
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asp Leu Trp Tyr Leu Glu Ser Lys Leu Glu Glu Cys Ala Arg Arg Cys
 1               5                  10                  15

Asn Gly

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Lys Gln Arg Glu Leu Glu Leu Lys Leu Ala Glu Cys Ala Arg Arg Ser
 1               5                  10                  15

<210> SEQ ID NO 342
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Gln Met Gln Glu Trp Cys Ala Arg Leu Ala Glu Cys Ala Arg Cys Cys

```
                 1               5                  10                 15
Asn

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Leu Leu Asp Ile Cys Glu Leu Lys Leu Gln Glu Cys Ala Arg Arg Ala
 1               5                  10                 15
Asn

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ala Glu Arg Lys Ala Glu Glu Arg Arg Trp
 1               5                  10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ala Glu Arg Tyr Ala Glu Glu Arg Glu Gly
 1               5                  10

<210> SEQ ID NO 346
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ala Glu Arg Met Ala Glu Glu Arg Arg Trp
 1               5                  10

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ala Glu Arg Lys Ala Glu Glu Arg Arg Arg
 1               5                  10

<210> SEQ ID NO 348
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala His Arg Asn Ala Glu Glu Arg Arg Trp
 1               5                  10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ala Glu Arg Lys Ser Glu Asp Trp Arg Trp
 1               5                  10

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ala Glu Arg Lys Ala Glu Glu Lys Arg Arg
 1               5                  10

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ala Glu Arg Gln Ala Glu Thr Arg Arg Trp
 1               5                  10

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ala Glu Arg Asn Ala Glu Glu Arg Arg Trp
 1               5                  10

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ala Glu Arg Gln Ala Glu Glu Arg Arg Trp
```

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ala Glu Arg Arg Ala Glu Glu Arg Arg Trp
 1               5                  10

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Glu Arg Asp Ala Glu Gln Arg Arg Trp
 1               5                  10

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Glu Arg Ile Ala Glu Glu Arg Arg Trp
 1               5                  10

<210> SEQ ID NO 357
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ala Glu Arg Ser Ala Glu Glu Arg Arg Trp
 1               5                  10

<210> SEQ ID NO 358
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ala Glu Arg Lys Ala Glu Glu Leu Arg Trp
 1               5                  10

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Ala Glu Arg Lys Ala Glu Glu Ser Arg Trp
 1               5                   10

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Glu Glu Arg Lys Ala Glu Glu Arg Arg Trp
 1               5                   10

<210> SEQ ID NO 361
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ala Asp Gly Lys Ala Glu Glu Arg Arg Trp
 1               5                   10

<210> SEQ ID NO 362
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala Asp Gly Lys Ala Glu Glu Leu Arg Trp
 1               5                   10

<210> SEQ ID NO 363
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Asp Gly Met Pro Glu Glu Arg Arg Trp
 1               5                   10

<210> SEQ ID NO 364
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ala Asp Gly Glu Ala Glu Lys Arg Arg Trp
 1               5                   10

<210> SEQ ID NO 365

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Asp Gly Asn Ala Glu Glu Arg Arg Trp
 1               5                  10

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Asp Gly Glu Ala Glu Lys Ala Arg Trp
 1               5                  10

<210> SEQ ID NO 367
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Glu Gly Glu Ala Glu Lys Ala Arg Trp
 1               5                  10

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Glu Arg Lys Ala Glu Glu Arg Arg Trp
 1               5                  10

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Glu Arg Glu Ala Glu Glu Arg Arg Trp
 1               5                  10

<210> SEQ ID NO 370
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370
```

```
Ala Asp Gly Glu Ala Glu Ala Arg Arg Trp
 1               5                   10

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ala Asp Gly Arg Ala Glu Glu Ala Arg Trp
 1               5                   10

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Glu Gly Arg Ala Glu Glu Ala Arg Trp
 1               5                   10

<210> SEQ ID NO 373
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ala Glu Arg Glu Ala Glu Lys Ala Arg Trp
 1               5                   10

<210> SEQ ID NO 374
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ala Glu Arg Lys Ala Glu Glu Gln Arg Trp
 1               5                   10

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Glu Arg Asp Ala Glu Lys Arg Arg Trp
 1               5                   10

<210> SEQ ID NO 376
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 376

Ala Glu Arg Glu Ala Glu Lys Leu Arg Trp
 1               5                  10

<210> SEQ ID NO 377
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Met Leu Ala Glu Arg Lys Ala Glu Glu Arg Arg Trp Phe Asn Thr His
 1               5                  10                  15

Gly Arg Glu

<210> SEQ ID NO 378
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Met Leu Ala Glu Arg Lys Ala Glu Glu Arg Arg Trp Phe Asn Thr His
 1               5                  10                  15

Gly Arg Glu Lys
            20

<210> SEQ ID NO 379
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Gly Gly Met Leu Ala Glu Arg Lys Ala Glu Glu Arg Arg Trp Phe
 1               5                  10                  15

Asn Thr His Gly Arg Glu
            20

<210> SEQ ID NO 380
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Cys Met Leu Ala Glu Arg Lys Ala Glu Glu Arg Arg Trp Phe Asn Thr
 1               5                  10                  15

His Gly Arg Glu
            20

<210> SEQ ID NO 381
<211> LENGTH: 21
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 381

Cys Met Leu Ala Glu Arg Lys Ala Glu Glu Arg Arg Trp Phe Asn Thr
 1               5                  10                  15

His Gly Arg Glu Lys
            20

<210> SEQ ID NO 382
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Met Leu Ala Glu Arg Tyr Ala Glu Glu Arg Glu Gly Phe Asn Met Gln
 1               5                  10                  15

Trp Arg Glu

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Met Leu Ala Glu Arg Met Ala Glu Glu Arg Arg Trp Phe Arg Arg Met
 1               5                  10                  15

Gly

<210> SEQ ID NO 384
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ile Val Ala Glu Arg Lys Ala Glu Glu Arg Arg Arg Leu Asn Thr Glu
 1               5                  10                  15

Gly His Glu

<210> SEQ ID NO 385
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ile Leu Ala His Arg Asn Ala Glu Glu Arg Arg Trp Phe Gln Lys His
 1               5                  10                  15

Gly Arg

<210> SEQ ID NO 386

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Met Leu Ala Glu Arg Lys Ser Glu Asp Trp Arg Trp Leu Lys Thr His
  1               5                  10                  15

Gly Arg Asp

<210> SEQ ID NO 387
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Met Leu Ala Glu Arg Lys Ala Glu Glu Lys Arg Arg Leu Lys Thr Gln
  1               5                  10                  15

Gly Arg Glu

<210> SEQ ID NO 388
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ile Leu Ala Glu Arg Gln Ala Glu Thr Arg Arg Trp Met Arg Asn Ala
  1               5                  10                  15

Gly Ser Val Thr Lys
             20

<210> SEQ ID NO 389
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Met Leu Ala Glu Arg Asn Ala Glu Glu Arg Arg Trp Leu Lys Arg Gln
  1               5                  10                  15

Cys Gly

<210> SEQ ID NO 390
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Met Leu Ala Glu Arg Gln Ala Glu Glu Arg Arg Trp Leu Lys Met His
  1               5                  10                  15

Gly Gly Glu
```

```
<210> SEQ ID NO 391
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Met Leu Ala Glu Arg Arg Ala Glu Glu Arg Arg Trp Leu Lys Thr Gln
  1               5                  10                  15

Gly Gly Asp

<210> SEQ ID NO 392
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Met Leu Ala Glu Arg Gln Ala Glu Glu Arg Arg Trp Leu Lys Thr Gln
  1               5                  10                  15

Gly Arg Asp

<210> SEQ ID NO 393
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Met Leu Ala Glu Arg Lys Ala Glu Glu Arg Arg Trp Phe Lys Thr His
  1               5                  10                  15

Gly Arg Glu

<210> SEQ ID NO 394
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Met Leu Ala Glu Arg Lys Ala Glu Glu Arg Arg Trp Phe Asn Asn Gln
  1               5                  10                  15

Gly Arg Glu

<210> SEQ ID NO 395
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Met Pro Ala Glu Arg Asp Ala Glu Gln Arg Arg Trp Leu Lys Thr His
  1               5                  10                  15

Gly Arg Glu
```

<210> SEQ ID NO 396
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 396

Ile Leu Ala Glu Arg Ile Ala Glu Glu Arg Arg Trp Leu Lys Thr Gln
 1               5                  10                  15

Gly Arg

<210> SEQ ID NO 397
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

Met Leu Ala Glu Arg Lys Ala Glu Glu Arg Arg Trp Leu Gln Thr His
 1               5                  10                  15

Gly Arg Glu

<210> SEQ ID NO 398
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 398

Ile Leu Ala Glu Arg Ser Ala Glu Glu Arg Arg Trp Leu Lys Thr Gln
 1               5                  10                  15

Gly Arg Glu

<210> SEQ ID NO 399
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 399

Leu Leu Ala Glu Arg Lys Ala Glu Glu Leu Arg Trp Leu Lys Thr His
 1               5                  10                  15

Gly Arg Glu

<210> SEQ ID NO 400
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 400

Met Leu Ala Glu Arg Lys Ala Glu Glu Arg Arg Trp Leu Gln Thr His
 1               5                  10                  15

Gly Arg Glu

<210> SEQ ID NO 401
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Met Leu Ala Glu Arg Asn Ala Glu Glu Arg Arg Trp
 1               5                  10

<210> SEQ ID NO 402
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Met Phe Ala Glu Arg Lys Ala Glu Glu Ser Arg Trp Leu Gln Ser Gln
 1               5                  10                  15

Gly Arg Glu

<210> SEQ ID NO 403
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Met Leu Glu Glu Arg Lys Ala Glu Glu Arg Arg Trp Leu Lys Thr His
 1               5                  10                  15

Gly Arg

<210> SEQ ID NO 404
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Met Leu Ala Glu Arg Lys Ala Glu Glu Arg Arg Trp Leu Lys Met Gln
 1               5                  10                  15

Gly Arg Glu

<210> SEQ ID NO 405
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Met Leu Ala Glu Arg Asn Ala Glu Glu Arg Arg Trp Phe Tyr Thr His
 1               5                  10                  15

Gly Arg Glu

<210> SEQ ID NO 406
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Met Leu Ala Asp Gly Lys Ala Glu Glu Arg Arg Trp Leu Lys Thr His
 1               5                  10                  15

Gly Leu Asp

<210> SEQ ID NO 407
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Met Ile Ala Asp Gly Lys Ala Glu Glu Arg Arg Trp Leu Lys Thr His
 1               5                  10                  15

Gly Arg Asp

<210> SEQ ID NO 408
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Met Leu Ala Asp Gly Lys Ala Glu Glu Leu Arg Trp Leu Lys Thr Gln
 1               5                  10                  15

Gly Ser Asp

<210> SEQ ID NO 409
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Met Leu Ala Glu Arg Asn Ala Glu Glu Arg Arg Trp Leu Lys Thr His
 1               5                  10                  15

Gly Arg Asp

<210> SEQ ID NO 410
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Met Leu Ala Asp Gly Lys Ala Glu Glu Leu Arg Trp Leu Lys Thr Gln
 1               5                  10                  15

Gly Arg Glu

<210> SEQ ID NO 411
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ile Leu Ala Asp Gly Lys Ala Glu Glu Arg Arg Trp Leu Lys Thr His
 1               5                  10                  15

Gly Arg Asp

<210> SEQ ID NO 412
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Met Leu Ala Asp Gly Met Pro Glu Glu Arg Arg Trp Leu Gln Thr His
 1               5                  10                  15

Gly Arg Asp

<210> SEQ ID NO 413
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Met Leu Ala Asp Gly Glu Ala Glu Lys Arg Arg Trp Leu Asn Thr His
 1               5                  10                  15

Gly Arg Asp

<210> SEQ ID NO 414
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Met Leu Ala Asp Gly Asn Ala Glu Glu Arg Arg Trp Leu Met Thr His
 1               5                  10                  15

Gly Arg Asp

<210> SEQ ID NO 415
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Met Leu Ala Asp Gly Glu Ala Glu Lys Ala Arg Trp Leu Lys Thr Gln
 1               5                  10                  15

Gly Arg Glu

<210> SEQ ID NO 416
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Met Leu Ala Glu Gly Glu Ala Glu Lys Ala Arg Trp Leu Lys Thr Gln
 1               5                  10                  15

Gly Arg Glu

<210> SEQ ID NO 417
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Met Leu Ala Asp Gly Lys Ala Glu Glu Arg Arg Trp Leu Lys Thr Gln
 1               5                  10                  15

Gly Arg Glu

<210> SEQ ID NO 418
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Met Leu Ala Glu Arg Lys Ala Glu Glu Arg Arg Trp Leu Ser Ala His
 1               5                  10                  15

Val Arg Glu

<210> SEQ ID NO 419
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Leu Leu Gly Glu Arg Lys Ala Glu Glu Arg Arg Trp Tyr Lys Thr His
 1               5                  10                  15

Ala Arg Glu

<210> SEQ ID NO 420
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Met Leu Ala Glu Arg Lys Ala Glu Glu Arg Arg Trp Leu Met Thr His

```
                    1               5              10              15

Gly His Asp

<210> SEQ ID NO 421
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Met Leu Ala Glu Arg Lys Ala Glu Glu Arg Arg Trp Leu Lys Ser Gln
  1               5                  10                  15

Cys Leu Glu

<210> SEQ ID NO 422
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Leu Leu Ala Glu Arg Glu Ala Glu Glu Arg Arg Trp Phe Lys Thr His
  1               5                  10                  15

Gly Arg Glu

<210> SEQ ID NO 423
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Met Leu Ala Asp Gly Glu Ala Glu Ala Arg Arg Trp Phe Asn Met His
  1               5                  10                  15

Gly Arg Glu

<210> SEQ ID NO 424
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Met Leu Ala Asp Gly Arg Ala Glu Glu Ala Arg Trp Leu Lys Thr Gln
  1               5                  10                  15

Gly Ser Glu

<210> SEQ ID NO 425
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425
```

```
Met Leu Ala Glu Gly Arg Ala Glu Ala Arg Trp Leu Lys Thr Gln
  1               5                  10                  15

Gly Ser Glu
```

<210> SEQ ID NO 426
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

```
Met Leu Ala Glu Arg Glu Ala Glu Lys Ala Arg Trp Leu Lys Thr Gln
  1               5                  10                  15

Gly Arg Glu
```

<210> SEQ ID NO 427
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

```
Met Met Ala Glu Arg Lys Ala Glu Gln Arg Trp Phe Asp Ile His
  1               5                  10                  15

Gly Arg Asp
```

<210> SEQ ID NO 428
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

```
Leu Thr Ala Glu Arg Asp Ala Glu Lys Arg Arg Trp Leu Leu Thr His
  1               5                  10                  15

Gly Gly Glu
```

<210> SEQ ID NO 429
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

```
Met Leu Ala Glu Arg Gln Ala Glu Glu Arg Arg Trp Leu Lys Ser Gln
  1               5                  10                  15

Arg Gly Glu
```

<210> SEQ ID NO 430
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

```
Leu Leu Ala Glu Arg Lys Ala Glu Glu Arg Arg Trp Phe Ala Thr His
  1               5                  10                  15

Gly Arg Asp

<210> SEQ ID NO 431
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Met Leu Ala Glu Arg Glu Ala Glu Lys Leu Arg Trp Leu Lys Ser Gln
  1               5                  10                  15

Glu Arg Ala

<210> SEQ ID NO 432
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Met Leu Ala Glu Arg Lys Ala Glu Glu Arg Arg Trp Leu Lys Thr His
  1               5                  10                  15

Gly Gly Glu

<210> SEQ ID NO 433
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Cys Thr Trp Thr Asp Leu Glu Ser Val Tyr
  1               5                  10

<210> SEQ ID NO 434
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

His Thr Thr Asn Glu Gln Phe Phe Met Cys
  1               5                  10

<210> SEQ ID NO 435
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Asp Thr Trp Leu Glu Leu Glu Ser Arg Tyr
  1               5                  10
```

```
<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

His Asn Ser Ser Pro Met Val Gly Val Thr
 1               5                  10

<210> SEQ ID NO 437
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Asp Trp Gln Lys Thr Ile Pro Ala Tyr Trp
 1               5                  10

<210> SEQ ID NO 438
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Arg Trp Gly Arg Glu Gly Leu Val Ala Ala Leu Leu
 1               5                  10

<210> SEQ ID NO 439
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Trp Ser Gly Thr Arg Val Trp Arg Cys Val Val Thr
 1               5                  10

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Met Ser Leu Leu Ser Tyr Leu Arg Ser
 1               5

<210> SEQ ID NO 441
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 441

Leu Asp Leu Leu Ala Ile
 1               5

<210> SEQ ID NO 442
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Arg Ile Tyr Gly Val Lys
 1               5

<210> SEQ ID NO 443
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Met Ile Trp His Met Phe Met Ser Leu Leu Phe
 1               5                  10

<210> SEQ ID NO 444
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Phe Phe Trp Ala Ser Trp Met His Leu Leu Trp
 1               5                  10

<210> SEQ ID NO 445
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Phe Asp Asp Cys Trp Arg Glu Arg Glu Gln Phe Leu Phe Gln Ala Leu
 1               5                  10                  15

<210> SEQ ID NO 446
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Cys Gly Arg Ala Ser Glu Cys Phe Arg Leu Leu Glu Met
 1               5                  10

<210> SEQ ID NO 447
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Arg Glu Cys Phe Gln Met Leu Glu Arg
 1               5

<210> SEQ ID NO 448
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Cys Ser Ile Arg Trp Asp Phe Val Pro Gly Tyr Gly Leu Cys
 1               5                  10

<210> SEQ ID NO 449
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Trp Met Gln Cys Trp Asp Ser Leu Ser Leu Cys Tyr Asp Met
 1               5                  10

<210> SEQ ID NO 450
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Ala Leu Leu Met Cys Glu Ser Lys Leu Ala Glu Cys Ala Arg Ala Arg
 1               5                  10                  15

<210> SEQ ID NO 451
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Leu Ala His Cys Lys Lys Arg Lys Glu Glu Cys Ala Ala Gly
 1               5                  10

<210> SEQ ID NO 452
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ser Ile Asp Gly Val Tyr Leu Arg Thr Ser Arg Thr
```

```
                    1               5                  10
```

<210> SEQ ID NO 453
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

```
Ser Ile Asp Gly Val Tyr Leu Arg Thr Arg Ser Arg Thr Arg Tyr
 1               5                  10                  15
```

<210> SEQ ID NO 454
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

```
Val Arg Trp Leu Arg Gly Ser Thr Leu Arg Gly Leu Arg Asp Arg
 1               5                  10                  15
```

<210> SEQ ID NO 455
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

```
Asp Arg Gly Gly Gly Thr Val Gly Val Tyr Trp Trp Glu Ser Tyr
 1               5                  10                  15
```

<210> SEQ ID NO 456
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

```
Val Trp Gly Thr Val Gly Thr Trp Leu Glu Tyr
 1               5                  10
```

<210> SEQ ID NO 457
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

```
Leu Met Trp Val Ser Ala Tyr
 1               5
```

<210> SEQ ID NO 458
<211> LENGTH: 16
<212> TYPE: PRT
<213> ORGANISM: Artificial Sequence
<220> FEATURE:
<223> OTHER INFORMATION: Description of Artificial Sequence: Synthetic

```
        peptide

<400> SEQUENCE: 458

Arg Ala Ser Asp Glu Tyr Gly Ala Leu Val Arg Phe Cys Thr Asn Leu
  1               5                  10                  15

<210> SEQ ID NO 459
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Asn Tyr Trp Cys Asp Ser Asn Trp Val Cys Glu Ile Ala
  1               5                  10

<210> SEQ ID NO 460
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Leu Ala His Cys Leu Leu Arg Leu Glu Glu Cys Ala Ala Gly
  1               5                  10

<210> SEQ ID NO 461
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Leu Ala Leu Cys Leu Ala Arg Leu Arg Glu Cys Ala Gly Gly
  1               5                  10

<210> SEQ ID NO 462
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Cys Glu Ser Arg Leu Val Glu Cys Ser Arg Met
  1               5                  10

<210> SEQ ID NO 463
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Leu Leu Asp Ile Ala Glu Leu Lys Leu Gln Glu Cys Ala Arg Arg Cys
  1               5                  10                  15
Asn
```

<210> SEQ ID NO 464
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Lys Leu Leu Asp Ile Ala Glu Leu Lys Leu Gln Glu Cys Ala Arg Arg
 1               5                  10                  15

Cys Asn

<210> SEQ ID NO 465
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Cys Ser Thr Gly Gly Gly Leu Thr Ala Glu Arg Asp Ala Glu Lys Arg
 1               5                  10                  15

Arg Trp Leu Leu Thr His Gly Gly Glu
             20                  25

<210> SEQ ID NO 466
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Leu Thr Ala Glu Arg Asp Ala Glu Lys Arg Arg Trp Leu Leu Thr His
 1               5                  10                  15

Gly Gly Glu Gly Gly
             20

<210> SEQ ID NO 467
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Leu Thr Ala Glu Arg Asp Ala Glu Lys Arg Arg Trp Leu Leu Thr His
 1               5                  10                  15

Gly Gly Glu Gly Gly Lys
             20

<210> SEQ ID NO 468
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Leu Thr Ala Glu Arg Asp Ala Glu Lys Arg Arg Trp Leu Leu Thr His

```
                   1               5              10              15

Gly Gly Glu Gly Gly Gly Gly Gly
                20

<210> SEQ ID NO 469
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Leu Thr Ala Glu Arg Asp Ala Glu Lys Arg Arg Trp Leu Leu Thr His
  1               5                  10                  15

Gly Gly Glu Gly Gly Gly Gly Gly Lys
                20                  25

<210> SEQ ID NO 470
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Glu Ser Gly Trp Val Trp
  1               5

<210> SEQ ID NO 471
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Asn Ser Gly Trp Val Trp
  1               5

<210> SEQ ID NO 472
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Ser Gly Trp Val Trp
  1               5

<210> SEQ ID NO 473
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Pro Leu Gly Lys Cys Glu Ala Thr Cys Arg Glu Met Ala Arg Tyr Phe
  1               5                  10                  15

Asn
```

<210> SEQ ID NO 474
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ser Leu Gln Arg Cys Glu Tyr Lys Leu Ala Ser Val Arg Gly Leu Cys
 1               5                  10                  15

Asn

<210> SEQ ID NO 475
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Asp Leu Trp Tyr Leu Glu Ser Lys Leu Glu Glu Ala Ala Arg Arg Cys
 1               5                  10                  15

Asn Gly

<210> SEQ ID NO 476
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Pro Tyr Met Gly Thr Arg Ser Arg Ala Lys Leu Leu Arg Gln Gln
 1               5                  10                  15

<210> SEQ ID NO 477
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Arg Asn Ala Gly Glu Arg Arg Trp Phe Lys Thr Gln Gly Trp Tyr
 1               5                  10                  15

<210> SEQ ID NO 478
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Met Leu Ala Glu Arg Asn Ala Asp Asp Arg Arg Trp Phe Asn Thr His
 1               5                  10                  15

Gly Arg Asp

<210> SEQ ID NO 479

<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Met Met Ala Asp Gly Arg Leu Arg Asn Ser Val Gly Leu Ile Leu Trp
 1               5                   10                  15

Cys Asp

<210> SEQ ID NO 480
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

Met Leu Ala Asp Gly Arg Leu Arg Asn Val Val Gly
 1               5                   10

<210> SEQ ID NO 481
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 481

Leu Leu Ala Asp Val Arg Arg Arg Asn Gly Val Gly Leu Leu Arg Met
 1               5                   10                  15

Gly Arg Asp

<210> SEQ ID NO 482
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

Met Leu Ala Asp Gly Arg Leu Arg Asn Phe Gly Gly
 1               5                   10

<210> SEQ ID NO 483
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

Thr Tyr Met Thr Tyr Val Tyr Trp Leu Cys
 1               5                   10

<210> SEQ ID NO 484
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

Arg Phe Gly Glu Arg Trp Gly Leu
 1               5

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

His Trp Leu Trp Trp Gly Trp Asn Phe
 1               5

<210> SEQ ID NO 486
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Arg Glu Cys Phe Gln Met Leu Glu Arg Cys
 1               5                  10

<210> SEQ ID NO 487
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Ile Leu Ala His Arg Asn Ala Lys Glu Arg Arg Trp Phe Gln Lys His
 1               5                  10                  15

Gly Arg

<210> SEQ ID NO 488
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Cys Ser Thr Gly Gly Gly Leu Thr Ala Glu Arg Asp Ala Glu Lys Arg
 1               5                  10                  15

Arg Trp Leu Leu Thr His Gly Gly Glu Lys
            20                  25

<210> SEQ ID NO 489
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

-continued

```
Lys Gly Gly Gly Met Leu Ala Glu Arg Lys Ala Glu Glu Arg Arg Trp
 1               5                  10                  15

Phe Asn Thr His Gly Arg Glu
             20

<210> SEQ ID NO 490
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Lys Ser Thr Gly Gly Leu Thr Ala Glu Arg Asp Ala Glu Lys Arg Arg
 1               5                  10                  15

Trp Leu Leu Thr His Gly Gly Glu
             20

<210> SEQ ID NO 491
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Glu Gln Ser Asn Ser Gly Trp Val Trp Val Gly Gly Gly Gly Cys Lys
 1               5                  10                  15

Lys Lys Cys
```